(12) United States Patent
Isaacs et al.

(10) Patent No.: US 9,469,648 B2
(45) Date of Patent: Oct. 18, 2016

(54) REVERSAL OF DRUG-INDUCED NEUROMUSCULAR BLOCK USING NOVEL MOLECULAR CONTAINERS

(75) Inventors: Lyle David Isaacs, Silver Spring, MD (US); Da Ma, Carrboro, NC (US); Matthias Eikermann, Cambridge, MA (US)

(73) Assignees: University of Maryland, College Park, College Park, MD (US); General Hospital Corporation, Boston, MA (US)

( * ) Notice: Subject to any disclaimer, the term of this patent is extended or adjusted under 35 U.S.C. 154(b) by 406 days.

(21) Appl. No.: 13/878,612

(22) PCT Filed: Oct. 13, 2011

(86) PCT No.: PCT/US2011/056140
§ 371 (c)(1),
(2), (4) Date: Sep. 3, 2013

(87) PCT Pub. No.: WO2012/051413
PCT Pub. Date: Apr. 19, 2012

(65) Prior Publication Data
US 2013/0345273 A1 Dec. 26, 2013

Related U.S. Application Data

(60) Provisional application No. 61/392,729, filed on Oct. 13, 2010, provisional application No. 61/392,722, filed on Oct. 13, 2010.

(51) Int. Cl.
*A61K 31/415* (2006.01)
*C07D 487/22* (2006.01)
*A61K 31/122* (2006.01)
*A61K 31/787* (2006.01)
*A61K 47/22* (2006.01)

(52) U.S. Cl.
CPC ........... *C07D 487/22* (2013.01); *A61K 31/122* (2013.01); *A61K 31/787* (2013.01); *A61K 47/22* (2013.01)

(58) Field of Classification Search
CPC .................................................... A61K 31/415
See application file for complete search history.

(56) References Cited

U.S. PATENT DOCUMENTS

| 2005/0080068 A1 | 4/2005 | Isaacs et al. |
| 2006/0182795 A1 | 8/2006 | Pun et al. |
| 2009/0072191 A1 | 3/2009 | Isaacs et al. |
| 2010/0010215 A1 | 1/2010 | Isaacs et al. |

OTHER PUBLICATIONS

Ma, D., et al. "Acyclic Cucurbit[n]uril Congeners Are High Affinity Hosts." J. Org. Chem. (2010), vol. 75, pp. 4786-4795.*
Ma, Da et al. Acyclic Cucurbit[n]uril congeners are high affinity hosts, Journal of Organic Chemistry, Jun. 14, 2010, vol. 75, pp. 4786-4795.
Lagona, J. et al. The Cucurbit[n]uril family, Angewandte Chemie Int. Ed. Aug. 5, 2005, vol. 44, pp. 4844-4870.
Brull, S. et al., Residual Neuromuscular Block: Lessons Unlearned. Part II: Methods to Reduce the Risk of Residual Weakness; Anesthesia and Analgesia [online] May 2010, vol. 111, No. 1, pp. 129-140. May 4, 2010.
Kim K., et al., Functionalized curcurbiturils and their applications, Chem. Soc. Rev. [online] Nov. 7, 2006, vol. 36, Issu. 2, pp. 1-31. Nov. 7, 2006.
Hettiarachchi, G., et al., Toxicology and Drug Delivery by Cucurbit[n]uril Type Molecular Containers, PLoS One, May 6, 2010, vol. 5, No. 5, pp. 1-10. May 6, 2010.

* cited by examiner

*Primary Examiner* — Andrew D Kosar
*Assistant Examiner* — John S Kenyon
(74) *Attorney, Agent, or Firm* — Hodgson Russ LLP

(57) ABSTRACT

Provided are methods for reversing the effects of agents used for muscular immobilization and/or loss of consciousness and/or loss of pain perception. The method comprises administering a composition comprising acyclic CB[n]-type compounds to an individual in need of reversal of the effects of neuromuscular blocking agents and/or anesthetic agents such that the effects of the agent(s) are partially fully reversed.

12 Claims, 27 Drawing Sheets

(A)

(B)

| | Before Motor1 | | | 30 min after Motor1 | | | |
|---|---|---|---|---|---|---|---|
| Drug | pH | $pCO_2$ (mmHg) | $pO_2$ (mmHg) | pH | $pCO_2$ (mmHg) | $pO_2$ (mmHg) | N |
| Placebo | 7.42 ± 0.02 | 42 ± 6 | 176 ± 20 | 7.42 ± 0.04 | 41 ± 3 | 171 ± 27 | 5 |
| Motor1  30 mg/kg⁻¹ | 7.42 ± 0.03 | 42 ± 3 | 185 ± 40 | 7.42 ± 0.03 | 39 ± 2 | 179 ± 42 | 5 |
| Motor1  60 mg/kg⁻¹ | 7.43 ± 0.03 | 44 ± 6 | 147 ± 6 | 7.43 ± 0.02 | 40 ± 6 | 176 ± 76 | 5 |
| Motor1  90 mg/kg⁻¹ | 7.42 + 0.01 | 43 ± 2 | 176 + 29 | 7.41 + 0.01 | 41 + 2 | 187 + 21 | 5 |

REVERSAL OF DRUG-INDUCED NEUROMUSCULAR BLOCK USING NOVEL MOLECULAR CONTAINERS

CROSS-REFERENCE TO RELATED APPLICATIONS

This application claims priority to U.S. provisional patent application Nos. 61/392,722, filed Oct. 13, 2010, and 61/392,729, filed Oct. 13, 2010, the disclosures of which are incorporated herein by reference.

STATEMENT REGARDING FEDERALLY SPONSORED RESEARCH

This invention was made with government support under grant no. CHE0615049 awarded by the National Science Foundation. The government has certain rights in the invention.

FIELD OF THE INVENTION

The present invention relates generally to reversal of the effects of agents used to immobilize and anesthetize patients during medical interventions. More particularly, the invention relates to reversal of both, drug-induced neuromuscular block, and anesthesia by administering novel acyclic CB[n]-type container compounds to individuals in need of such

BACKGROUND OF THE INVENTION

General anesthesia is a drug-induced, reversible condition comprising five behavioral states: hypnosis (loss of consciousness), amnesia, analgesia, and immobility (no movement in response to pain stimuli), and hemodynamic stability with control of the stress response. Anesthetics such as ketamine are used to provide all of the above behavioral states. Neuromuscular blocking agents (NMBAs) are used to provide immobility (muscle relaxation) in anesthetized patients, as part of conventional medical procedures where administration of anesthesia is required. For example, NMBAs are used to enable safe endotracheal intubation for administration of anesthesia. They are also used to facilitate access of surgeons to body cavities without the risk of voluntary or reflex muscle movements which if left unchecked can compromise the precision required for such interventions. NMBAs can also be used in the care of patients for whom mechanical ventilation is necessary, but sedation and analgesia alone are inadequate to render the patient amenable to insertion and/or ongoing operation of a suitable ventilation apparatus.

Pharmacological reversal of the effects of NMBAs is typically used at the end of surgery. Currently in the U.S. all approved reversal agents are acetylcholinesterase inhibitors which inhibit metabolism of acetylcholine. However, these inhibitors have many side effects, such as bradycardia, hypersalivation, hypotension, and bronchospasm. While some of these undesirable effects can be alleviated by co-administration of muscarinergic acetylcholine receptor agonists, such as atropine, the co-administered agents themselves can also trigger unwanted effects, such as blurred vision, dry mouth and tachydardia. Furthermore, acetylcholinesterase inhibitors can only be used when neuromuscular activity has already recovered to 10% of normal activity, but deeper muscle blocks cannot be reversed by acetylcholinesterase inhibitors. While sugammadex, a cyclodextrin molecule that encapsulates an inactivates steroidal NMBAs has been used in some countries for reversal of rocuronium and vecuronium induced neuromuscular block, use of this agent in the U.S. was curtailed by the Food and Drug Administration because of severe allergic reactions and coagulation abnormalities induced by it. In addition, benzylisoquinoline-type NMBA compounds, which represent about 30% of the current market volume for NMBA, cannot be reversed by sugammadex. Moreover, it is not possible with any available drug to reverse benzylisoquinoline-type NMBA (e.g., atracurium or cisatracurium). Additionally, although the actions of many drugs used in anesthesiology are reversed pharmacologically when no longer desired (e.g., NMBAs, opioids, benzodiazepines), this is not the case for general anesthetic induced loss of consciousness. Thus, there is an ongoing and unmet need for improvements in reversal of drug-induced neuromuscular block.

BRIEF SUMMARY OF THE INVENTION

The present invention provides a method for reversal of the effects of agents used for muscular immobilization and/or loss of consciousness and/or loss of pain perception. The method comprises administering a composition comprising a compound of the invention to an individual in need of reversal of the effects of NMBAs and/or anesthesia such that the effects of the agent(s) are partially or fully reduced. The compositions used in the present invention contain compound(s) having the following structure:

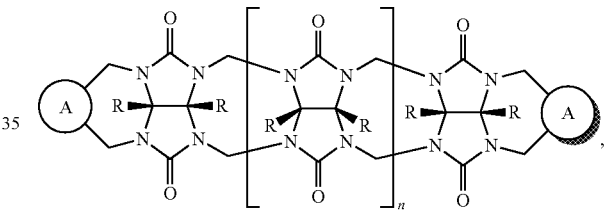

where each R is independently hydrogen, $C_1$ to $C_{20}$ alkyl group, $C_3$ to $C_{20}$ carbocyclic group, $C_1$ to $C_{20}$ heterocyclic group, carboxylic acid group, ester group, amide group, hydroxy, or ether group. Optionally, adjacent R groups form a $C_3$ to $C_{20}$ carbocyclic ring or heterocyclic ring. Each

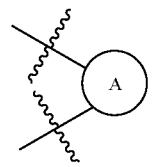

is independently a $C_5$ to $C_{20}$ carbocyclic ring system or $C_2$ to $C_{20}$ heterocyclic ring system, where the ring system comprises one or more rings. At least one of the ring systems has at least one solubilizing group selected from sulfonic acid, sulfonate salt, phosphonic acid, phosphonate salt, and polyethylene glycol. Optionally, the ring system has a targeting group. The value of n is 1 to 5.

DETAILED DESCRIPTION OF THE INVENTION

Figure 1:
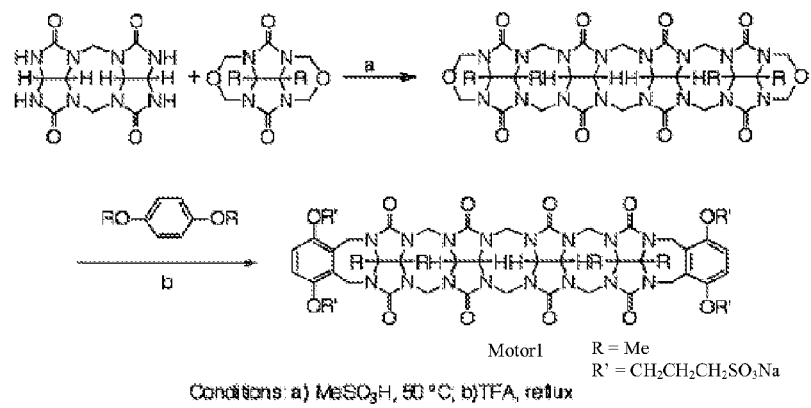
FIG. 1. Example of a Synthesis of Motor1
FIG. 2. Example of a Synthesis of Motor2
FIG. 3. Example of a Synthesis of Propargyl Host FIG. 4. Example of a Synthesis of Ethanesulfonate Wall FIG. 5. Example of a Synthesis of Butanesulfonate Wall FIG. 6. Example of a Synthesis of 2,7-naphthalene sulfonate Wall FIG. 7. Example of a Syntheses of Ethanesulfonate Host and Butanesulfonate Host FIG. 8. Example of a Synthesis Napthalene Propanesulfonate Host FIG. 9. Example of a Synthesis of Tetrabromo Host FIG. 10. Example of a Synthesis of Tetrathiophenyl Host FIG. 11. Example of a Synthesis of Tetraoctanethioether Host FIG. 12. Example of a Syntheses of PEG350, PEG750, PEG1900, PEG5000 Hosts FIG. 13. Example of a Synthesis of Dibromo Dipropanesulfonate Host FIG. 14. Example of a Synthesis of Tetraester Host FIG. 15. Example of a Synthesis of Tetrahydroxy Host FIG. 16. Example of a Synthesis of Tetrathioacetate Host FIG. 17. Example of a Synthesis of Tetratriazole Host FIG. 18. An example of a Job plot of Motor1 and Rocuronium bromide (total concentration 10 mM, 20 mM $NaH_2PO_4$ buffer, pH 7.4): (A) Stack plot of $^1H$ NMR spectra; (B) Job plot of Rocuronium bromide (constructed using the chemical shift of the acetate singlet).

The present invention is related to the use of compositions that are further described herein for reversal of the effects of agents used for muscular immobilization and/or loss of consciousness and/or loss of pain perception. The present invention is based at least in part on the surprising aqueous solubility of the acyclic CB[n]-type compounds described herein. For example, the compounds can exhibit greater than or equal to 100 mM solubility in aqueous solvents (e.g., water), which is an unexpected improvement over previously available compounds.

In various embodiments the invention is suitable for use in reversal of drug-induced neuromuscular block, or for reversal of anesthesia, or for combinations thereof. The invention provides for partial or full reversal of the effects of the agents. The degree of reversal of the effect of any particular agent can be determined, for instance, for any particular dosage or time point using techniques known to the skilled artisan.

In general, NMBAs, the effects of which can be reversed by the invention, can be divided into two categories that relate to their mechanism of action on certain cellular receptors. These categories are depolarizing NMBA and non-depolarizing NMBAs.

Without intending to be constrained by any particular theory, depolarizing NMBAs are considered to act by binding to nicotinic acetylcholine receptors (nAChRs) at the neuromuscular junction, which results in an initial opening of the ion channel associated with the particular nAChR. Thus, depolarizing NMBAs mimic the activity of acetylcholine, which is an endogenously produced neurotransmitter. However, depolarizing NMBAs are metabolized relatively slowly by cholinesterase enzymes, which stands in contrast to the rapid hydrolysis of endogenous acetylcholine by acetylcholinesterases. Accordingly, depolarizing NMBAs bind to nAChRs for a much longer time period than acetylcholine. Consequently they effect a persistent depolarization of the plasma membrane of skeletal muscle fiber, which makes the muscle fiber resistant to further stimulation by acetylcholine, which in turn results in a neuromuscular block.

In contrast to depolarizing NMBAs, non-depolarizing NMBAs are competitive inhibitors of nAChRs which do not activate the ion channel when bound to the nAChR. Instead, they block the activation of the channel by acetylcholine and thereby prevent cell membrane depolarization. This results in flaccid muscle tissue.

In various embodiments, the invention facilitates reversal of neuromuscular block induced by an NMBA that is a competitive inhibitor of nAChRs (which prevents the physiological agonist, acetylcholine, from depolarizing the skeletal muscles). Consequently, the invention will restore the skeletal muscle function in various embodiments within a few seconds.

Most clinically-used NMBAs belong to the non-depolarizing category. These include but are not necessarily limited to steroidal and benzylisoquinoline-type neuromuscular blocking agents. Those skilled in the art will readily recognize the structures of commercially available non-depolarizing NMBAs, the effects of any of which can be reversed by performing the method of the invention. Such NMBAs include but are not necessarily limited to those agents which are generally referred to in the art as rocuronium, tubocurarine, atracurium, atracurium besylate, cisatracurium, mivacurium, gallamine, pancuronium, vecuronium, doxacurium, metocurine, and rapacuronium. Therefore, the invention is suitable for reversing the effects of each of the compounds individually, or the effects of combinations of these compounds. Illustrative structures of each of these compounds are as follows:

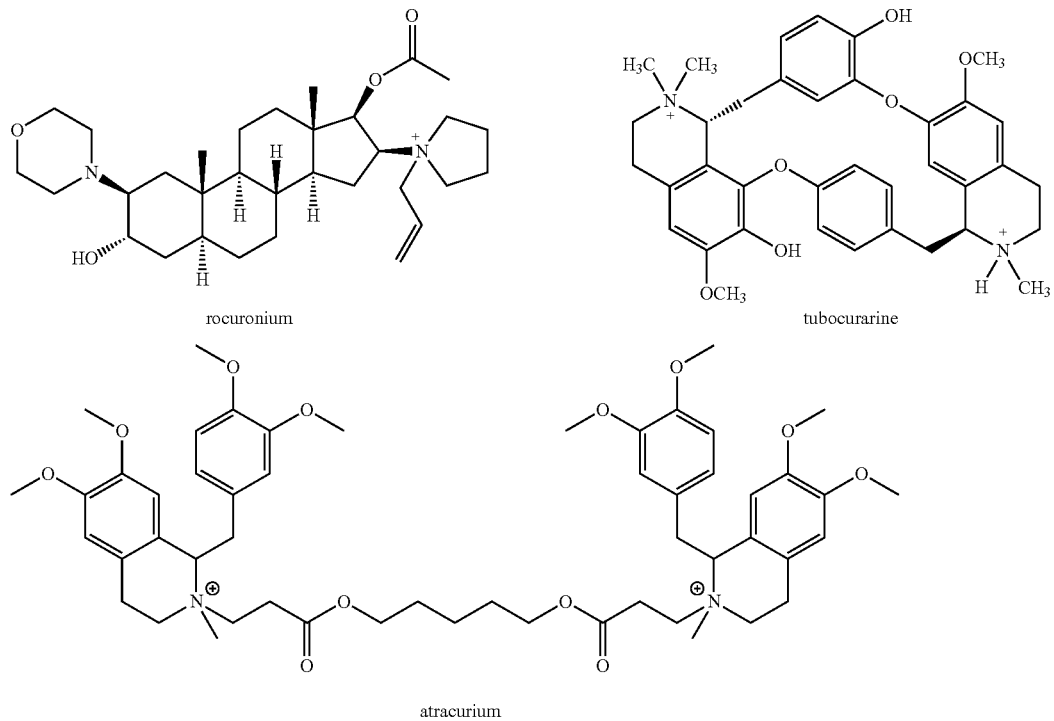

rocuronium tubocurarine atracurium

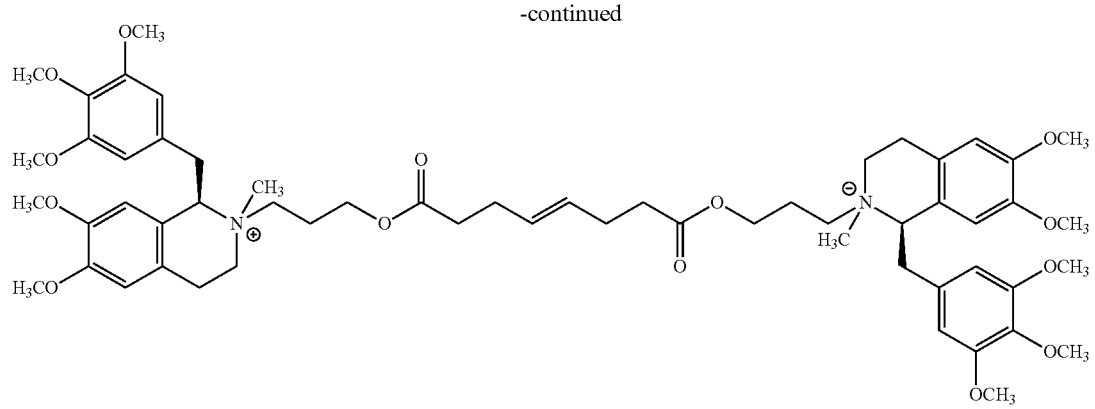
mivacurium
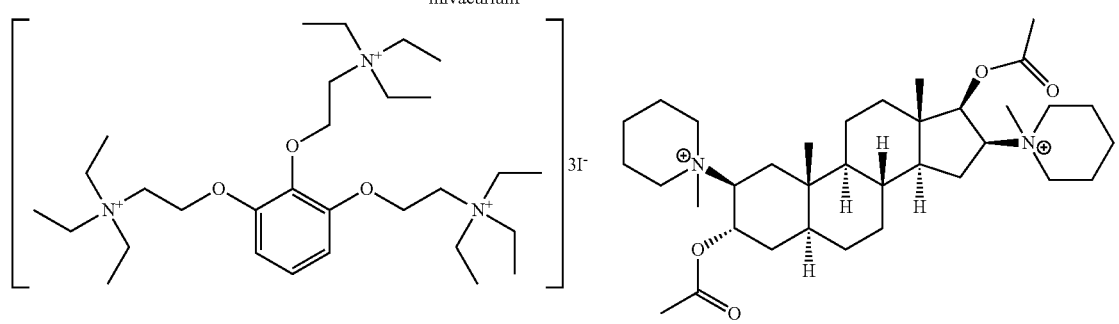
gallamine
pancuronium
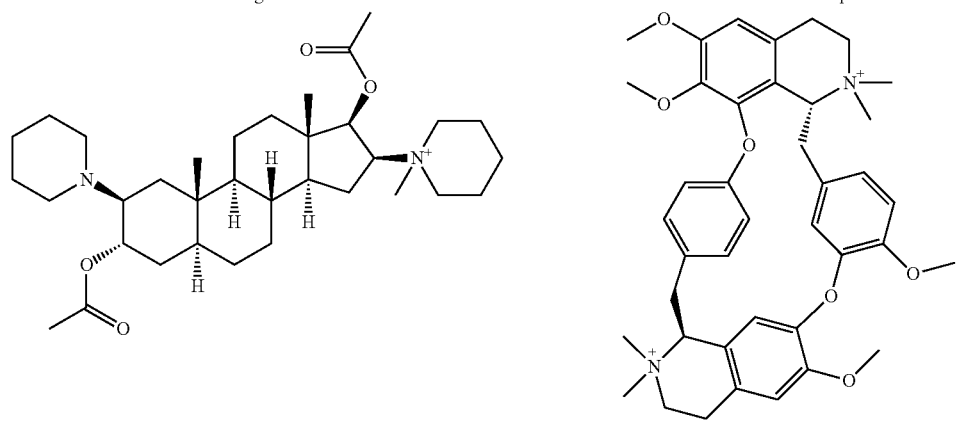
vecuronium
metocurine
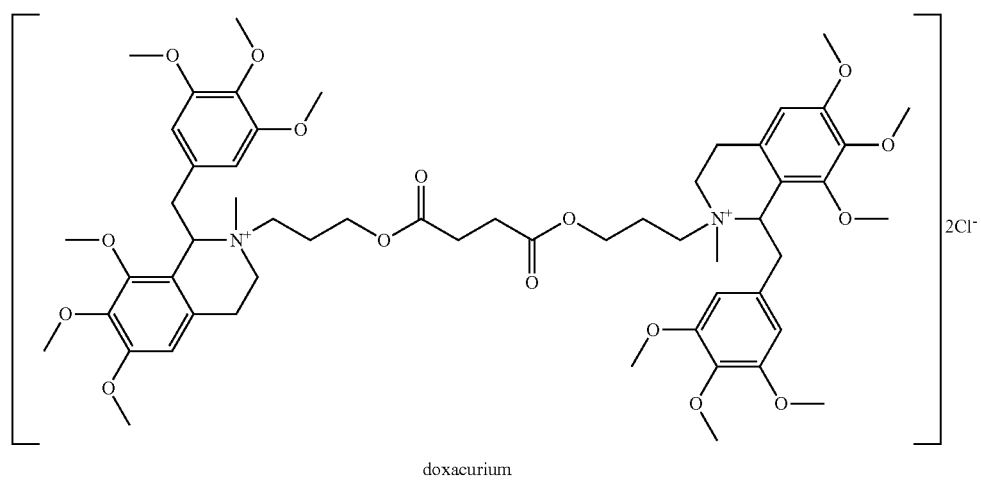
doxacurium -continued

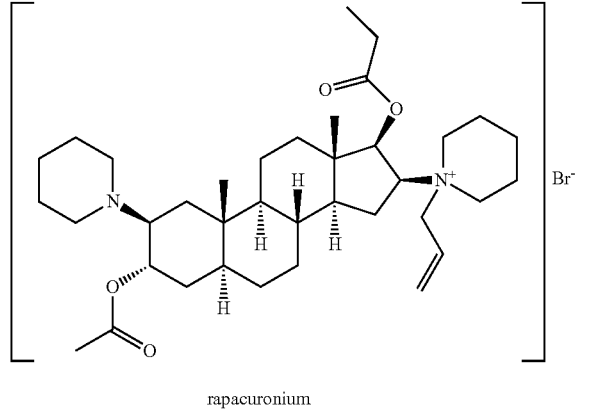

rapacuronium

In various embodiments, the compound for which the effects are reversed according to the method of the invention is provided in a form according to the foregoing structures, and includes salts, partial salts, hydrates, polymorphs, stereoisomers or a mixtures thereof. Each compound can be provided as a racemic mixture, a single enantiomer, a single diastereomer, mixture of enantiomers, or mixture of diastereomers.

Since NMBAs are used during surgery and/or for muscle relaxation during intensive care, and in Emergency Medicine, at or near the end of these treatment modalities, it is desirable to reverse the effects of the NMBA so that the patient can regain voluntary control over muscular contractions. Thus, in one embodiment, the present invention comprises administering a composition comprising a compound of the invention to an individual who is in need of reversal of a chemically induced muscular block. Accordingly, in various embodiments, the compounds of the invention can be considered to be NMBA reversal agents, or NMBA sequestrants.

The present invention also includes a method for reversing the activity of certain anesthetic agents. In this regard, in the United States, nearly 60,000 patients per day receive general anesthesia for surgery. The most severe anesthesia-related patient injuries are death or permanent brain damage, which frequently results from adverse effects of anesthetics on breathing. Further, anesthetics decrease respiratory drive and place the upper airway at risk for collapse. Typically, skilled anesthesiologists can artificially ventilate the patient in a situation where the patient is unable to breathe because of adverse effects of anesthetics and neuromuscular blocking agents. However, in some patients, artificial ventilation is difficult or impossible because the patient has an airway anatomy that does not allow inflation of the lung. The second most common life threatening side effects of anesthetics relates to depression of cardiovascular function, which can be associated with insufficient oxygen supply to the heart, leading to myocardial infarction and/or cardiac arrest. In such emergent situations, it would be desirable to reverse the effects of anesthesia and NMBAs, but this typically requires waiting until emergence (the time of recovery of consciousness and neuromuscular transmission from drug effects), such that breathing and adequate circulation of blood are restored. Emergence from general anesthesia has been treated as a passive process whereby anesthetic drugs are merely discontinued at the end of surgery and no drugs are administered to actively reverse their effects on the brain and central nervous system. The timing of emergence can be unpredictable because many factors, including the type of surgery and the age, physical condition of the patient affects the pharmacokinetics and pharmacodynamics of general anesthetics. Although the actions of many drugs used in anesthesiology are reversed pharmacologically when no longer desired (e.g., some muscle relaxants, or opioids such as morphine), this is not the case for general anesthetic induced loss of consciousness. Until the previous invention, there was no agent available to actively induce emergence from general anesthesia. However, we now demonstrate feasibility of the present invention for reversing activity of anesthetics.

In particular, we show that the effects of a certain group of anesthetics, N-methyl D-aspartate (NMDA) receptor antagonists, such as ketamine, can be reversed using the instant method. Ketamine is primarily used for the induction and maintenance of general anesthesia. It is also used for monitored anesthesia care, also known as conscious sedation, and as an analgesic, both in humans and in veterinary medicine. In the present case, we administered by continuous infusion ketamine to rats to induce steady-state, deep anesthesia, resulting in depression of respiratory and cardiovascular function. The effects of Motor2 induced reversal of ketamine anesthesia are striking: the rat woke up within 2 minutes following injection of Motor2 (200 mg). Respiratory rate and arterial blood pressure increased, an electro-encephalogram (EEG) showed wakefulness-like electrical activity. Thus, since ketamine is freqeuntly used for human and non-human animal anesthesia, in various embodiments of the invention, the individual in which a reversal of the effects of an NMBA or an anesthetic agent can be a human or a non-human animal, and includes but is not necessarily limited to any mammal. In certain embodiments, the animal in need of a composition of the invention is a human, a feline, a canine, an equine or a bovine animal. Thus, the invention has broad applicability in a variety of medical interventions and across various species.

In certain embodiments, the invention is also useful for reversing the effects of short acting anesthetics, such as etomidate. Etomidate, similar to ketamine, is a short acting anesthetic agent which is typically administered intravenously for the induction of general anesthesia for medical procedures which can be performed in relatively short time frames, such as for correction of dislocated joints.

Extracorporal application of the compositions of the invention is also contemplated. For instance, compounds of the invention could be used by mixing the compositions with a biological fluid from an individual, such as during dialysis or during plasmapheresis. Therefore, in various embodiments, the invention provides an extracorporal composition comprising a compound of the invention. The extracorporal composition, to the extent it contains a biological fluid that has been transiently separated from the body, can be considered an isolated composition according to the invention. The extracorporal composition can in various embodiments can comprise or consist of blood, urine or plasma (in addition to a compound provided by the invention).

In one embodiment, the invention provides for formation of a guest-host complex comprising a non-covalently associated complex of a compound of the invention and an NMBA. The guest-host complex can therefore be considered to be an organized chemical entity resulting from the association of two or more components of the NMBA and the host held together by non-covalent intermolecular forces. Without intending to be bound by theory, we believe we have shown in an animal model that the binding of this guest-host complex is very stable, such that reversal of drug effects is stable and the guest-host complex is eliminated in urine within 2-3 hours. This unique pharmacokinetic-pharmakodynamic constellation has important implications for clinical anesthesia, critical care medicine and emergency medicine where respiratory side effects of anesthetics and neuromuscular blocking agents need to be reversed in due time in order to restore breathing and cardiovascular function.

For use in the invention, the compositions described herein can be administered as pharmaceutical preparations. Thus, they can be provided in a variety of solutions of various compositions, and can be combined with one or more standard pharmaceutically acceptable carriers. Some examples of pharmaceutically acceptable carriers can be found in: *Remington: The Science and Practice of Pharmacy* (2005) 21st Edition, Philadelphia, Pa. Lippincott Williams & Wilkins Various methods known to those skilled in the art may be used to introduce the compositions of the invention to an individual. These methods include but are not limited to intravenous, intramuscular, intracranial, intrathecal, intradermal, subcutaneous, and oral routes. In one embodiment, the composition is administered intravenously. The composition can be provided as a liquid, a solution, or a solid, and may be provided in combination with any suitable delivery form or vehicle, examples of which include but are not limited to caplets, capsules, tablets, an inhalant or aerosol, etc.

The dose of the composition to be used will necessarily be dependent upon the needs of the individual to whom the composition of the invention is to be administered. These factors include but are not necessarily limited to the weight, age, sex, medical history, muscular composition of the individual, and the degree of muscular activity and/or level of consciousness to be restored. In this regard, our data show high in-vitro binding affinity of compounds of the invention to NMBAs and anesthetics translates to higher speed of reversal for these drugs.

To perform the present invention, a composition comprising a compound of the invention is administered to the individual as detailed above. The compounds used in the method are acyclic CB[n]-type compounds.

In performing the present invention, we demonstrate formation of complexes of compounds of the invention and NMBAs and certain anesthetic agents and provide a characterization of certain reaction kinetics associated therewith as more fully described below. Further, we demonstrate that compounds of the invention are non-toxic to human cells.

Further still, we tested an embodiment of the invention by administration of the commonly used NMBA rocuronium 3.5 mg/kg and cisatracurium 0.5 mg/kg to 10 anesthetized, tracheostomized, mechanically ventilated rats, which induced complete atonia of all skeletal muscles, resulting in long-lasting apnea. More specifically, for surgical procedures described in the Examples presented herein, rats were anesthetized (isoflurane 5% induction, 1,5% maintenance, in 70% $N_2O$/30% $O_2$) and tracheotomized. Spontaneous breathing was maintained during surgery and if possible according to normal protocol. Rats lay in the supine position with the head supported in a neutral position in the midline on a soft piece of tissue. The left femoral vein and artery were cannulated for drug infusion and blood sampling. Arterial blood gases and pH were measured every 10 or 30 minutes (Corning 178; Corning, N.Y., USA) and continuous measurement of blood pressure (PowerLab; ADInstruments, Colorado Springs, Mo.) and heart rate were performed. If mechanical ventilation was necessary animals were ventilated through a tracheostomy (SAR-830; CWE, Ardmore, Pa., USA). Rectal temperature was kept at 37.0±0.1° C. using a thermostatic heating pad (FHC, Bowdoinham, Me.). Level of anesthesia was maintained throughout the experiment to eliminate cardiovascular response to tail pinch. In all treatment groups, systemic physiological parameters were kept well within normal range. The right leg was shaved and the femoral nerve was stimulated supramaximally with subcutaneous needle electrodes, and the evoked response of the quadriceps femoris muscle was measured by accelerometry, with the TOF-Watch SX Monitor (Organon Ireland Ltd, a part of Schering-Plough Corporation, Dublin, Ireland), as described previously (Fassbender et al, Anesthesiology 2007). The transducer was fixed to the skin ventromedially at the proximal end of the thigh, next to the tibial tuberosity (insertion point of the patellar ligament).

After determination of the supramaximal stimulation current and calibration of the TOF-Watch (cal 1 mode), we stimulated the femoral nerve continuously at 1 Hz (10 mA±2 mA) for at least 10 minutes until twitch height reached a stable plateau. We then re-calibrated the TOF-Watch SX monitor, took a baseline train-of-four (TOF) at 2 Hz, and continued to stimulate the femoral nerve at 1 Hz with the single twitch mode until drugs were infused.

To obtain an estimate of the efficacy of rocuronium at the rat quadriceps femoris muscle and its reversibility by Motor1, all rats were anaesthetized with isoflurane 2-5 vol % during induction and surgery (inspiratory gas: 30% $O_2$ and 70% $N_2O$), and 1.5 vol % during measurement.

After pre-stimulation rats were paralyzed with rocuronium 3.5 mg $kg^{-1}$ (two times the ED90) as reported before (BJA 2008) and mechanically ventilated to achieve normocapnia confirmed by an arterial blood gas analysis. 30 s afteronset of complete neuromuscular block we injected Motor1 (30 mg $kg^{-1}$, n=5, 60 mg $kg^{-1}$, n=5 or 90 mg $kg^{-1}$, n=5) or placebo (saline 0.5 ml, n=5). In ten more rats, following administration of cisatracurium 0.5 mg/g, we administered Motor1 15 mg, 30 mg, and 60 mg. Finally, in four more rats, we administered Motor2 following rocuronium and atracurium induced complete neuromuscular blockade.

Endpoints included time to recovery of spontaneous breathing, twitch height as well as TOF-ratio. Arterial pressure and heart rate were measured continuously, and arterial blood gas was measured directly before application of Motor1 and 30 minutes later. Arterial blood samples were collected at baseline, 2, 5, 10, 15, 20 and 60 minutes and subsequently processed for plasma samples which were stored at −80° C. until analyzed. At 60 min after the injection of Motor1 urine was collected and stored at −80° C. until analysis.

For the urine samples, we took 0.1 mL from each urine sample and dried them under high vacuum. Then they were dissolved in 0.5 mL $D_2O$, and 0.1 mL of 60 mM reference solution (1,3,5-tricarboxylate benzene) was added. NMR spectra were taken and the concentration of Motor1 in urine was calculated from the ratio between the integration of diagnostic peak for reference (8.3 ppm, 3H) and Motor1 (1.9-1.5 ppm, 12H).

We determined that Motor1 reversed rocuronium effectively, in a dose-dependent fashion. Normal breathing recovered after 720±s [placebo, i.e., 1 cc of normal saline), 120±15 s, 15±5 s, and 8±3 seconds after Motor1 10 mg, 20 mg, and 30 mg, respectively, were administered. The quadricepts femors twitch height was normalized after 960±s [placebo], 240±s, 120±s, and 60±s, respectively, after Motor1 10 mg, 20 mg, and 30 mg, respectively, were administered. Motor1 did not have any side effects on arterial blood-gas analysis, EKG, arterial blood pressure, or heart rate. Additionally, we have analyzed blood and urine samples from all the tested rats and did not observe any allergic reactions or adverse effects on coagulation.

Following cisatracurium, normal breathing recovered after 750 (17) s (+/s shown in parenthesis) [placebo, normal saline], 28 (6)s, and 11 (4) seconds (means(SD) after 30 mg, and 60 mg Motor1, respectively. The quadirecps femors twitch height was normalized after 1002 (122) s [placebo, normal saline], 266 (17)s, 130 (14) s, and 68 (10)s, respectively. Motor1 and 2 did not have any side effects on: arterial blood-gas analysis, EKG, arterial blood pressure, and heart rate. We have taken blood and urine samples from all rats and observed that Motor1 is eliminated via urine. We did not observe any evidence of allergic actions and/or adverse effects on coagulation.

To evaluate the effectiveness to reverse ketamine, anesthesia was induced with 3% isoflurane, and maintained for surgical instrumentation with 1.5% isoflurane. We cannulated the femoral vein (times 2) for subsequent ketamin infusion and reversal agent injection), cannulated the artery for invasive blood pressure measurement, transected the trachea, and cannulated it with PE240 tubing through which the rat spontaneously breathed. Rats lay in the supine position with the head supported in a neutral position in the midline on a soft piece of tissue. A temperature probe was inserted into the rectum and core temperature was regulated at 37+/−1 degree Celsius using a heating pad. Two two screw electrodes (Plastics One Inc., Roanoke, Va.) were inserted into holes drilled into the skull, one approximately 1.0 mm anterior and one approximately 3 mm posterior to the bregma and approximately 1 mm lateral to the midline. The free ends of the leads were connected to an amplifier and EEG activity was filtered by a low-pass (100 Hz) filter. We also measured EKG, and videotaped the rat in order to evaluate respiratory rate, and movements. In two rats, traheostomy was not performed as to be able to evaluate noise indicating recovery from anesthesia After surgery, we discontinued isoflurane and started an infusion of either ketamine (1500 µg/kg/min). Motor2 200 mg was administered 60 minutes after discontinuation of isoflurane under steady state ketamine anesthesia while ketamine infursion was still running at a constant rate. We observed that Motor2 reverses ketamine anesthesia: increase in heart rate, blodd pressure and respiratory rate to pre-adnesthesia values, movements, spontaneous urinination, and distress calls.

The following provides a characterization of the compounds used to reverse the effects of NMBAs and anesthetics according to the method of the invention. The terms Motor1 and Motor 1 as used herein are interchangeable. The terms Motor2 and Motor 2 and used herein are also interchangeable.

As used herein, "alkyl group" refers to branched or unbranched hydrocarbons. Examples of such alkyl groups include methyl groups, ethyl groups, butyl groups, nonyl groups, neopentyl groups, and the like. For example, the alkyl group can be a $C_1$ to $C_{20}$ alkyl group, including all integer numbers of carbons and ranges of numbers of carbons therebetween.

As used herein, "carbocyclic group" refers to a cyclic compound having a ring or multiple rings in which all of the atoms forming the ring(s) are carbon atoms. The rings of the carbocyclic group can be aromatic or nonaromatic, and include compounds that are saturated and partially unsaturated, and fully unsaturated. Examples of such groups include benzene, naphthalene, 1,2-dihydronaphthalene, cyclohexane, cyclopentene, and the like. For example, the carbocyclic group can be a $C_3$ to $C_{20}$ carbocyclic group, including all integer numbers of carbons and ranges of numbers of carbons therebetween.

As used herein, "heterocyclic group" refers to a cyclic compound having a ring or multiple rings where at least one of the atoms forming the ring(s) is a heteroatom (e.g., oxygen, nitrogen, sulfur, etc.). The rings of the heterocyclic group can be aromatic or nonaromatic, and include compounds that are saturated, partially unsaturated, and fully unsaturated. Examples of such groups include imidazolidin-2-one, pyridine, quinoline, decahydroquinoline, tetrahydrofuran, pyrrolidine, pyrrolidone, and the like. For example, the heterocyclic group can be a $C_1$ to $C_{20}$ heterocyclic group, including all integer numbers of carbons and ranges of numbers of carbons therebetween.

As used herein, "carbocyclic ring system" refers to a cyclic compound having a ring or multiple rings in which all of the atoms forming the ring(s) are carbon atoms. Examples of such groups include benzene, naphthalene, 1,2-dihydronaphthalene, cyclohexane, cyclopentene, and the like. The rings of the carbocyclic ring system or heterocyclic ring system can be aromatic or nonaromatic, and include compounds that are saturated, partially unsaturated, and fully unsaturated. For example, the carbocyclic ring system can be a $C_3$ to $C_{20}$ carbocyclic group, including all integer numbers of carbons and ranges of numbers of carbons therebetween. In another example, the carbocyclic ring system can be a phenyl group or naphthyl group. The phenyl group or naphthyl group is attached to the compound via adjacent carbons of the phenyl group or naphthyl group.

As used herein, "heterocyclic ring system" refers to a cyclic compound having a ring or multiple rings in which at least one of the atoms forming the ring(s) is a heteroatom (e.g., oxygen, nitrogen, sulfur, etc.). The rings of the carbocyclic ring system or heterocyclic ring system can be aromatic or nonaromatic, and include compounds that are saturated, and fully unsaturated. Examples of the heterocyclic ring system include imidazolidin-2-one, pyridine, quinoline, decahydroquinoline, tetrahydrofuran, pyrrolidine, pyrrolidone, and the like. For example, the heterocyclic ring system can be a $C_1$ to $C_{20}$ heterocyclic group, including all integer numbers of carbons and ranges of numbers of carbons therebetween.

Any of these groups and/or rings may each be substituted with alkyl groups and other substituents such as, for example, nitro, cyano, keto, carboxy, alkoxy, hydroxyl, amine, amide, halide (e.g., bromide, chloride, fluoride, and iodide), and alkoxy groups. For example, the alkyl groups or aryl groups may be further substitituted. For example, the alkyl group can be halide substituted (e.g., a 2-chloroethyl group). As another example, a carbocyclic group can be cyano substituted (e.g., 3-cyano naphthalene).

In an aspect, the present invention provides acyclic CB[n]-type compounds having the following structure:

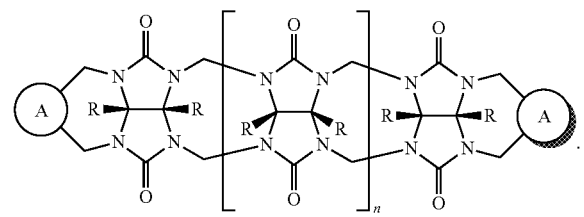

Each R is independently hydrogen, $C_1$ to $C_{20}$ alkyl group, $C_3$ to $C_{20}$ carbocyclic group, $C_1$ to $C_{20}$ heterocyclic group, carboxylic acid group, ester group, amide group, hydroxyl, or ether group. The carboxylic acid, ester, amide, and ether groups can have from 1 to 20 carbons, including all integer values and ranges therebetween. Optionally, adjacent R groups form a $C_3$ to $C_{20}$ carbocyclic ring or heterocyclic ring, where the carbocyclic ring is a ring in which all of the atoms forming the ring(s) are carbon atoms and the heterocyclic ring is a ring where at least one of the atoms forming the ring(s) is a heteroatom (e.g., oxygen, nitrogen, sulfur, etc.). These rings may each be substituted with alkyl groups and other substituents such as, for example, nitro, cyano, keto, carboxy, alkoxy, hydroxyl, amine, amide, halide (e.g., bromide, chloride, fluoride, and iodide), and alkoxy groups.

Each

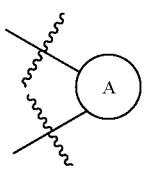

is independently a $C_5$ to $C_{20}$ carbocyclic ring system or $C_2$ to $C_{20}$ heterocyclic ring system. At least one

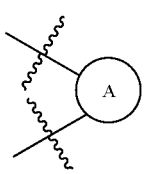

of the compound has at least one solubilizing group. In an embodiment, both

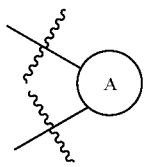

s of the compound have at least one solubilizing group. In an embodiment, one

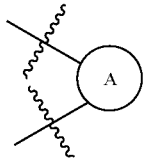

of the compound has at least one solubilizing group. In various embodiments, the ring system has 1, 2, 3, 4, 5, or 6 solubilizing groups. Optionally, the ring system has a targeting group. The value of n is 1 to 5, including all integer values therebetween. In an embodiment, the

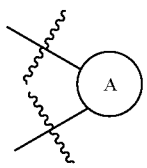

groups are the same.

In various embodiments, the compound is a salt, a partial salt, a hydrate, a polymorph, a stereoisomer or a mixture thereof. The compounds can have stereoisomers. For example, the compound can be present as a racemic mixture, a single enantiomer, a single diastereomer, mixture of enantiomers, or mixture of diastereomers.

Without intending to be bound by any particular theory, it is considered that the solubilizing group (or groups) increase (or impart) solubility of compounds in water or aqueous solvent systems. The solubilizing group can be a functional group that can be deprotonated over a broad pH range. The solubilizing group can have a cationic (e.g., ammonium and sulfonium groups), anionic (e.g., sulfate, sulfonate, phosphate, and phosphonate groups) or neutral group (e.g., sulfonic acids, phosphonic acids, polyethylene glycol (PEG) ethers (including PEG ether oligomers), crown ethers, and cyclam groups). Another example of a neutral solubilizing group is a zwitterionic group (e.g., a group with both an ammonium group and a sulfonate group), where both ionic groups are covalently bonded to the compound. It is desirable that cationic solubilizing groups not interact with cavity of the compound. The compound can have mixtures of solubilizing groups. In an embodiment, the solubilizing group selected from sulfonic acid, sulfonate salt, phosphonic acid, phosphonate salt, and polyethylene glycol. The solubilizing group can be connected to the linking group though a heteroatom, such as oxygen or sulfur. For example, the PEG group can be connected to the compound through a sulfur atom forming a thioether moiety. For example, the polyethylene glycol group can have a molecular weight of from 107 to 100,000, including all integer values and ranges therebetween.

In one embodiment, the solubilizing group or groups are not carboxylic acids or carboxylic acid salts. In one embodiment, at least one of the solubilizing groups is not a carboxylic acid or carboxylic acid salt.

The targeting group is a moiety that interacts with, for example, a cell. A targeting group (TG) is a moiety that targets, for example, tumor cells by either passive or active targeting by methods known in the art. Examples of targeting groups include dendrons, dendrimers, PEG groups, peptides, polypeptides, folates, amidines, antibodies, proteins, steroids, mono or oligosaccharides, and the like.

In an embodiment, each

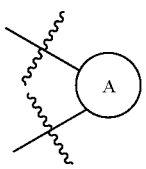

of the compound is independently a $C_5$ to $C_{20}$ carbocyclic ring system having one of the following structures:

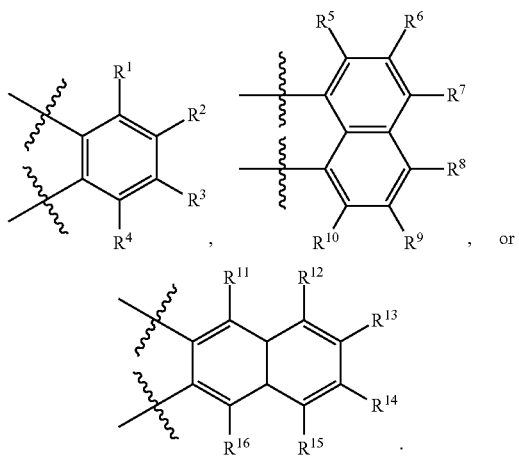

At each occurrence of

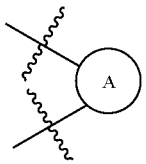

$R^1$ to $R^{16}$ is independently hydrogen, $C_1$ to $C_{20}$ alkyl group, halo group, hydroxyl group, nitro group, carboxylic acid group, ester group, amide group, ether group, $C_3$ to $C_{20}$ carbocyclic group, or $C_1$ to $C_{20}$ heterocyclic group. For example, the carboxylic acid group, ester group, amide group, and ether groups can have from 1 to 20 carbons, including all integer values and ranges therebetween. At least one of $R^1$ to $R^{16}$ in the compound has the following structure:

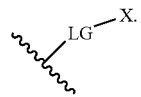

LG is a linking group and X is the solubilizing group. Optionally, one or more adjacent $R^1$ to $R^{16}$ groups are connected forming a carbocyclic or heterocyclic ring, and the ring can be substituted or unsubstituted.

As used herein, "adjacent" refers to groups attached through 2 or 3 carbons as depicted by, for example,

in the structures:

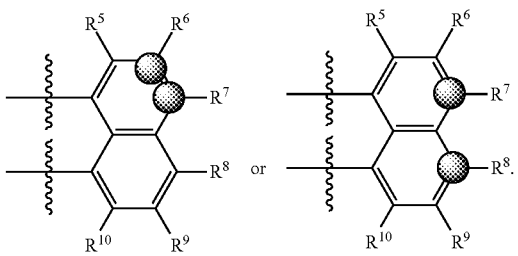

It is contemplated that groups can be attached through any two adjacent carbons.

A linking group (LG) is a group that connects

with a solubilizing group (X) or a targeting group (TG). The linking group can be, for example, an alkoxy moiety or an alkyl moiety. The linking group can have independently at each occurrence a thioether linkage, ether linkage, amino linkage, amide linkage, ester linkage, triazole ring linkage, or a combination thereof. For example, these linkages can join the linking group and solubilizing group or targeting group. In an embodiment, the linking group, LG, is a 1-substituted triazole.

In an embodiment,

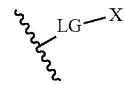

has the following structure:
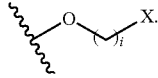
The value of each i is independently 1 to 20, including all integer values therebetween.
In an embodiment, at least one of the $R^1$ to $R^{16}$ groups in the compound has the following structure:
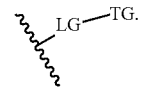
LG is a linking group and TG is a targeting group.
In an embodiment, the compound has one of the following structures:
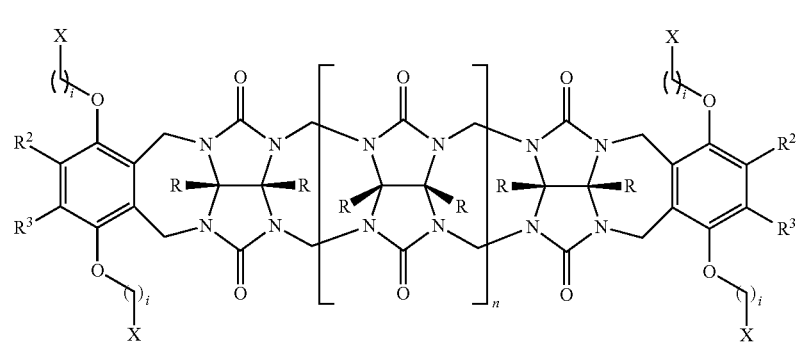
(I)
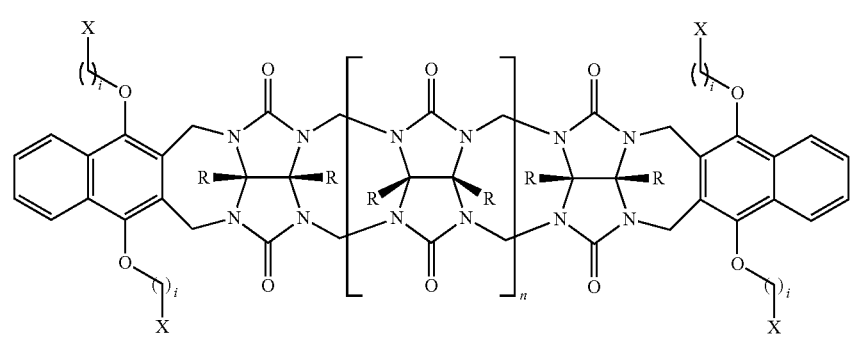
(II)
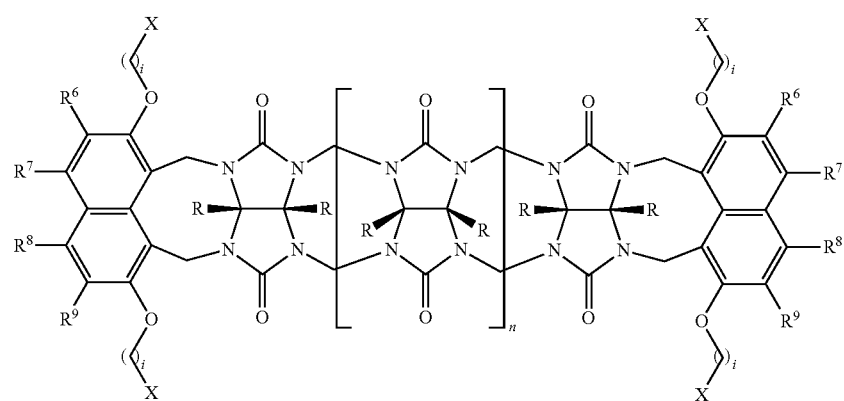
(III)

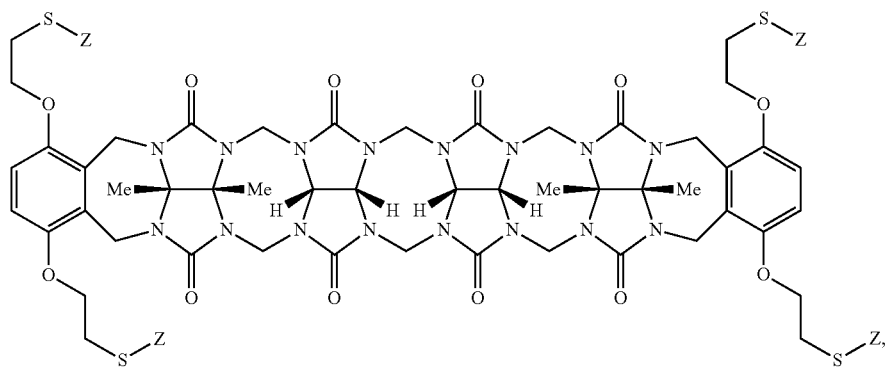

(IV)

wherein Z is PEG group. In an embodiment, the PEG group has a molecular weight of 200 to 10,000, including all integers and ranges therebetween. In an embodiment, the PEG group has a molecular weight of 350 (PEG350), 750 (PEG750), 1900 (PEG1900), or 5000 (PEG5000).

Compounds having the structures of formulae I-IV can be prepared, for example, by the synthetic methodology described in Example 1-2. In this embodiment, R, $R^2$, $R^3$, $R^6$, $R^7$, $R^8$ and $R^9$ are as defined herein.

In various embodiments, the compounds have the following structures:

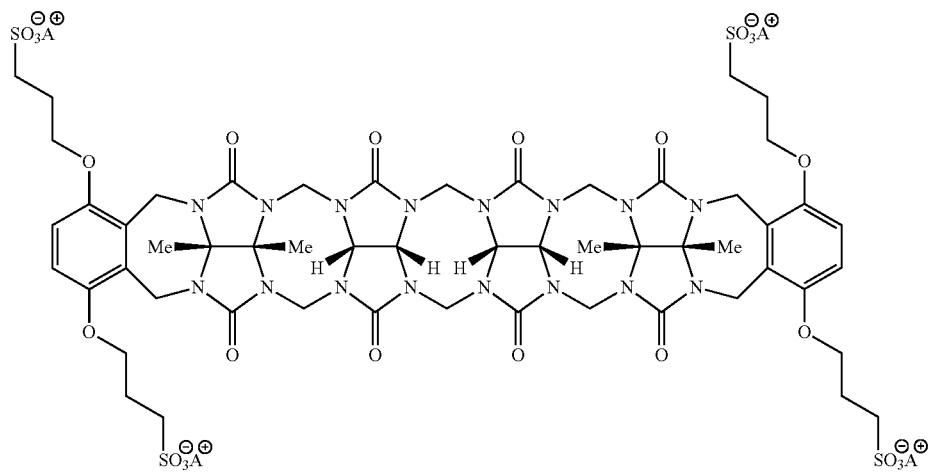

(referred to herein as Motor 1),

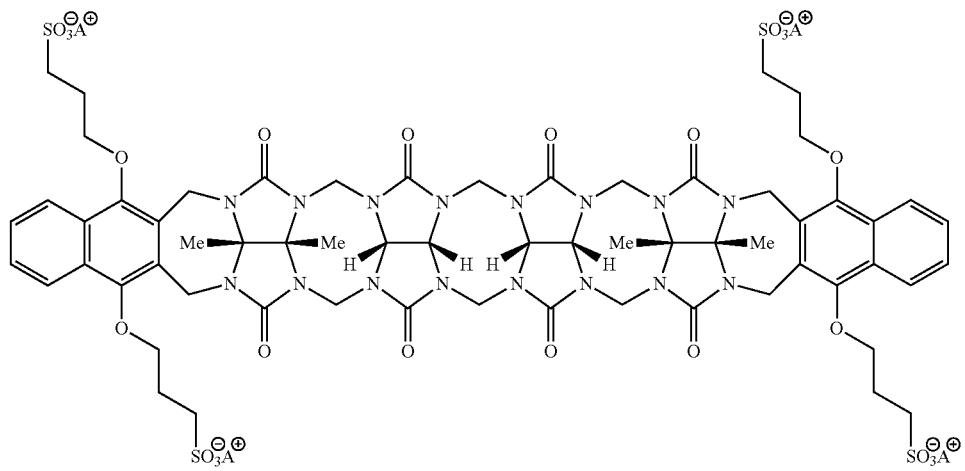

(referred to herein as Motor 2),

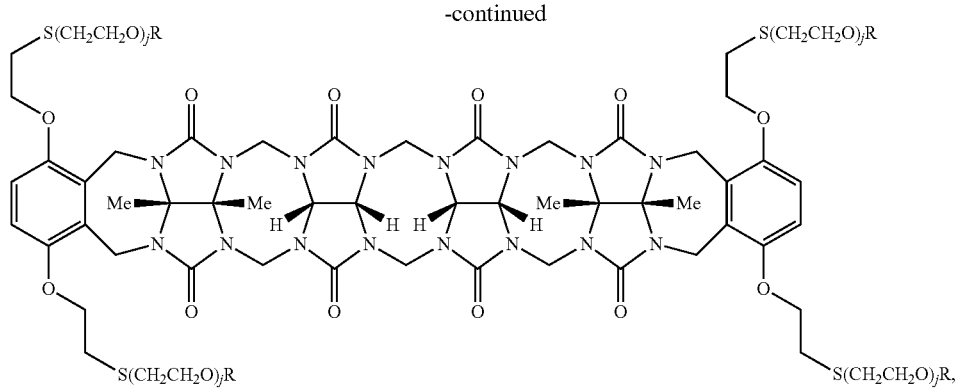
where j is, for example, 1 to 2250, including all integer values and ranges therebetween, and R in this example is hydrogen or an alkyl group,
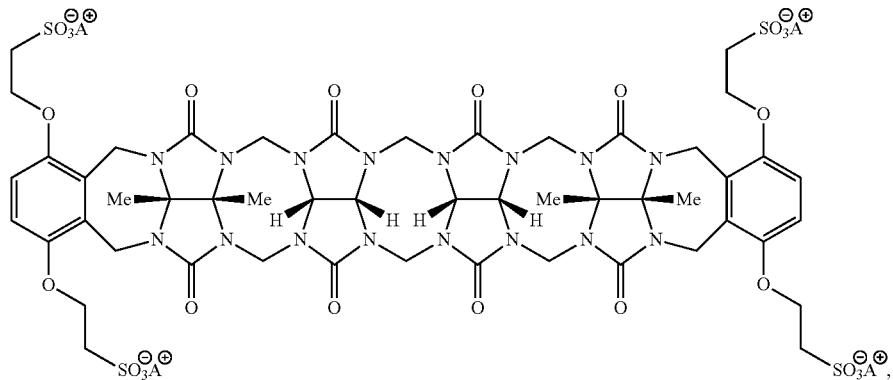
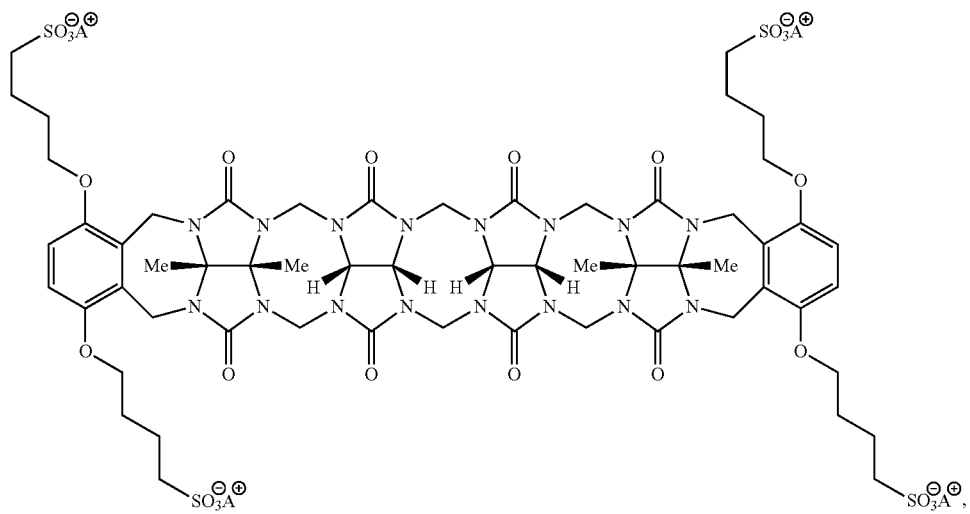

-continued

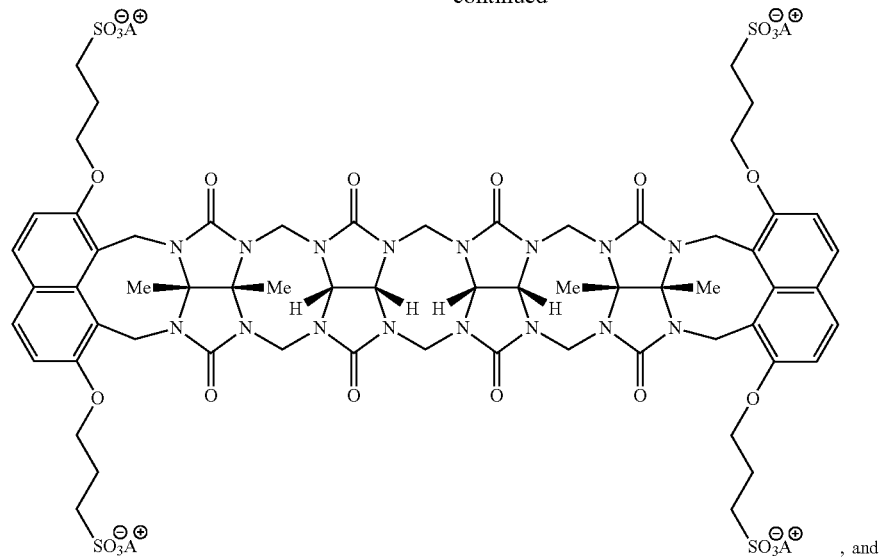

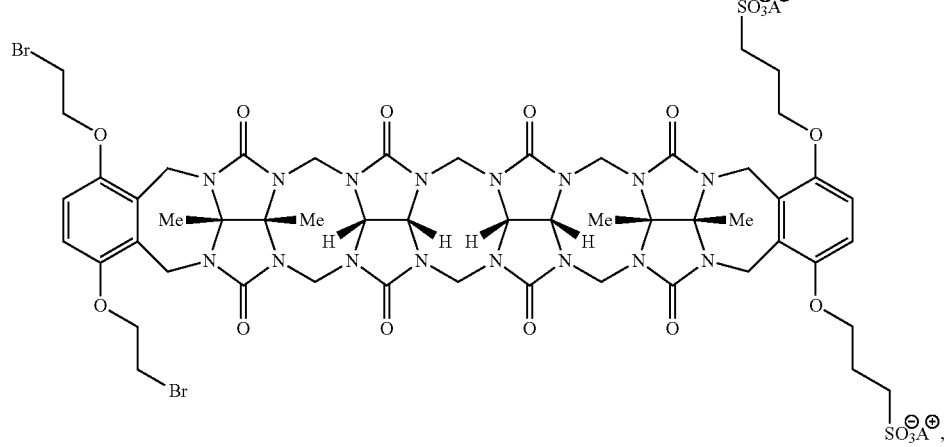

where A⁺ can be H⁺, Na⁺, K⁺, Ca²⁺, Mg²⁺, Zn²⁺, H₄N⁺, Et₃NH⁺, Me₄N⁺, (HOCH₂CH₂)₃NH⁺, or a cationic form of ethylenediamine, piperazine, and trishydroxymethyl aminomethane (TRIS).

An example of a general method for the preparation of the compounds of the present invention is provided in the following. The method comprises the following steps:

1) Providing a compound (1) of the following structure:

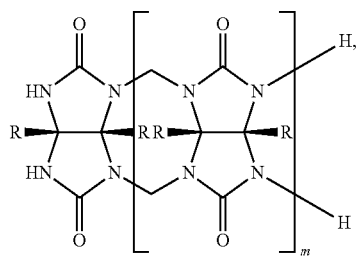

(1)

where m is from 0 to 4,

2) Forming a reaction mixture comprising compound (1), an acid (e.g., MeSO₃H, HCl, CF₃CO₂H, H₂SO₄, or TsOH) and a compound (2) having the following structure:

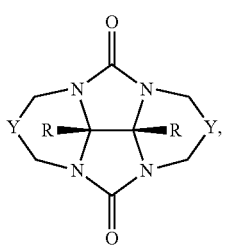

(2)

where each R is independently hydrogen, $C_1$ to $C_{20}$ alkyl group, $C_3$ to $C_{20}$ carbocyclic group, $C_1$ to $C_{20}$ heterocyclic group, carboxylic acid group, ester group, amide group, hydroxyl group or ether group. Optionally, adjacent R groups form a $C_3$ to $C_{20}$ carbocyclic ring or heterocyclic ring, where the carbocyclic ring is a ring in which all of the atoms forming the ring(s) are carbon atoms and the heterocyclic ring is a ring where at least one of the atoms forming the ring(s) is a heteroatom (e.g., oxygen, nitrogen, sulfur, etc.). These rings may each be substituted with alkyl groups and other substituents such as, for example, nitro, cyano, keto, carboxy, alkoxy, hydroxyl, amine, amide, halide (e.g., bromide, chloride, fluoride, and iodide), and alkoxy groups.

Y is oxygen or nitrogen substituted with a $C_1$ to $C_{20}$ alkyl group. (2) is added to the reaction mixture such that a compound (3), of the following structure is formed:

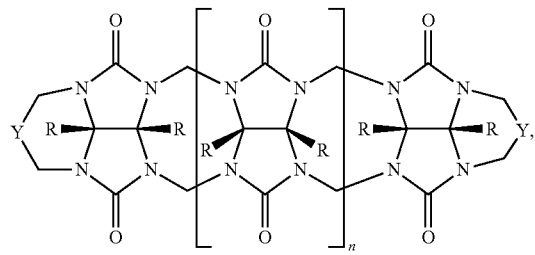
(3)

3) Contacting said compound (3) with TFA and

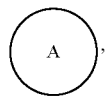

which can be a $C_5$ to $C_{20}$ carbocyclic ring system or $C_2$ to $C_{20}$ heterocyclic ring system, where the ring system comprises one or more rings. The ring system, optionally, has at least one solubilizing group. Optionally, the ring system has a targeting group. Compound (3), a solvent, and

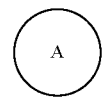

are combined such that the following structure is formed:

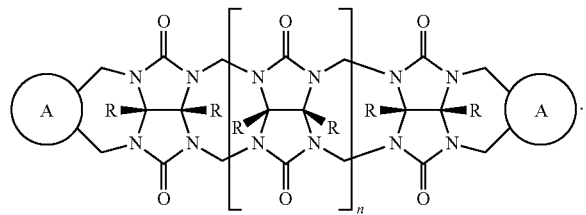

In an embodiment,

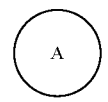

can be derivatized with the solubilizing group and/or targeting group after step 3). For example, one of the building block compounds can be derivatized to form a compound of the present invention. For example, an alkyl bromide component of one of the building block compounds can be reacted with a PEGylated thiol to make a compound with a PEG solubilizing group.

Examples of

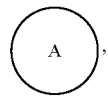

include but are not limited to:

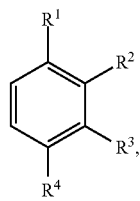
(4)

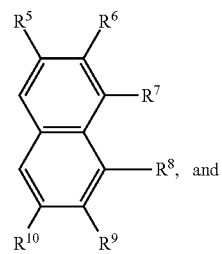
(5)

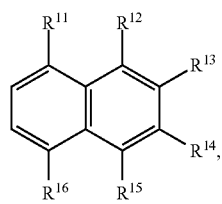
(6)

where each $R^1$ to $R^{16}$ is independently hydrogen, $C_1$ to $C_{20}$ alkyl group, halo group, hydroxyl group, nitro group, carboxylic acid group, ester group, amide group, ether group, $C_3$ to $C_{20}$ carbocyclic group, or $C_1$ to $C_{20}$ heterocyclic group. For example, the carboxylic acid group, ester group, amide group, and ether groups can have from 1 to 20 carbons, including all integer values and ranges therebetween. At least one of the $R^1$ to $R^{16}$ groups in the structure has the following structure:

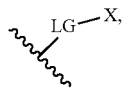

where LG is the linking group and wherein X is the solubilizing group. In an embodiment, LG can have the formula:

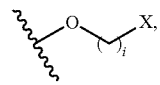

where each i is 1 to 20. Optionally one or more adjacent $R^1$ to $R^{16}$ groups are connected forming a carbocyclic or heterocyclic ring, and the ring can be substituted or unsubstituted. In an embodiment, at least one of the $R^1$ to $R^{16}$ groups in the structure has the following structure:

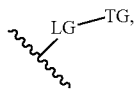

where LG is a linking group and wherein TG is the targeting group.

It is desirable for the

Ⓐ group to be reactive in electrophilic aromatic substitution reactions. Thus, in an embodiment, the

Ⓐ group is an aromatic ring having at least one alkyl ether moiety.

The determination of suitable reaction conditions (e.g., solvent, reaction time and reaction temperature) is within the purview of one having skill in the art. A wide range of solvent can be used. Examples of suitable solvents include TFA, HCl, $H_2SO_4$, TsOH, HBr, $MeSO_3H$, and mixtures thereof. For example, it may be desirable to add acetic anhydride as a co-solvent. Reaction time can vary. Generally, a reaction time of 3 hours is sufficient to provide a desired extent of reaction. A wide range of reaction temperatures can be used. For example, reaction temperatures of 25° C. to 100° C. can be used.

In an embodiment, the compounds can be made from building block compounds (i.e., intermediates). The building block compounds have functional groups (e.g., halogen (e.g., fluoro, chloro, bromo, or iodo), hydroxy, carboxylic acid, alkenyl, alkynyl, nitro, cyano, keto, amino, amido, thioether, thioate and triazole groups) that can be reacted to form solubilizing groups or targeting groups. Examples of building block compounds include:

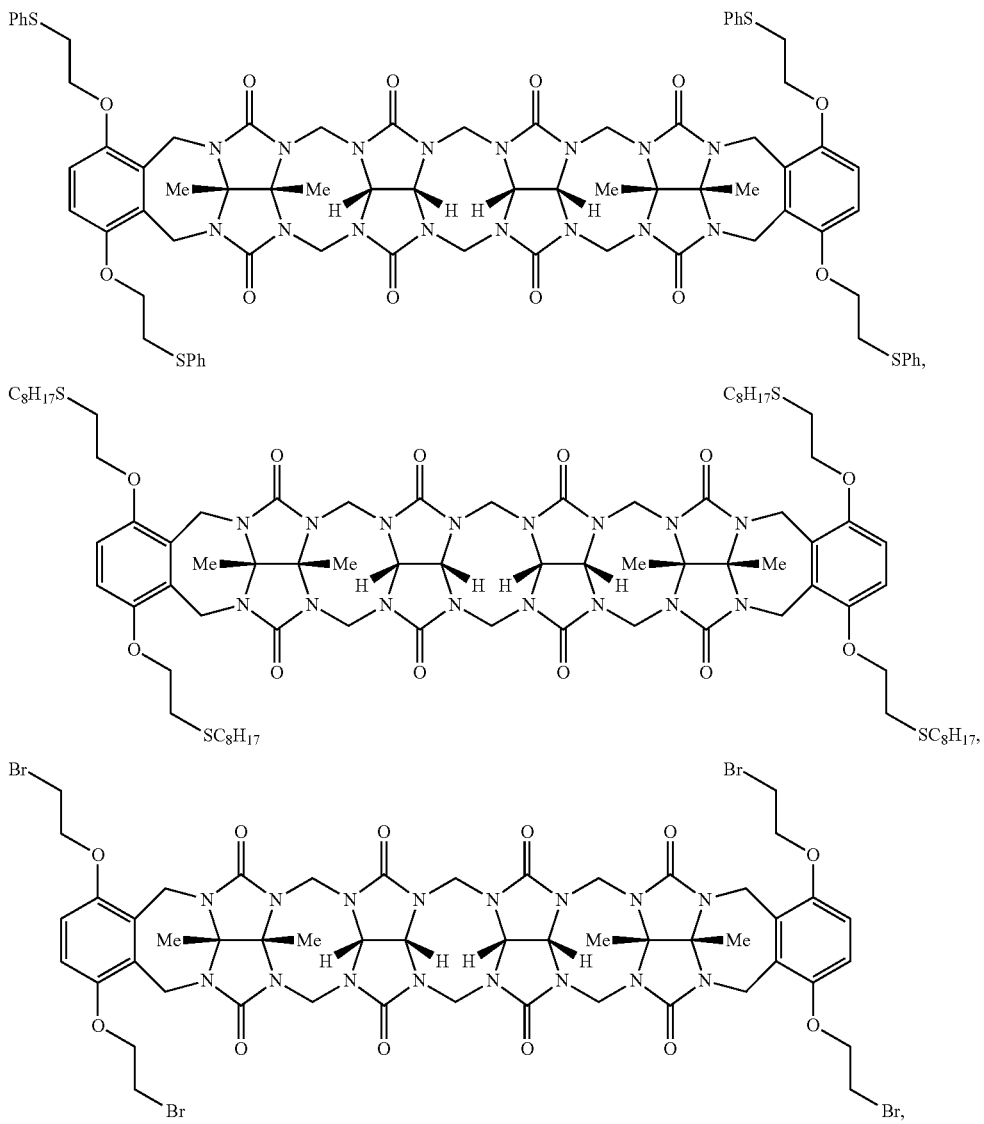

-continued
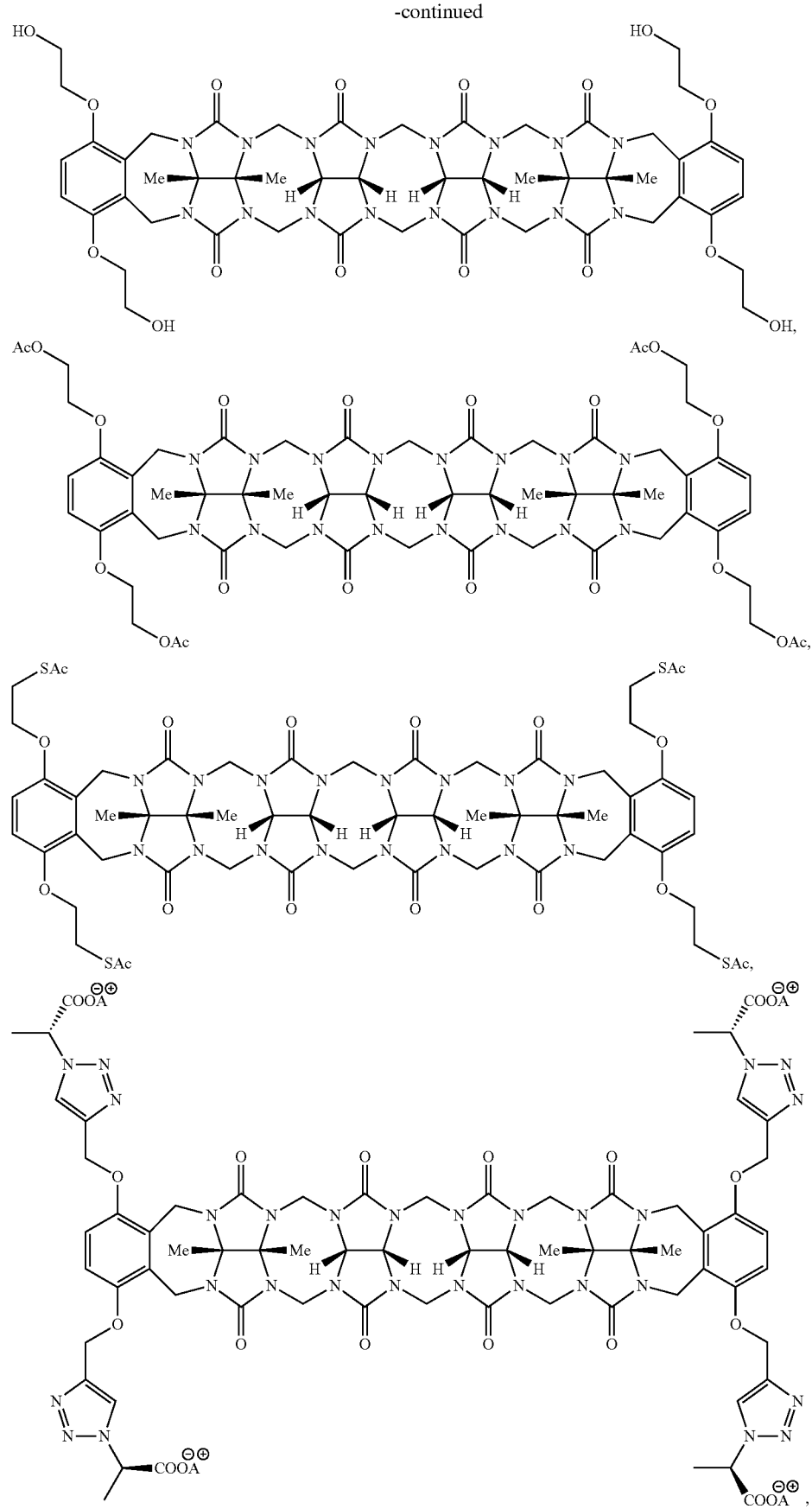

-continued

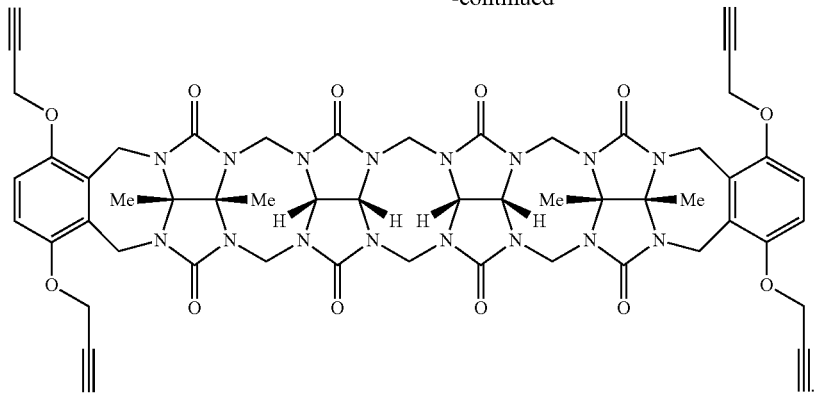

For example, the tetra propargyl compound can be reacted with azides to form for example a triazole compound.

The following examples are presented to illustrate the present invention. They are not intended to be limiting in any manner.

EXAMPLE 1

General Experimental. Starting materials were purchased from commercial suppliers and were used without further purification or were prepared by literature procedures. Melting points were measured on a Meltemp apparatus in open capillary tubes and are uncorrected. IR spectra were recorded on a JASCO FT/IR 4100 spectrometer and are reported in $cm^{-1}$. NMR spectra were measured on Bruker DRX-400 instrument operating at 400 MHz for $^1$H and 100 MHz for $^{13}$C. Mass spectrometry was performed using a JEOL AccuTOF electrospray instrument (ESI). UV-Vis absorbance was measured on Varian Cary 100 UV spectrophotometer.

Synthetic Procedures and Characterization. Glycoluril Dimer. A mixture of glycoluril (500 g, 3.51 mol) and paraformaldehyde (105 g, 3.51 mol) in HCl (8 M, 70 mL) was heated at 50° C. for 48 h. The reaction mixture was cooled and filtered. The solid was washed with water (500 mL) and then recrystallized with TFA (1.5 L) to yield Glycoluril Dimer as a white solid (334 g, 62%).

Dimethyl glycoluril. Into a solution of urea (1140 g, 19.0 mol) in HCl (0.3 M, 2.8 L), 2,3-butanedione (500 g, 5.8 mol) was added. The solution was stirred at RT for 12 h. The reaction mixture was filtered and the solid was washed with water (2.0 L×2) and then ethanol (2.0 L) to yield Dimethyl glycoluril as a white solid (749 g, 76%).

Dimethyl glycoluril bis(cyclic ether). A mixture of Dimethyl glycoluril (749 g, 4.4 mol) and paraformaldehyde (650 g, 21.7 mol) in HCl (9 M, 3.8 L) was stirred for 24 h. Water (14.0 L) was added and the mixture was stirred for an additional 12 h. The mixture was then filtered and washed with water (2 L) and ethanol (2 L) to yield Dimethyl glycoluril bis(cyclic ether) as a white solid (719 g, 65%).

Methyl tetramer. (FIG. 1) Into a solution of Glycoluril Dimer (84 g, 0.27 mol) in anhydrous $MeSO_3H$ (600 mL), Dimethyl glycoluril bis(cyclic ether) (304 g, 1.20 mol) was added. The mixture was stirred and heated at 50° C. for 3 h. The reaction mixture was poured into water (6.0 L). After filtration, the crude solid was dried in high vacuum. The crude solid was recrystallized from TFA (350 mL) and water (1.4 L) to yield Methyl tetramer as a white solid (76 g, 36%).

Propanesulfonate wall. Into a solution of hydroquinone (100 g, 0.91 mol) in aqueous NaOH solution (2.5 M, 1.4 L), a solution of propanesultone (275 g, 2.25 mol) in 1, 4-dioxane (1.8 L) was added. The mixture was stirred at RT for 12 h. The mixture was filtered. The solid was washed with acetone (2 L×2) to yield 3,3'-(1,4-phenylenebis(oxy))bis (propane-1-sulfonic acid) as white solid (294 g, 81%).

Motor1. (FIG. 1) Into a solution of methyl tetramer (76 g, 97 mmol) in TFA (700 mL), propanesulfonate wall (154 g, 387 mmol) was added. The mixture was stirred and heated at 70° C. for 3 h. The solvent was removed by rotary evaporation and the solid was dried in high vacuum. The solid was washed with the mixture of water and acetone (1:2, v/v, 1.5 L×2). The solid was dissolved in water (500 mL) and adjusted to pH=7 by adding 1 M aqueous NaOH. The solvent was removed with rotary evaporation and then the solid was further dried under high vacuum to yield Motor1 as a white solid (60 g, 40%). M.p.>320° C. (decomposed). IR (ATR, cm-1): 3000 w, 1711 s, 1456 s, 1313 m, 1225 s, 1178 s, 1076 s, 972 m, 920 m, 822 m, 797 s, 756 m, 665 m. $^1$H NMR (400 MHz, $D_2O$): 6.72 (s, 4H), 5.50 (d, J=15.2, 2H), 5.38 (d, J=15.7, 4H), 5.31 (d, J=9.0, 2H), 5.25 (d, J=8.9, 2H), 5.19 (d, J=16.2, 4H), 4.10 (d, J=11.1, 4H), 4.06 (d, J=11.7, 4H), 3.97 (d, J=15.4, 2H), 3.91 (m, 4H), 3.79 (m, 4H), 2.98 (m, 8H), 2.06 (m, 8H), 1.64 (m, 6H), 1.61 (s, 6H). $^{13}$C NMR (100 MHz, $D_2O$, 1, 4-dioxane as internal reference): δ 157.5, 157.3, 150.8, 128.3, 115.3, 79.7, 78.6, 72.3, 72.1, 69.2, 53.8, 49.4, 49.0, 35.9, 25.5, 17.1, 16.0. MS (ESI): m/z 1473.3232 ([M−H]⁻), calculated 1473.3216.

Figure 2:
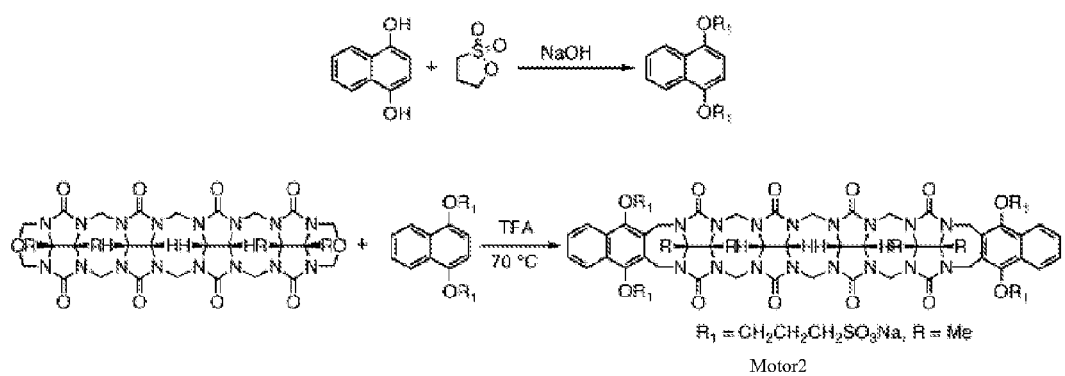

1,4-Naphthalene propanesulfonate wall (FIG. 2). Into a solution of 1,4-dihydroxynaphathelene (2.0 g, 12.5 mmol) in NaOH (10 wt %, 16 mL), a solution of propanesultone (3.8 g, 31.2 mmol) in 1,4-dioxane (24 mL) was added. This solution was stirred at RT for 12 h. After filtration, the solid was dissolved in H2O (10 mL) and then precipitated with MeCN (60 mL) to yield a blue solid (1.5 g, 3.3 mmol, 27%). M.p.>227° C. (dec.). IR (ATR, $cm^{-1}$): 2988 w, 2902 w, 1597 w, 1462 w, 1377 w, 1273 m, 1240 m, 1222 m, 1183 s, 1155 m, 1100 m, 946 s, 800 w, 765 m, 613 m. $^1$H NMR (600 MHz, D2O): 8.01 (m, 2H), 7.43 (m, 2H), 6.63 (s, 2H), 4.02 (t, 4H), 3.02 (t, 4H), 2.16 (m, 4H). $^{13}$C NMR (125 MHz, $D_2O$, 1,4-dioxane as internal reference): δ 148.0, 126.4, 125.9, 121.4, 106.3, 67.5, 48.1, 24.2. High-Res MS (ESI): m/z 427.0528 ([M+Na]⁺), calculated 427.0497.

Motor2 (FIG. 2). To a solution of methyl tetramer (2.67 g, 3.42 mmol) in TFA (25 mL), 1,4-Naphthalene propanesulfonate wall (6.13 g, 13.7 mmol) was added. This solution was stirred and heated at 70° C. for 3 h. The solvent was removed with rotary evaporation and the solid was dried in high vacuum. The crude mixture was refluxed in EtOH (60 mL) overnight and then filtered. The solid was dissolved in hot water (20 mL). The solution was adjusted to pH=7 with 1 M NaOH. The solution was cooled down to RT and filtered to yield Motor2 as a white solid (1.7 g, 30%). M.p.>196° C. (decomposed). IR (ATR, cm$^{-1}$): 3433 w, 1717 s, 1471 s, 1425 m, 1383 m, 1349 m, 1317 m, 1179 s, 1082 s, 1036 s, 922 w, 881 w, 827 m, 801 s, 757 m, 728 m, 676 m. $^1$H NMR (600 MHz, D$_2$O): 7.72 (m, 4H), 7.27 (m, 4H), 5.48 (d, J=15.3, 2H), 5.42 (d, J=15.7, 4H), 5.31 (d, J=8.9, 2H), 5.25 (d, J=8.9, 2H), 5.12 (d, J=16.0, 4H), 4.30 (d, J=16.0, 4H), 4.12 (d, J=15.7, 4H), 4.00 (m, 4H), 3.96 (d, J=15.3, 2H), 3.74 (m, 4H), 3.08 (m, 8H), 2.13 (m, 8H), 1.66 (s, 6H), 1.61 (s, 6H). $^{13}$C NMR (125 MHz, D$_2$O, 1,4-dioxane as internal reference): δ 156.7, 156.3, 148.2, 127.7, 127.0, 126.1, 122.3, 78.6, 77.6, 74.1, 71.5, 71.2, 52.9, 48.5, 36.5, 25.1, 16.4, 15.2. High-Res MS (ESI): m/z 777.1986 ([M+2H]$^{2+}$), calculated 777.1972.

EXAMPLE 2

Figure 3:
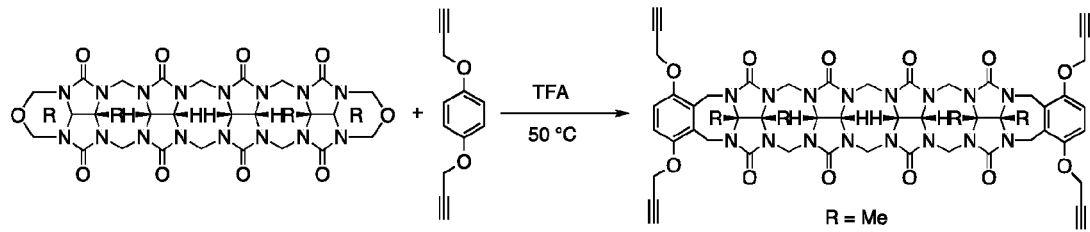

Propargyl Host (FIG. 3). Methyl tetramer (1.70 g, 2.18 mol) in TFA (5 mL), 1,4-bis(prop-2-yn-1-yloxy)benzene (1.62 g, 8.71 mmol) was added. The solution was heated at 50° C. for 4 h. The solvent was removed with rotary evaporation. The crude product was further dried on high vacuum and then washed with water (50 mL). The solid was washed with acetone (50 mL×2) and filtered. Then this solid was dissolved in concentrated HCl (50 mL) and then precipitated by adding water (100 mL) to yield a white solid (1.1 g, 1.0 mmol, 45%). M.P.>260° C. (decomposed). IR (ATR, cm$^{-1}$): 2939 w, 1721 m, 1463 m, 1380 m, 1314 w, 1231 m, 1211 m, 1186 m, 1090 m, 941 s, 848 w, 796 m, 758 m, 616 m. $^1$H NMR (400 MHz, D$_2$O): 6.92 (s, 4H), 5.54 (d, J=14.9, 2H), 5.45 (d, J=15.0, 4H), 5.34 (d, J=9.0, 2H), 5.23 (d, J=9.0, 2H), 5.15 (d, J=15.8, 4H), 4.79 (d, J=15.0, 4H), 4.72 (d, J=15.0, 4H), 4.10 (d, J=15.8, 4H), 4.03 (d, J=15.0, 4H), 4.03 (d, J=14.9, 2H), 3.52 (s, 4H), 1.65 (s, 6H), 1.61 (s, 6H). $^{13}$C NMR (125 MHz, DMSO-d$^6$): δ 156.6, 155.2, 150.7, 129.6, 115.6, 81.3, 79.1, 78.5, 77.5, 71.9, 71.5, 59.0, 54.2, 49.4, 35.6, 18.0, 16.9. HR-MS (ESI): m/z 1117.4007 ([M+H]$^+$), calculated 1117.4029.

Figure 4:
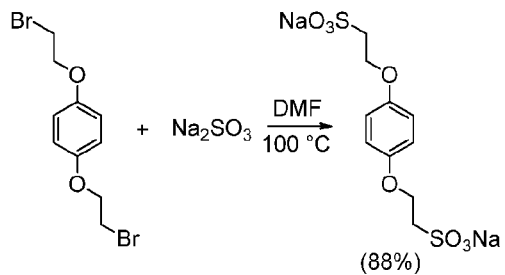

Ethanesulfonate Wall (FIG. 4). 1,4-bis(2-bromoethoxy)benzene (2.00 g, 6.13 mmol) and sodium sulfite (3.10 g, 24.5 mmol) were mixed and dissolved in DMF (20 mL). The mixture was stirred at 100° C. under N$_2$ for 12 h and then water (20 mL) was added. The mixture was allowed to cool to RT and the product precipitated as white crystals. The solid was collected by filtration and then purified by recrystallization from water. Drying under high vacuum gave Sodium 2,2'-(1,4-phenylenebis(oxy))diethanesulfonate as a white solid (2.01 g, 88%). $^1$H NMR (400 MHz, D$_2$O): 7.03 (s, 4H), 4.39 (t, J=6.2, 4H), 3.36 (t, J=6.2, 4H). $^{13}$C NMR (125 MHz, D$_2$O, 1,4-dioxane as internal reference): δ 151.5, 115.5, 63.3, 49.3.

Figure 5:
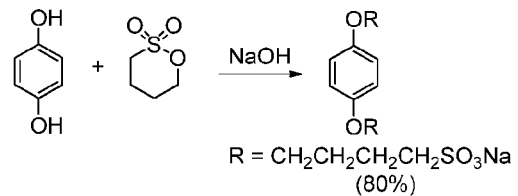

Butanesulfonate Wall (FIG. 5). A solution of butanesultone (24.5 g, 200 mmol) in 1,4-dioxane (160 mL) was added into a solution of hydroquinone (8.80 g, 80.0 mmol) in aqueous NaOH solution (10 wt %, 120 mL). The mixture was stirred at RT for 12 h then filtered to collect the crude solid. The solid was stirred with acetone (200 mL) then dried under high vacuum to yield Sodium 4,4'-(1,4-phenylenebis(oxy))dibutane-1-sulfonate as a white solid (25.1 g, 80%). $^1$H NMR (400 MHz, D$_2$O): 7.02 (s, 4H), 4.09 (t, J=5.7, 4H), 2.99 (t, J=7.4, 4H), 1.85-2.00 (m, 8H). $^{13}$C NMR (125 MHz, D$_2$O, 1,4-dioxane as internal reference): δ 152.1, 115.8, 68.3, 50.2, 26.8, 20.4.

Figure 6:
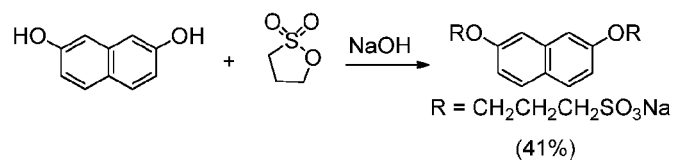

2,7-Naphthalenesulfonate Wall (FIG. 6). A solution of propanesultone (38.0 g, 300 mmol) in 1,4-dioxane (240 mL) was added into a solution of naphthalene-2,7-diol (20.0 g, 124 mmol) in NaOH (10 wt %, 160 mL). This solution was stirred at RT for 12 h. After filtration, the solid was collected and then dissolved in H$_2$O (100 mL) and then was precipitated by the addition of CH$_3$CN (600 mL). The solid was collected by filtration and then dried under high vacuum to yield a pale green solid (23.2 g, 41%). $^1$H NMR (400 MHz, D$_2$O): 7.77 (d, J=8.9, 2H), 7.23 (m, 2H), 7.07 (dd, J=8.9, 2.4, 2H), 4.24 (t, J=6.4, 4H), 3.05-3.15 (m, 4H), 2.15-2.30 (m, 4H). $^{13}$C NMR (125 MHz, D$_2$O, 1,4-dioxane as internal reference): δ 156.2, 135.0, 128.9, 123.9, 115.8, 106.3, 66.0, 47.4, 23.7.

Figure 7:
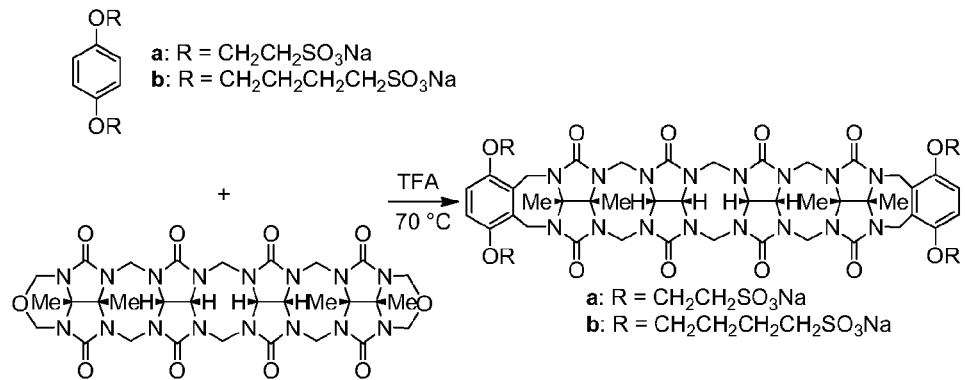

Ethanesulfonate Host a (FIG. 7). Sodium 2,2'-(1,4-phenylenebis(oxy))diethanesulfonate (1.81 g, 0.23 mmol) was added into a solution of methyl tetramer (0.64 g, 0.77 mmol) in TFA (2 mL). The mixture was stirred and heated at 70° C. for 4 h. The solvent was removed with under reduced pressure and the solid was further dried under high vacuum. The solid was washed with the mixture of water and acetone (1:2, v/v, 30 mL) twice and then dissolved in water and adjusted to pH=7 by adding 1 M aqueous NaOH. The solvent was removed under reduced pressure and then the solid was further dried under high vacuum to yield product a as a white solid (0.72 g, 61%). $^1$H NMR (400 MHz, D$_2$O): 6.94 (s, 4H), 5.67 (d, J=15.5, 2H), 5.56 (d, J=16.0, 4H), 5.44 (d, J=7.6, 2H), 5.38 (d, J=7.6, 2H), 5.35 (d, J=16.3, 4H) 4.45-4.25 (m, 8H), 4.24 (d, J=16.0, 4H), 4.21 (d, J=16.3, 4H) 4.10 (d, J=15.5, 2H), 3.55-3.40 (m, 4H), 3.35-3.20 (m, 4H), 1.79 (s, 6H), 1.75 (s, 6H). $^{13}$C NMR (125 MHz, D$_2$O, 1,4-dioxane as internal reference): δ 156.4, 155.9, 149.6, 127.8, 114.4, 78.4, 77.1, 70.9, 70.8, 65.2, 52.2, 50.1, 48.0, 34.8, 15.6, 14.6.

Butanesulfonate Host b (FIG. 7). Sodium 4,4'-(1,4-phenylenebis(oxy))bis(butane-1-sulfonate) (6.50 g, 15.4 mmol) was added into a solution of methyl tetramer (3.00 g, 3.84 mmol) in TFA (30 mL). The mixture was stirred and heated at 70° C. for 4 h. The solvent was removed under reduced pressure and the solid was further dried under high vacuum. The solid was washed twice with the mixture of water and acetone (1:2, v/v, 300 mL) and then dissolved in water and adjusted to pH=7 by adding 1 M aqueous NaOH. The solvent was removed under reduced pressure and then the solid was further dried under high vacuum to yield product b as a white solid (2.33 g, 40%). $^1$H NMR (400 MHz, D$_2$O): 7.01 (s, 4H), 5.62 (d, J=15.2, 2H), 5.51 (d, J=16.0, 4H), 5.45 (d, J=8.9, 2H), 5.35 (d, J=8.9, 2H), 5.24 (d, J=16.0, 4H), 4.30 (d, J=16.0, 4H), 4.25 (d, J=16.0, 4H), 4.04 (d, J=15.2, 2H), 3.90-3.75 (m, 8H), 2.90-2.75 (m, 4H), 2.70-2.55 (m, 4H), 1.79 (s, 12H), 1.79-1.30 (m, 16H).

Figure 8:
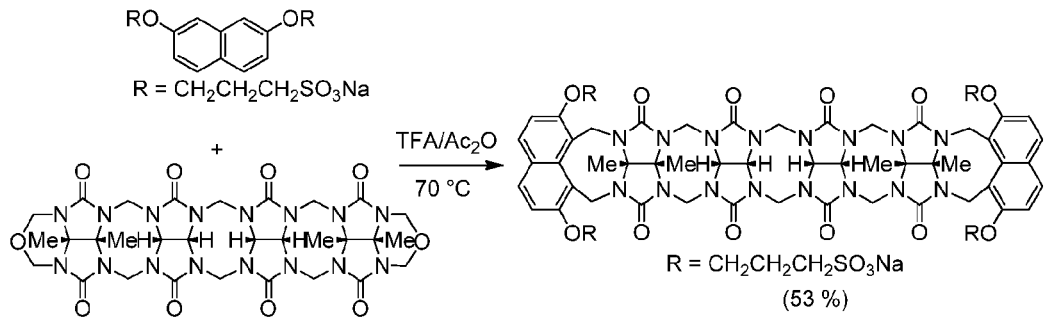

Naphthalene propanesulfonate Host (FIG. 8). Sodium 3,3'-(naphthalene-2,7-diylbis(oxy))dipropane-1-sulfonate (229 mg, 0.152 mmol) was added into a solution of methyl tetramer (100 mg, 0.128 mmol) in a mixture of TFA/Ac$_2$O (1:1, 2 mL). The mixture was stirred and heated at 70° C. for 3 h and then was poured into acetone (30 mL). The solid was collected with filtration. The crude solid was dissolved in H$_2$O (10 mL), and then precipitated by the addition of acetone (30 mL). The product was then collected by filtration and then recrystallized from water and acetone (1:1, v/v, 5 mL). The purified product was obtained as a pale beige solid after drying under high vacuum (112 mg, 53%). $^1$H NMR (400 MHz, D$_2$O): 6.95 (d, J=8.9, 4H), 6.48 (d, J=8.9, 4H), 5.60 (d, J=16.3, 4H), 5.58 (d, J=15.4, 6H), 5.30 (d, J=9.0, 2H), 5.20 (d, J=9.0, 2H), 4.72 (d, J=16.3, 4H), 4.16 (d, J=15.4, 4H), 4.00-3.85 (m, 8H), 3.30-3.05 (m, 8H), 2.35-2.10 (m, 8H), 1.76 (s, 12H). $^{13}$C NMR (125 MHz, D$_2$O, 1,4-dioxane as internal reference): δ 156.4, 156.1, 155.0, 131.6, 127.3, 116.3, 112.6, 76.8, 75.4, 70.8, 68.1, 52.2, 48.0, 47.9, 33.1, 29.7, 24.4, 16.6, 15.2, (only 19 out of the expected resonances were observed).

Figure 9:
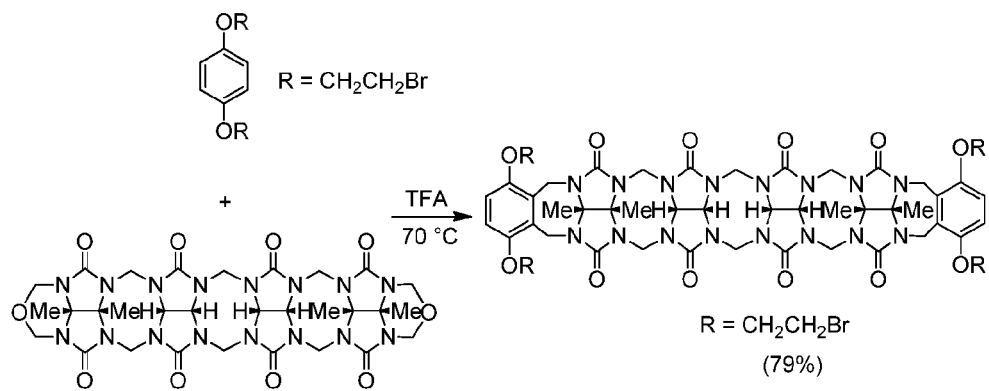

Tetrabromo Host (FIG. 9). 1,4-bis(2-bromoethoxy)benzene (1.70 g, 5.21 mmol) and methyl tetramer (1.20 g, 1.53 mmol) were mixed in a round bottom flask. TFA (12 mL) was added, and the mixture was stirred at 70° C. for 3 h. The reaction mixture was poured into MeOH (100 mL), and the solid was collected by filtration. The crude product was stirred with water (150 mL) and then acetone (150 mL) at RT and the solid was isolated by filtration. Drying at high vacuum gave the product as a white powder (1.71 g, 79%). M.p. 283-285° C. IR (ATR, cm$^{-1}$): 3000 br, 1704 m, 1456 m, 1311 m, 1225 s, 1177 s, 1080 s, 966 m, 922 m, 818 m, 794 s, 754 m, 666 m. $^1$H NMR (400 MHz, DMSO): 6.91 (s, 4H), 5.59 (d, J=14.4, 2H), 5.51 (d, J=15.2, 4H), 5.38 (d, J=9.0, 2H), 5.30-5.25 (m, 6H), 4.50-4.40 (m, 4H), 4.25-4.20 (m, 10H), 4.06 (d, J=15.2, 4H), 3.90-3.80 (m, 8H), 1.69 (s, 6H), 1.66 (s, 6H). $^{13}$C NMR (125 MHz, DMSO, 1,4-dioxane as internal reference): δ 156.0, 154.6, 151.0, 129.5, 116.7, 78.0, 76.8, 71.5, 71.4, 71.0, 53.6, 48.9, 35.2, 33.5, 17.2, 16.3.

Figure 10:
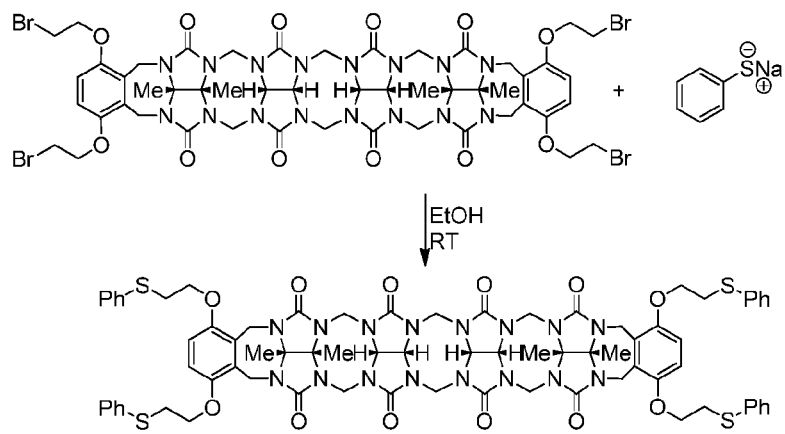

Tetrathiophenyl Host (FIG. 10). Sodium benzenethiolate (48 mg, 0.36 mmol) was dissolved in EtOH (2 mL). Tetrabromohost (100 mg, 0.072 mmol) was added and the reaction mixture was stirred at RT for 12 h. The reaction mixture was centrifuged to collect the crude product. The solid was washed with EtOH (10 mL) and then H$_2$O (10 mL). A pale yellow solid was obtained after drying under high vacuum (63 mg, 58%). $^1$H NMR (400 MHz, DMSO): 7.45-7.05 (m, 20H), 6.68 (s, 4H), 5.62 (d, J=15.3, 2H), 5.51 (d, J=14.8, 4H), 5.39 (d, J=8.0, 2H), 5.27 (d, J=8.0, 2H), 5.24 (d, J=15.7, 4H), 4.25-4.10 (m, 4H), 4.10-3.85 (m, 14H), 3.45-3.30 (m, 8H), 1.69 (s, 6H), 1.63 (s, 6H).

Figure 11:
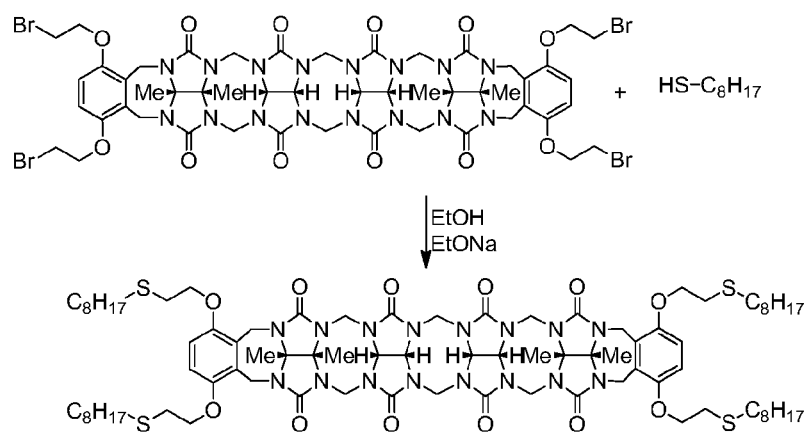

Tetra Octanethioether Host (FIG. 11). Octane-1-thiol (53 mg, 0.36 mmol) was dissolved in EtOH (2 mL). Tetrabromohost (100 mg, 0.072 mmol) was added and the reaction mixture was stirred at RT for 3 h. The reaction mixture was centrifuged to collect crude solid. The solid was washed with EtOH (10 mL) and then H$_2$O (10 mL). A white solid was obtained after drying under high vacuum (103 mg, 72%). $^1$H NMR (400 MHz, DMSO): 6.82 (s, 4H), 5.59 (d, J=12.2, 2H), 5.48 (d, J=14.8, 4H), 5.35 (d, J=8.6, 2H), 5.24 (d, J=8.6, 2H), 5.24 (d, J=16.4, 4H), 4.25-4.20 (m, 4H), 4.08 (d, J=16.4, 4H), 4.04 (d, J=14.8, 4H), 4.10-4.00 (m, 4H), 3.99 (d, J=12.2, 2H), 2.88 (t, J=5.6, 8H), 2.63 (t, J=7.2, 8H), 1.66 (s, 6H), 1.62 (s, 6H), 1.56 (m, 8H), 1.40-1.15 (m, 40H), 0.83 (t, J=7.2, 12H).

Figure 12:
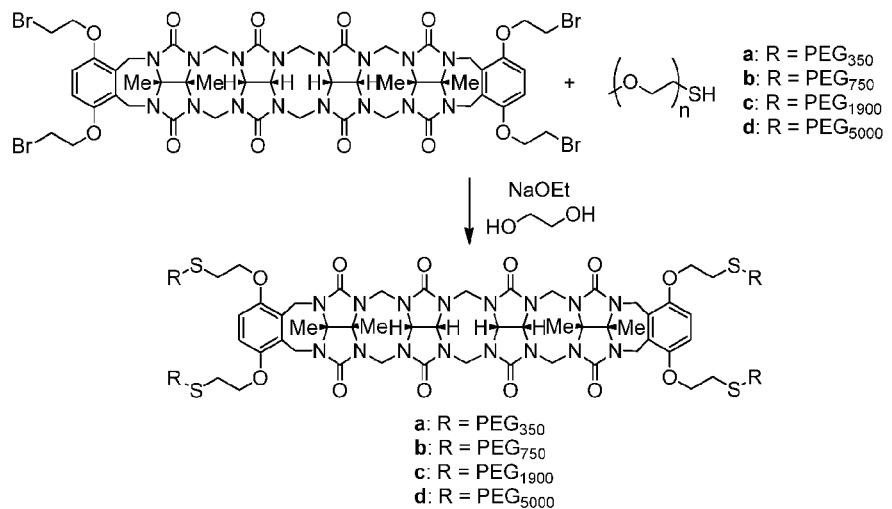

PEG 350 Host (FIG. 12). PEG 350 (176 mg, 0.43 mmol) and NaOEt (29 mg, 0.43 mmol) was dissolved in ethylene glycol (2 mL). Tetrabromo Host (100 mg, 0.072 mmol) was added and the reaction mixture was stirred and heated at 50° C. for 12 h. The reaction mixture was centrifuged to remove insoluble material and the clear solution was concentrated and poured into diethyl ether (10 mL). The white precipitate was collected by centrifugation. A dark yellow gel was obtained after drying under high vacuum (150 mg, 82%). $^1$H NMR (400 MHz, D$_2$O): 6.64 (s, 4H), 5.64 (d, J=16.0, 4H), 5.60-5.35 (m, 8H), 5.34 (d, J=8.4, 2H), 4.35 (d, J=16.0, 4H), 4.20-4.10 (m, 12H), 4.05, (d, J=12.3, 2H), 3.95-3.55 (m, 160H), 3.38 (s, 12H), 3.11 (t, J=6.0, 8H), 2.96 (t, J=6.0, 8H), 1.89 (s, 6H), 1.86 (s, 6H).

PEG 750 Host (FIG. 12). PEG 750 (349 mg, 0.43 mmol) and NaOEt (29 mg, 0.43 mmol) was dissolved in ethylene glycol (2 mL). Tetrabromo Host (100 mg, 0.072 mmol) was added and the reaction mixture was stirred and heated at 70° C. for 12 h. The reaction mixture was centrifuged to remove insoluble material and a mixture of CH$_2$Cl$_2$ and MeOH (5 mL, 4:1) was added to the supernatant. Diethyl ether (10 mL) was added and then the mixture was centrifuged to isolate a white precipitate. A pale yellow solid was obtained after drying under high vacuum (172 mg, 58%). $^1$H NMR (400 MHz, D$_2$O): 7.03 (s, 4H), 5.68 (d, J=16.2, 2H), 5.56 (d, J=15.6, 4H), 5.45-5.25 (m, 8H), 4.30-4.00 (m, 18H), 3.95-3.55 (m, 320H), 3.32 (s, 12H), 3.00-2.75 (m, 8H), 2.65 (t, J=6.0, 8H), 1.76 (s, 6H), 1.72 (s, 6H).

PEG 1900 Host (FIG. 12). PEG 1900 (823 mg, 0.43 mmol) and NaOEt (29 mg, 0.43 mmol) was dissolved in ethylene glycol (2 mL). Tetrabromo Host (100 mg, 0.072 mmol) was added and the reaction mixture was stirred and heated at 70° C. for 12 h. The reaction mixture was centrifuged to remove insoluble material and a mixture of CH$_2$Cl$_2$ and MeOH (5 mL, 4:1) was added to the supernatant. Diethyl ether (10 mL) was added and then the mixture was centrifuged to isolate a white precipitate. The product was further purified by GPC using Sephadex-G25. A pale yellow solid was obtained after drying under high vacuum (213 mg, 34%). $^1$H NMR (400 MHz, D$_2$O): 6.49 (s, 4H), 5.46 (d, J=16.4, 4H), 5.40-5.20 (m, 8H), 5.19 (d, J=8.4, 2H), 4.15 (d, J=16.0, 4H), 4.10-3.85 (m, 16H), 3.95-3.55 (m, 800H), 3.22 (s, 12H), 2.96 (t, J=6.2, 8H), 2.81 (t, J=6.2, 8H), 1.73 (s, 6H), 1.71 (s, 6H).

PEG 5000 Host (FIG. 12). PEG 5000 (2.16 g, 0.43 mmol) and NaOEt (29 mg, 0.43 mmol) was dissolved in ethylene glycol (4 mL). Tetrabromo Host (100 mg, 0.072 mmol) was added and the reaction mixture was stirred and heated at 70° C. for 12 h. The reaction mixture was centrifuged to remove insoluble material and a mixture of CH$_2$Cl$_2$ and MeOH (5 mL, 4:1) was added to the supernatant. Diethyl ether (10 mL) was added and then the mixture was centrifuged to isolate a white precipitate. The product was further purified by GPC using Sephadex-G25. A pale yellow solid was obtained after drying under high vacuum (351 mg, 23%). $^1$H NMR (400 MHz, D$_2$O): 7.05 (s, 4H), 5.71 (d, J=15.5, 2H), 5.62 (d, J=15.6, 4H), 5.60-5.25 (m, 8H), 4.30-4.00 (m, 18H), 3.95-3.55 (m, 1840H), 3.32 (s, 12H), 3.00-2.75 (m, 8H), 2.66 (t, J=6.0, 8H), 1.76 (s, 6H), 1.74 (s, 6H).

Figure 13:
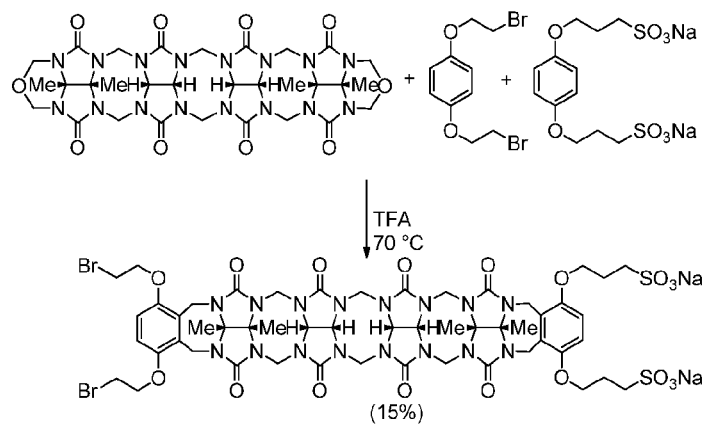

Dibromo dipropanesulfonate Host (FIG. 13). 1,4-bis(2-bromoethoxy)benzene (250 mg, 0.768 mmol) and sodium 3,3'-(1,4-phenylenebis(oxy))bis(propane-1-sulfonate) (102 mg, 0.256 mmol) were added into a solution of methyl tetramer (200 mg, 0.256 mmol) in TFA (2.5 mL). The mixture was stirred and heated at 70° C. for 3 h and then was poured into acetone (150 mL). The solid was collected by filtration. The crude solid was stirred with water (30 mL×3) at RT for 4 hr. The filtrate was collected and the solvent was removed under reduced pressure. The produce was purified by recrystallization from H$_2$O and MeOH (1:1, 15 mL). The product was obtained as a white solid after drying under high vacuum (112 mg, 53%). $^1$H NMR (400 MHz, D$_2$O): 6.97 (s, 2H), 6.72 (s, 2H), 5.62 (d, J=15.9, 2H), 5.60 (d, J=15.9, 2H), 5.53 (d, J=16.4, 2H), 5.45 (d, J=5.8, 2H), 5.43 (d, J=15.9, 2H), 5.40 (d, J=5.0, 2H), 5.21 (d, J=10.8, 2H), 4.27 (d, J=16.4, 2H), 4.25-4.20 (m, 8H), 4.15-4.05 (m, 8H), 3.95-3.75 (m, 4H), 3.45-3.35 (m, 2H), 3.25-3.20 (m, 2H), 3.14 (t, J=7.7, 4H), 2.35-2.15 (m, 4H), 1.87 (s, 3H), 1.81 (s, 3H), 1.67 (s, 3H), 1.66 (s, 3H).

Figure 14:
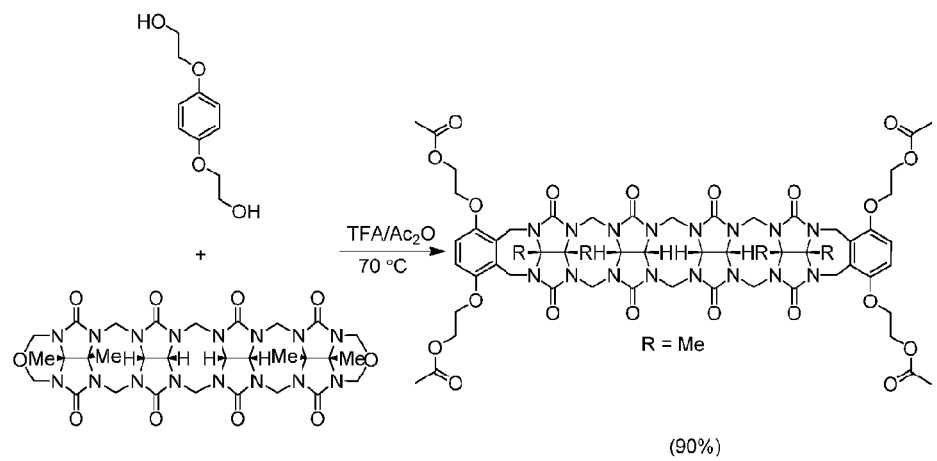

Tetra Ester Host (FIG. 14). 2,2'-(1,4-phenylenebis(oxy)) diethanol (1.02 g, 5.12 mmol) and methyl tetramer (1.00 g, 1.28 mmol) were mixed as solid and then dissolved in a mixture of TFA and Ac$_2$O (1:1, 10 mL). The mixture was stirred at 70° C. for 3.5 h and then was poured into MeOH (150 mL). The solid was collected by filtration and was washed with acetone (100 mL) and water (100 mL). After drying under high vacuum, the product was obtained as a white powder (1.51 g, 90%). M.p.>300° C. IR (ATR, cm$^{-1}$): 3000 w, 1711 s, 1456 s, 1313 m, 1225 s, 1178 s, 1076 s. $^1$H NMR (400 MHz, DMSO): 6.85 (s, 4H), 5.58 (d, J=16.3, 2H), 5.48 (d, J=15.6, 4H), 5.37 (d, J=9.0, 2H), 5.27 (d, J=9.0, 2H), 5.23 (d, J=16.0, 4H), 4.45-4.30 (m, 4H), 4.30-4.05 (m, 14H), 3.50-3.45 (m, 8H), 2.06 (s, 12H), 1.76 (s, 12H).

Figure 15:
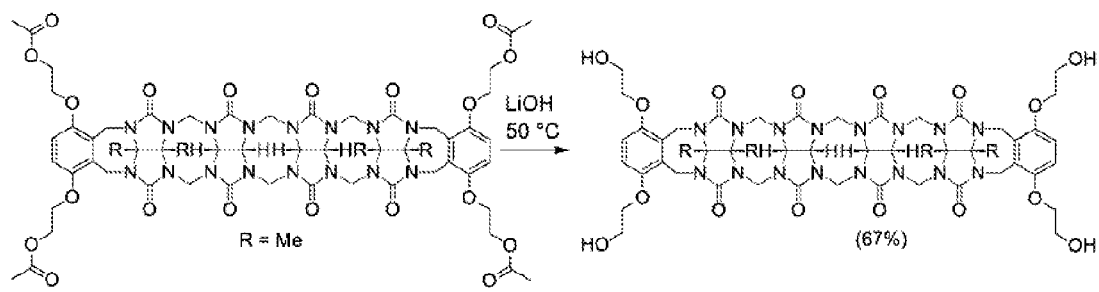

Tetra Hydroxy Host (FIG. 15). Tetra Ester Host (0.400 g, 0.305 mmol) was added into an aqueous solution of LiOH (2.5 M, 7.5 mL). The mixture was stirred at 50° C. for 0.5 h and then the solid was collected by filtration. The solid was wash with 0.1M HCl to neutral and then stirred with EtOH (30 mL), and water (30 mL). After drying under high vacuum, a white solid was obtained (0.234 g, 67%). $^1$H NMR (400 MHz, D$_2$O): 6.95 (s, 4H), 5.62 (d, J=15.3, 2H), 5.52 (d, J=15.7, 4H), 5.43 (d, J=8.0, 2H), 5.20 (d, J=8.0, 2H), 4.72 (d, J=16.2, 4H), 4.28 (d, J=15.7, 4H), 4.23 (d, J=16.2, 4H), 4.19 (d, J=15.3, 2H), 3.85-3.50 (m, 8H), 3.45-2.85 (m, 8H), 1.76 (s, 12H).

Figure 16:
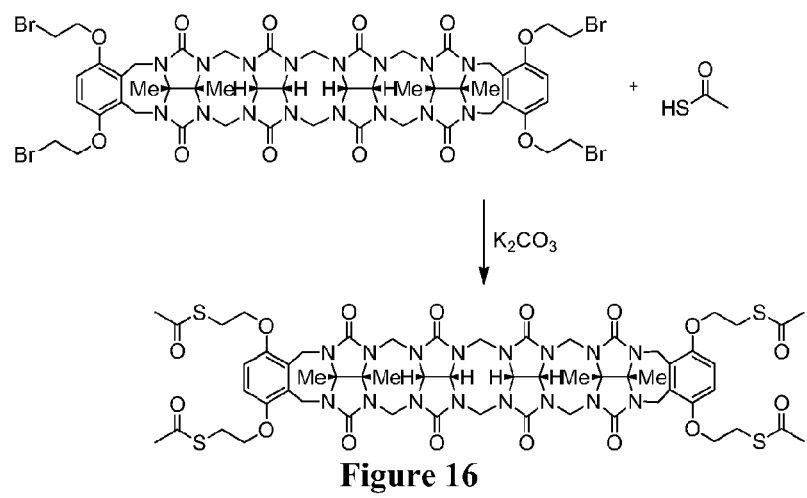

Tetrathioacetate Host (FIG. 16). K$_2$CO$_3$ (99 mg, 0.43 mmol) and thiolacetic acid (55 mg, 0.43 mmol) was added into DMF (2 mL) and was stirred at RT for 15 min under N$_2$. Tetrabromo Host (100 mg, 0.072 mmol) was added as a solid. The mixture was stirred at 50° C. for 12 h and then was poured into H$_2$O (6 mL). The solid was collected by filtration and was then washed with H$_2$O (5 mL) and acetone (5 mL). A beige solid was obtained after drying under high vacuum (73 mg, 74%). $^1$H NMR (400 MHz, DMSO): 6.85 (s, 4H), 5.58 (d, J=16.3, 2H), 5.48 (d, J=15.6, 4H), 5.38 (d, J=9.0, 2H), 5.27 (d, J=9.0, 2H), 5.22 (d, J=16.0, 4H), 4.25-4.10 (m, 4H), 4.15-3.90 (m, 14H), 3.35-3.25 (m, 8H), 2.37 (s, 12H), 1.68 (s, 6H), 1.64 (s, 6H).

Figure 17:
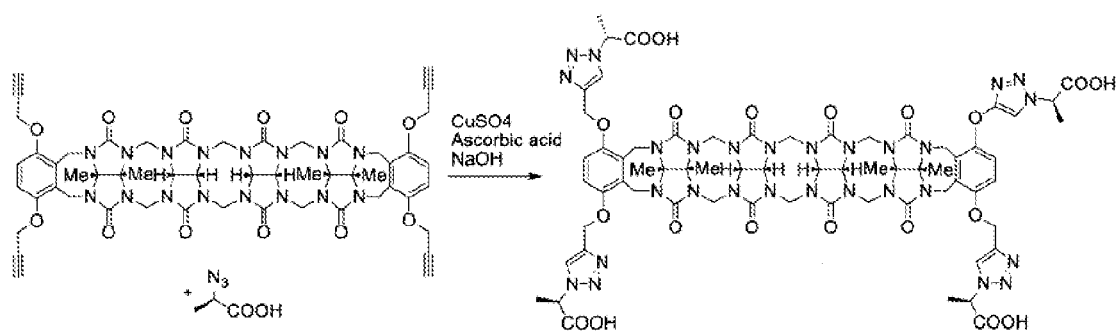
Figure 18:
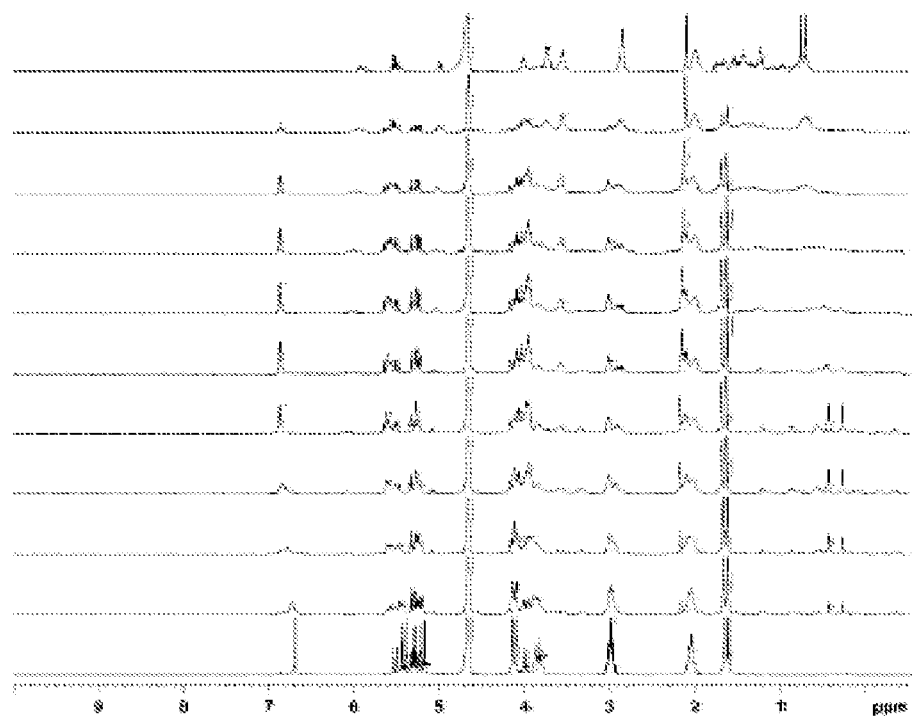
Figure 18:
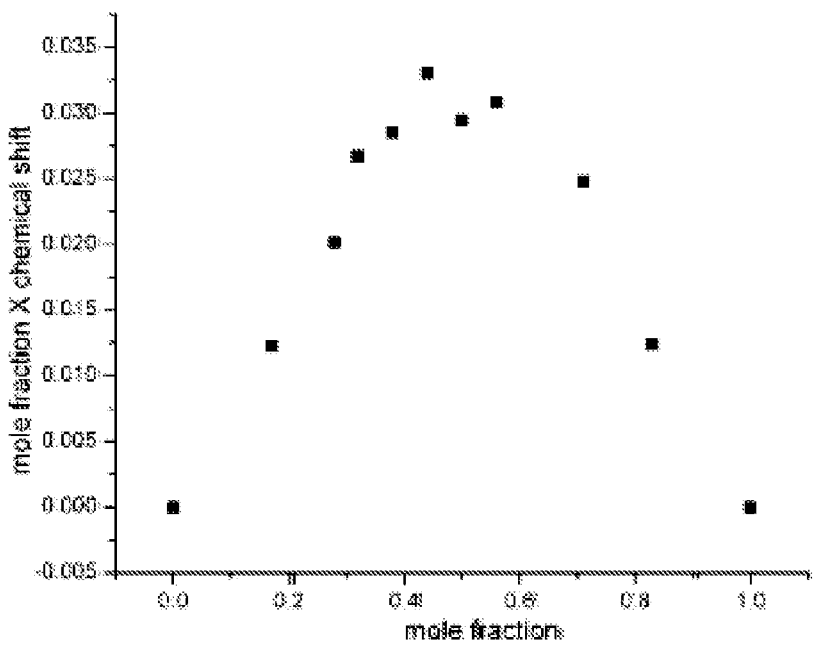
Figure 19:
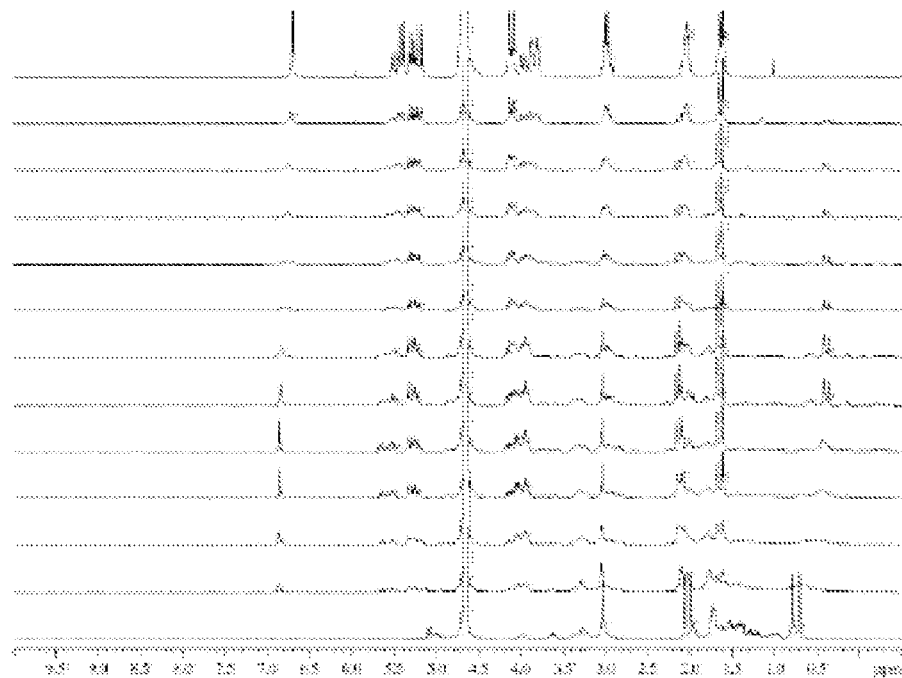
FIG. 19. An example of a Job plot of Motor1 and Vecuronium bromide (total concentration 5 mM, 20 mM $NaH_2PO_4$ buffer, pH 7.4): (A) Stack plot of $^1H$ NMR spectra; (B) Job plot of Motor1 (constructed using the chemical shift of the downfield singlet).
Figure 19:
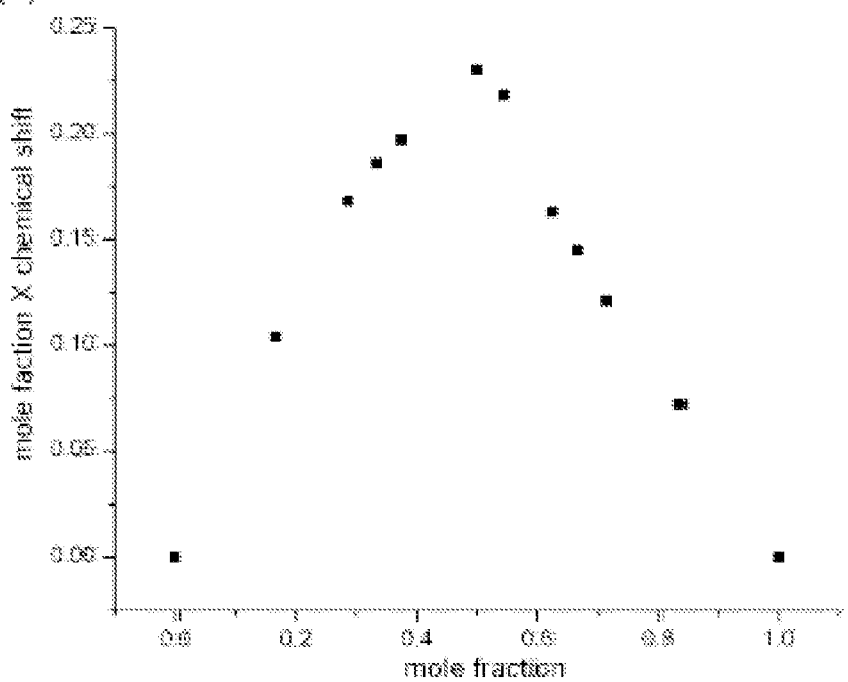
Figure 20:
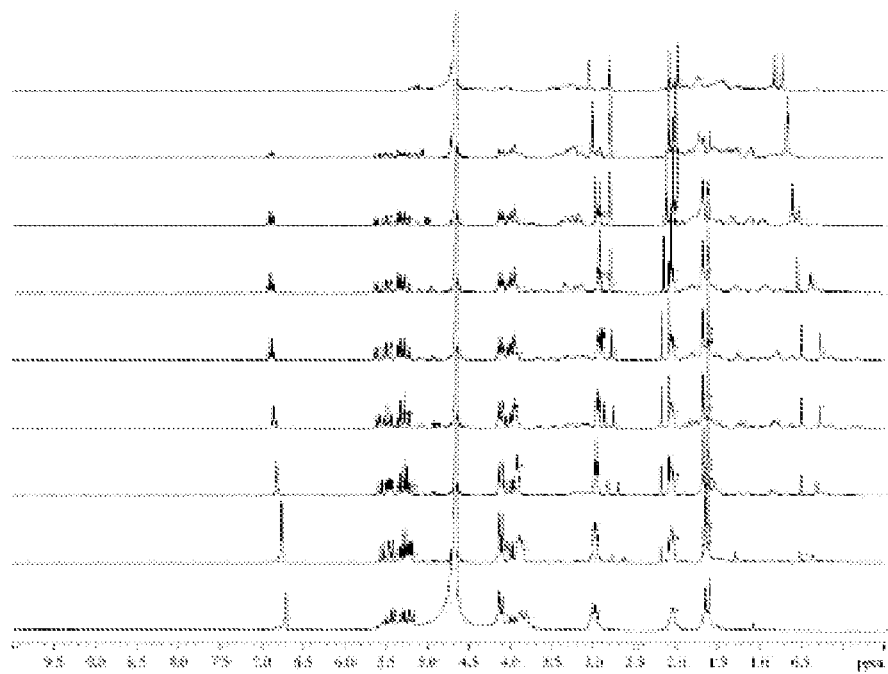
FIG. 20. An example of a Job plot of Motor1 and Pancuronium bromide (total concentration 5 mM, 20 mM $NaH_2PO_4$ buffer, pH 7.4): (A) Stack plot of $^1H$ NMR spectra; (B) Job plot of Motor1 (constructed using the chemical shift of the aromatic proton on Motor1).
Figure 20:
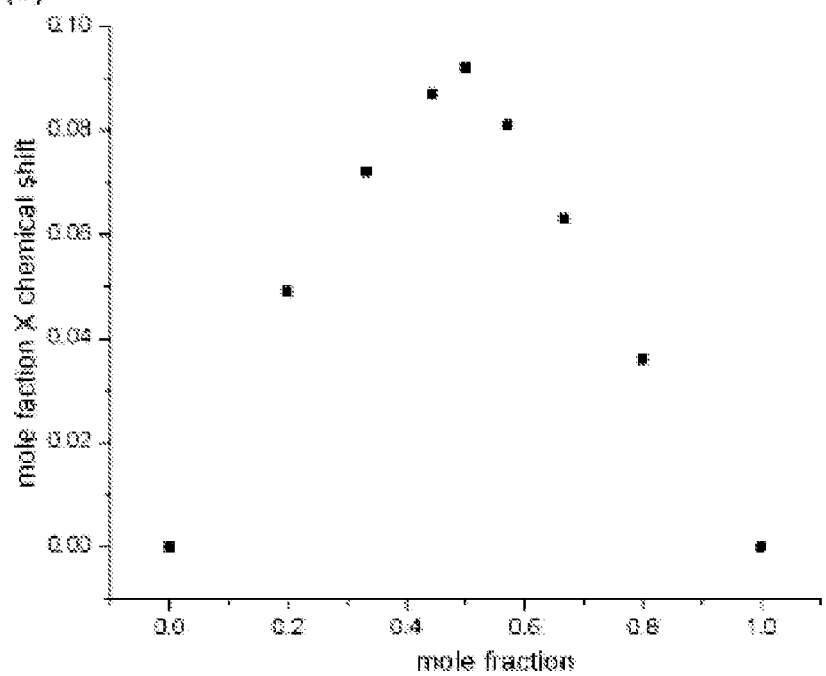
Figure 21:
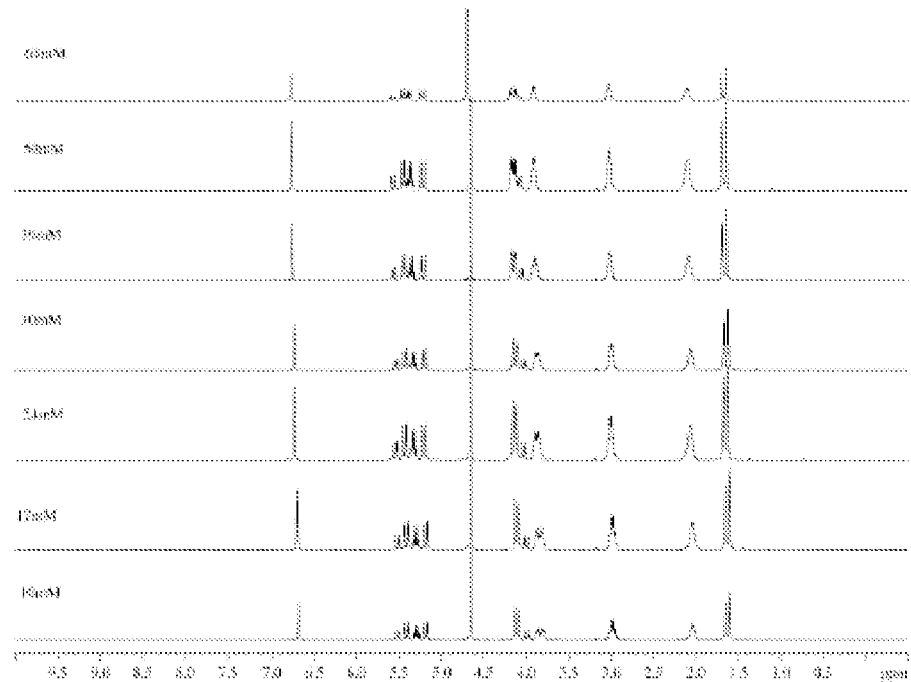
FIG. 21. An example of $^1H$ NMR spectra recorded for Motor1 at varied concentration (400 MHz, 20 mM $NaD_2PO_4$, pD=7.4) for self-association study.
Figure 22:
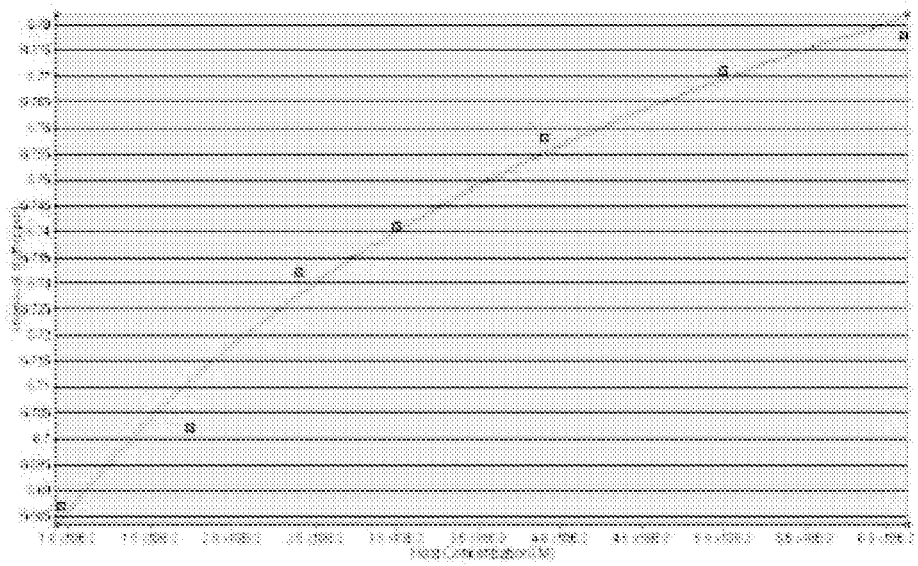
FIG. 22. An example of a plot of chemical shift of Motor1 versus [Motor1]. The solid line represents the best non-linear fitting of the data to a two-fold self-association model with $K_a=47$ $M^{-1}$.
Figure 23:
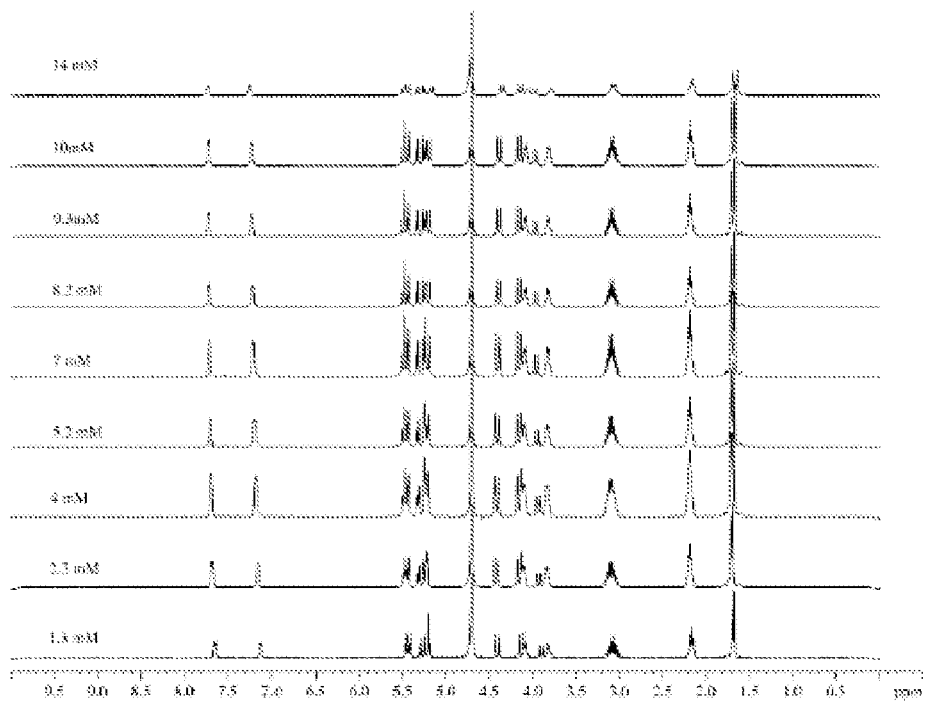
FIG. 23. An example of $^1H$ NMR spectra recorded for Motor2 at varied concentration (400 MHz, 20 mM $NaD_2PO_4$, pD=7.4) for self-association study.
Figure 24:
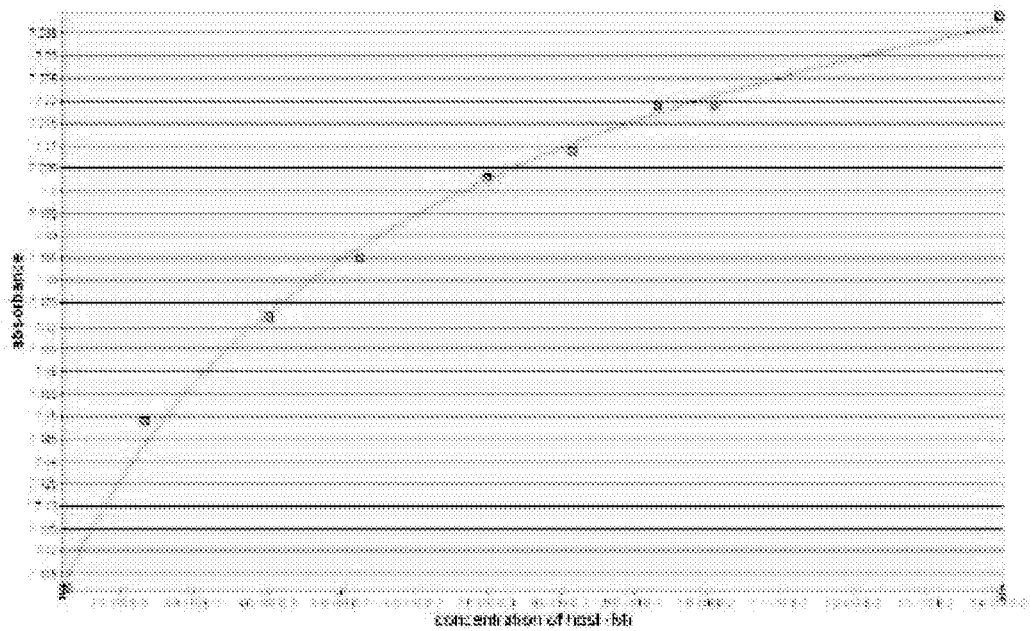
FIG. 24. An example of a plot of chemical shift of Motor2 versus [Motor2]. The solid line represents the best non-linear fitting of the data to a two-fold self-association model with $K_a=624$ $M^{-1}$.
Figure 25:
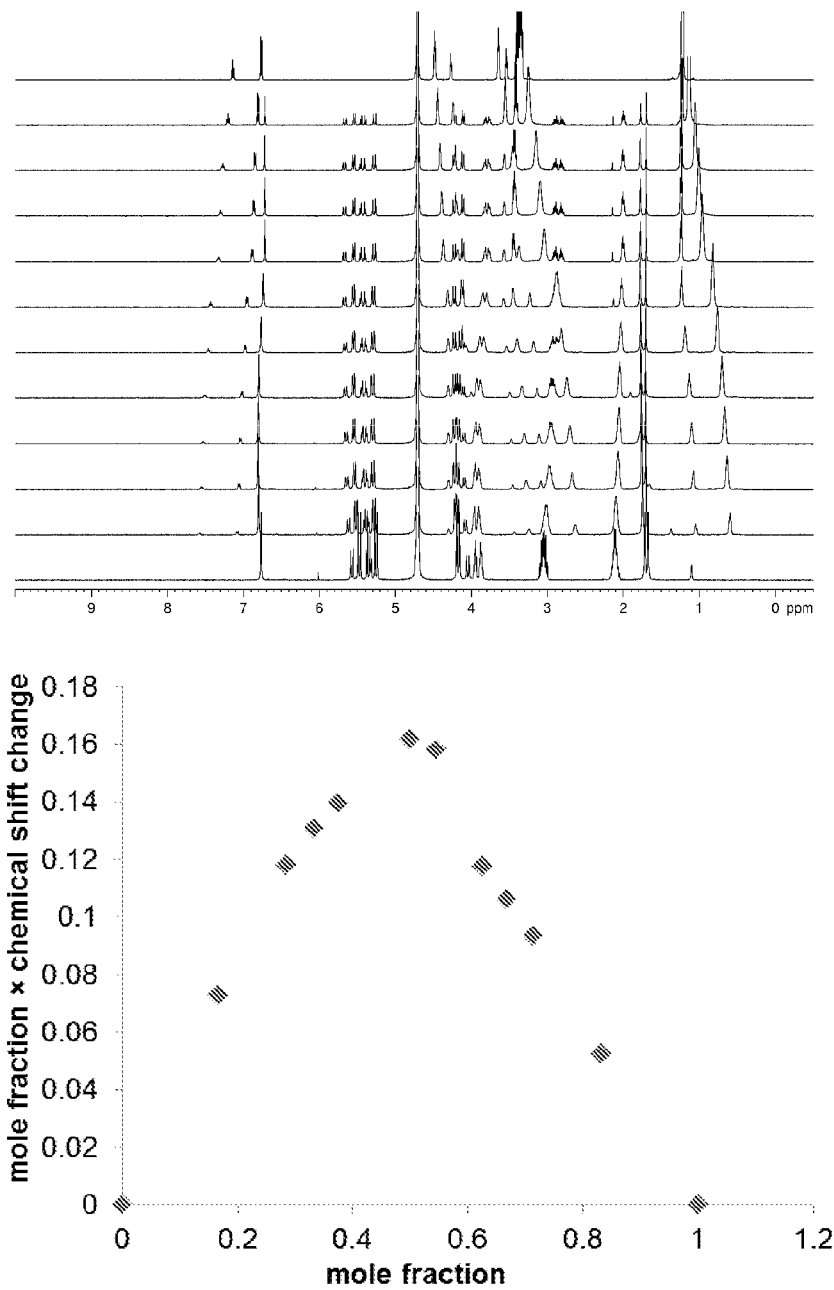
FIG. 25. An example of a Job plot of Motor1 and Gallamine (total concentration 5 mM, 20 mM $NaH_2PO_4$ buffer, pH 7.4): (A) Stack plot of $^1H$ NMR spectra; (B) Job plot of Motor1 (constructed using the chemical shift of the aromatic proton peak on Motor1).
Figure 26:
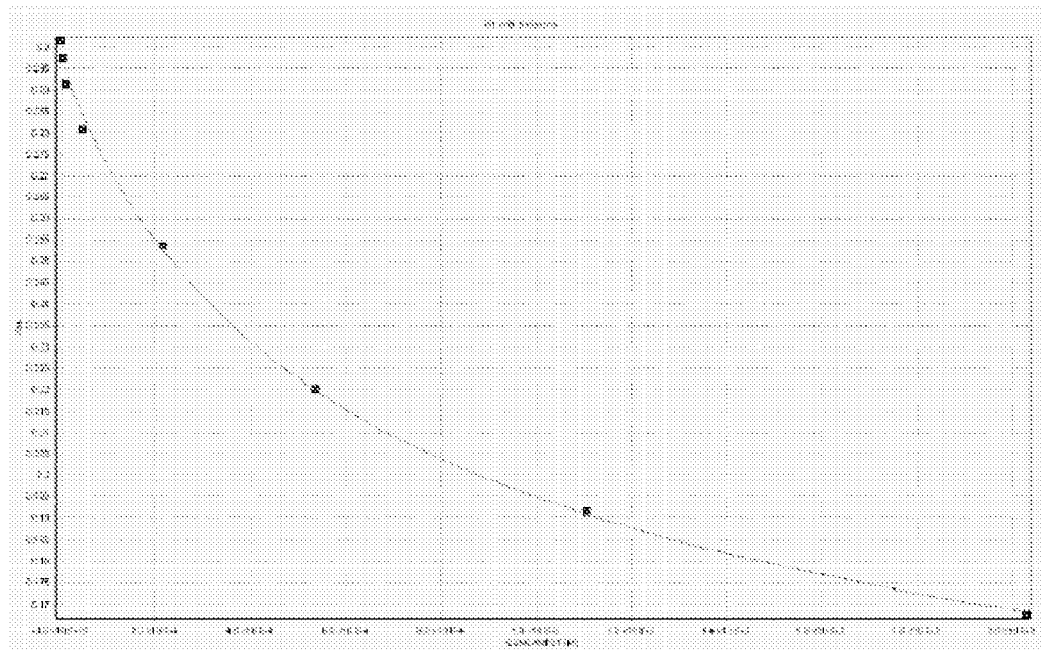
FIG. 26. An example of a non-linear fitting plot of absorbance versus concentration for the displacement titration of Motor1 complexed to Rhodamine 6G by the addition of Ketamine with Scientist™ (Conditions: Rhodamine 6G=0.010 mM, Motor1=0.009 mM, 20 mM phosphate buffer pH 7.4). $K_a$ for the complex between Motor1 and Ketamine was evaluated as 39020 $M^{-1}$.

Tetra Triazole Host (FIG. 17). Ascorbic acid (7 mg, 0.04 mmol), NaOH (2 mg, 0.04 mmol) and CuSO$_4$ (2 mg, 0.01 mmol) was mixed and then dissolved in a mixture of H$_2$O and EtOH (1 mL, 1:1). Alkyne Host (26 mg, 0.024 mmol) and (R)-2-azidopropanoic acid (22 mg, 0.19 mmol) was added as solid. The mixture was heated with microwave at 80° C. for 30 min, and then solvent was removed under reduced pressure. The crude solid was washed with MeOH (2 mL). A yellowish solid was obtained after drying under high vacuum (15 mg, 40%). $^1$H NMR (400 MHz, DMSO): 8.44 (s, 2H), 8.34 (s, 2H), 6.97 (m, 4H), 5.65-5.45 (m, 12H), 5.39 (d, J=8.4, 2H), 5.25-5.05 (m, 18H), 4.25-4.00 (m, 4H), 1.72 (m, 12H), 1.69 (s, 6H), 1.64 (s, 6H).

EXAMPLE 3

TABLE 1

Binding constants of Motor1 towards guests:

| Guest | $K_a$ |
|---|---|
| vecuronium | $5.8 \pm 0.9 \times 10^6$ |
| pancuronium | $4.5 \pm 0.1 \times 10^5$ |

TABLE 1-continued

Binding constants of Motor1 towards guests:

| Guest | $K_a$ |
|---|---|
| atracurium | $1.4 \pm 0.1 \times 10^6$ |
| tubocurarine | $4.7 \pm 0.2 \times 10^5$ |
| gallamine | $6.2 \pm 0.5 \times 10^6$ |
| acetylcholine | $2.4 \pm 0.1 \times 10^4$ |

TABLE 2

Compounds used and their binding affinities towards Motor2.

| Compound Name | $K_a$ (M$^{-1}$) with Motor2 |
|---|---|
| Rhodamine 6G | $2.3 \pm 0.2 \times 10^8$ |
| Cyclohexanediamine | $2.1 \pm 0.2 \times 10^8$ |
| Proflavin | $7.8 \pm 0.8 \times 10^8$ |
| Bacuronium | $3.4 \pm 0.6 \times 10^9$ |
| Vecuronium | $1.6 \pm 0.2 \times 10^9$ |
| Pancuronium | $5.3 \pm 0.5 \times 10^8$ |
| Atracurium besilate | $1.0 \pm 0.1 \times 10^9$ |
| Gallamine | $3.2 \pm 0.4 \times 10^8$ |
| Turbocurium | $2.2 \pm 0.3 \times 10^9$ |
| Acetylcholine | $1.8 \pm 0.2 \times 10^8$ |

EXAMPLE 4

Testing of the binding abilities of Motor1 and Motor2 with Ketamine, and Etomidate respectively.

For the binding of Motor1 1 and Ketamine, Rhodamine 6G was used as an indicator to perform a competition experiment to determine the binding constant. A solution of Rhodamine 6G (0.010 mM), Motor1 (0.009 mM, 2.4 mL) was titrated by a stock solution of Rhodamine 6G (0.010 mM) and Motor1 (0.009 mM) and Ketamine (2.10 mM) in Phosphate buffer (20 mM, pH=7.4). The absorbances of the solution at 550 nm were monitored by UV-VIS spectroscopy, and then used to calculate the binding constant.

Table 3.

Remaining binding constants for Motor1 and Motor2 with Ketamine and Etomidate.

TABLE 3

|  | Ketamine | Etomidate |
|---|---|---|
| Motor1 | 39020M$^{-1}$ | 35318M$^{-1}$ |
| Motor2 | 193490M$^{-1}$ | 36812M$^{-1}$ |

For urine samples (Table 4), we took 0.1 mL from each urine sample and dried them under high vacuum. Then they were dissolved in 0.5 mL D$_2$O, and 0.1 mL of 60 mM reference solution (1,3,5-tricarboxylate benzene) was added. NMR spectra were taken and the concentration of Motor1 in urine was calculated from the ratio between the integration of diagnostic peak for reference (8.3 ppm, 3H) and Motor1 (1.9-1.5 ppm, 12H).

TABLE 4

| Sample No. | Urine volume (μL) | Integral* | [Motor1] (mM) | [Motor1] (mg/mL) | Mass (Motor1) (mg) | Notes |
|---|---|---|---|---|---|---|
| R1U | 930 | 3.34 | 6.958 | 10.723 | 9.972 | |
| R2U | 530 | 0.06 | 0.125 | 0.193 | 0.102 | Blood in urine |
| R3U | 580 | 0.25 | 21.354 | 32.907 | 19.086 | |
| R4U | 240 | 8.88 | 18.500 | 28.509 | 6.842 | Precipitate in urine |
| R5U | 1350 | 0.00 | 0.000 | 0.000 | 0.000 | |
| R6U | 415 | 0.00 | 0.000 | 0.000 | 0.000 | |
| R7U | 725 | 5.72 | 11.917 | 18.364 | 13.314 | |
| R8U | 610 | 13.78 | 28.708 | 44.240 | 26.986 | |
| R9U | 950 | 4.21 | 8.771 | 13.516 | 12.840 | |
| R10U | 315 | 8.70 | 18.125 | 27.931 | 8.798 | |
| R11U | 560 | 1.03 | 2.146 | 3.307 | 1.852 | |
| R12U | | | | | | N/A |
| R13U | 815 | 0.00 | 0.000 | 0.000 | 0.000 | |
| R14U | 355 | 10.62 | 22.125 | 34.095 | 12.104 | |
| R15U | 305 | 6.88 | 14.333 | 22.088 | 6.737 | Blood in urine |
| R16U | 455 | 12.28 | 25.583 | 39.424 | 17.938 | |
| R17U | 255 | 10.74 | 22.375 | 34.480 | 8.792 | |
| R18U | 610 | 0.00 | 0.000 | 0.000 | 0.000 | |
| R19U | 615 | 1.27 | 2.646 | 4.077 | 2.507 | Precipitate in urine |
| R20U | 190 | 5.39 | 11.229 | 17.304 | 3.288 | Precipitate in urine |
| R21U | 585 | 2.40 | 5.000 | 7.705 | 4.507 | |
| R22U | 390 | 0.00 | 0.000 | 0.000 | 0.000 | Precipitate in urine |

*Peak from 1.65-1.9 ppm, with reference peak integral for benzene-1,3,5-tricarboxylic acid (5 mM) at 8.3 ppm set to 3

EXAMPLE 5

Toxicity Studies: To measure the cellular toxicity of Motor1 we use two complementary assays: an MTS (Cell-Titer 96 AQueous Kit®) assay that measures cellular metabolism, and a cytotoxicity assay (Toxilight®BioAssay Kit) that measures cell death via the release of the cytosolic enzyme adenylate kinase into the supernatant. Both assays were used with two different cell lines commonly used in drug toxicity studies, HEK293 and HepG2 cell lines. HEK293, a human kidney cell line, is used to assess the effect of the drug candidate on the renal system and HepG2, a human hepatocyte cell line, is used to assess the response of liver cells where drugs are metabolized. Both assays included the use of an untreated population, and cells treated with distilled water, erythromycin and erythromycin estolate. Erythromycin is a commercially available drug widely used to treat bacterial infections. Erythromycin estolate, however, is a derivative with high toxicity. Erythromycin, with an EC50 value of 594 (±194) μM is significantly less toxic compared to erythromycin estolate, which has an EC50 of 109 (±7) μM. These two drugs were chosen specifically to serve as a point of comparison for the levels of cytotoxicity resulting from Motor1.

Both cell lines were incubated with the containers (0.01, 0.1, 1 and 10 mM) for 2 days prior to analysis with the two assays. Relative absorbance and luminescence data was normalized to percent cell viability (MTS) and cell death (AK). For the MTS assay, the untreated cells were set at 100% cell viability while the cell population treated with distilled water was set at a 100% cell death for the AK assay.

Figure 27:
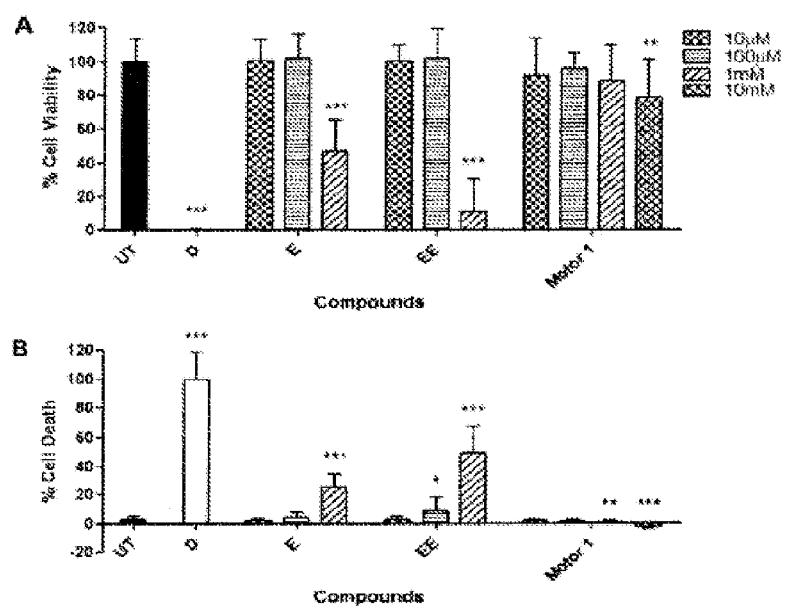
FIG. 27. Toxicology of Motor1 using the human kidney cell line HEK293. Results from (A) MTS assay (B) AK assay. Untreated population (UT), Distilled water (D), Erythromycin (E), Erythromycin Estolate (EE).

The MTS assay conducted on the HEK293 (FIG. 27A) cell line showed high cell survival in the all concentrations of Motor1 at 92, 96, 89 and 79% cell viability. However, cell populations treated with distilled water (0.2%), 1 mM of erythromycin (47%) and erythromycin estolate (11%) showed significant decrease in cell viability. The AK assay (FIG. 27B) performed on this cell line reflected these results. Percent cell death observed in the cells treated with 1 mM erythromycin and erythromycin estolate were 25 and 49% respectively. However, cell death in the untreated population and all concentrations of Motor1 was below 5%.

Figure 28:
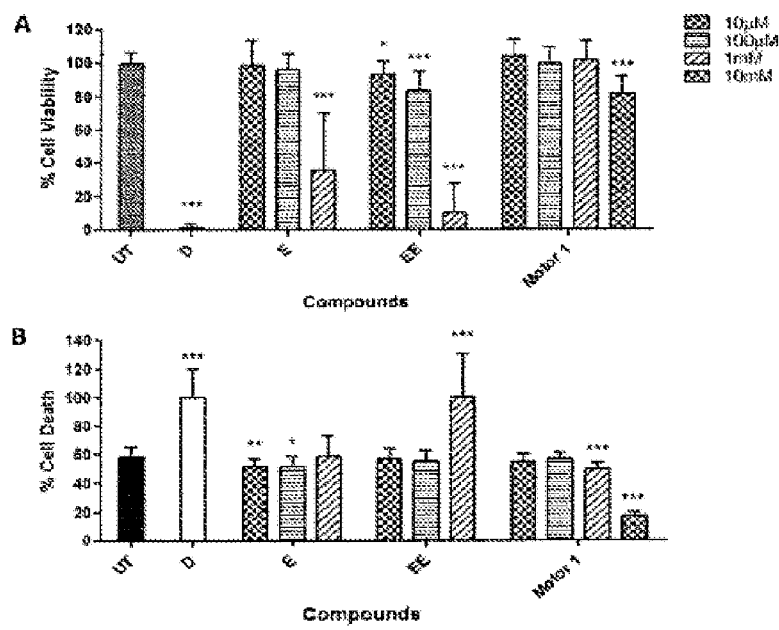
FIG. 28. Toxicology of Motor1 using the human liver cell line HepG2. Results from (A) MTS assay (B) AK assay. Untreated population (UT), Distilled water (D), Erythromycin (E), Erythromycin Estolate (EE).

Similar results were observed in the HepG2 cell line (FIG. 28). The HepG2 cells treated with increasing concentrations of Motor1 showed high cell viability at 104, 100, 102 and 82% respectively in the MTS assay (FIG. 28A). These results were comparable to cell viability observed in the untreated population. However, HepG2 cells treated with distilled water (1%), 1 mM erythromycin (36%) and erythromycin estolate (10%) showed significant decreases in cell viability. These results were confirmed in the AK assay (FIG. 28B) performed using the HepG2 cell line. High percentage of cell death was observed with samples treated with erythromycin estolate at 1 mM (100% cell death). HepG2 cells exhibited high background levels in this assay as indicated by the 60% cell death in the untreated population. All cell samples treated with increasing concentrations of Motor1 show low cytotoxicity (55, 56, 50 and 17% cell death) in comparison to the untreated samples.

Overall Motor1 was found to be non-toxic in both human kidney and liver cells up to a concentration of 10 mM.

Figure 29:
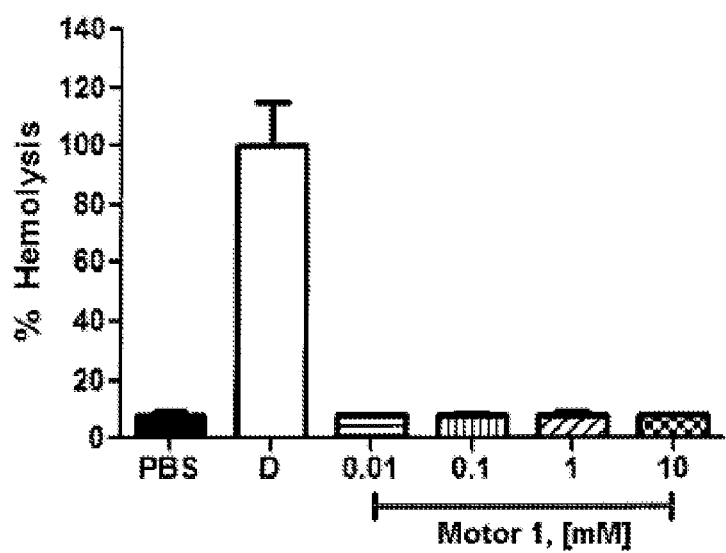
FIG. 29. Percent hemolysis at 3 h caused by increasing concentrations of the compound Motor1. Phosphate Buffer Saline (PBS), Distilled water (D).

A hemolysis assay (FIG. 29) was conducted to assess any toxic effects of Motor1 on human erythrocytes. These assays used pooled blood from two healthy donors from which red blood cells were isolated through centrifugation. Erythrocytes were exposed to phosphate buffered saline (PBS), distilled water, and increasing concentrations of Motor1 (1) (0.01, 0.1, 1 and 10 mM). The erythrocytes were incubated shaking at 37° C. for 3 h following treatment. The release of hemoglobin from damaged red blood cells was quantified by measuring the relative absorbance of the samples at 405 nm. Data collected was converted to percent hemolysis by setting the cell population treated with distilled water at a 100% hemolysis.

This assay showed that while erythrocytes treated with distilled water resulted in a high percentage of hemolysis, samples incubated with PBS, and increasing concentrations of Motor1 did not result in hemolysis above 20%. The hemolysis assay presented data towards the conclusion that the Motor1 is non-toxic to human erythrocytes up to a concentration of 10 mM.

Figure 30:
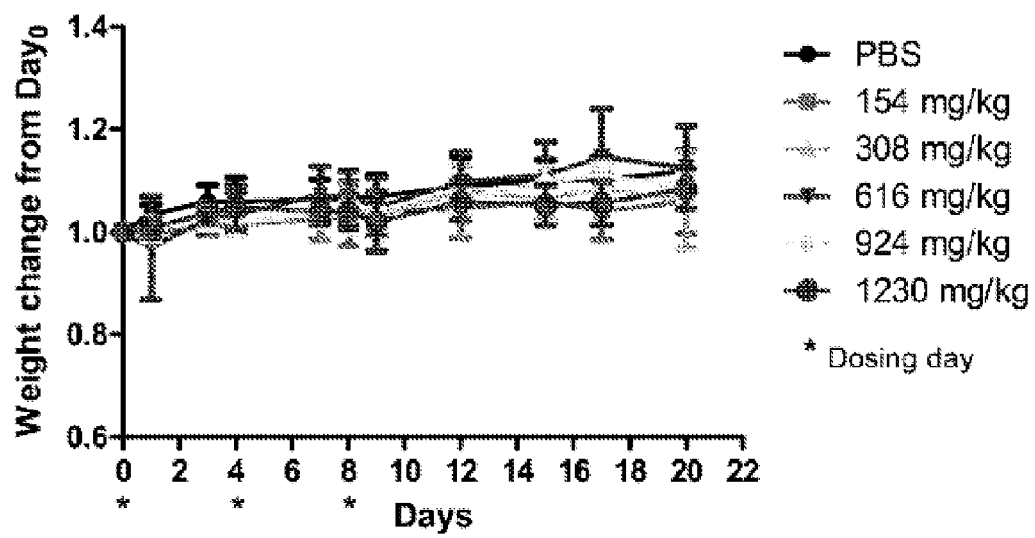
FIG. 30. Motor1 is well tolerated in mice. Indicated amounts of Motor1 were injected into the tail vein of outbred Swiss Webster mice at day 0, 4 and 8. The weight of each mouse was monitored over time and there were 5 mice per experimental group.
Figure 31:
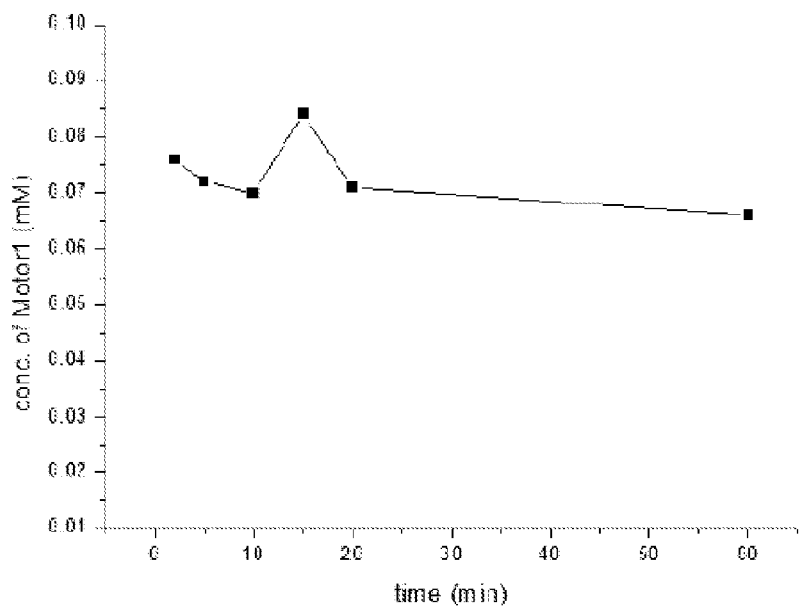
FIG. 31. An example of a plot of concentration (mM) of Motor1 in plasma versus time (min) plot for Rat 17.
Figure 32:
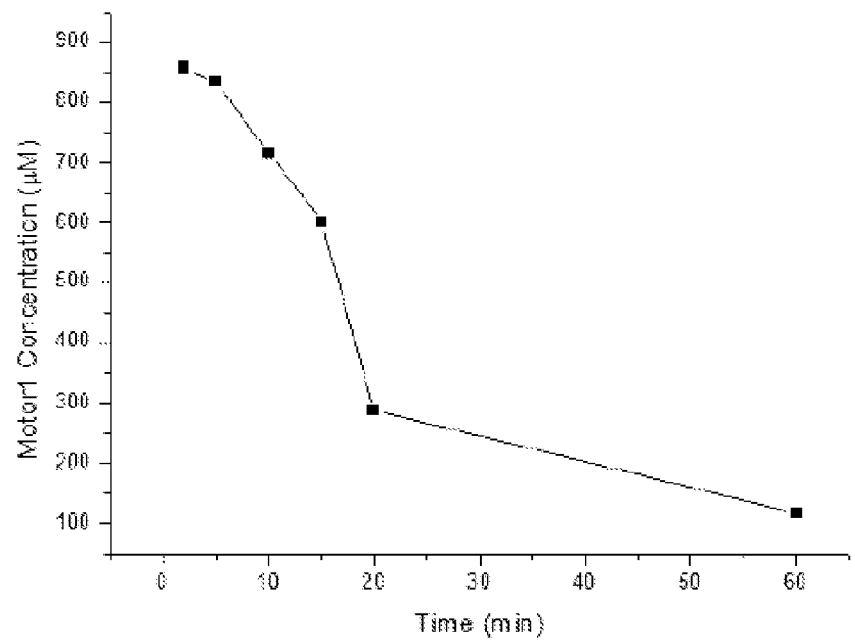
FIG. 32. An example of a plot of concentration (mM) of Motor1 in plasma versus time (min) plot for Rat 10.
Figure 33:
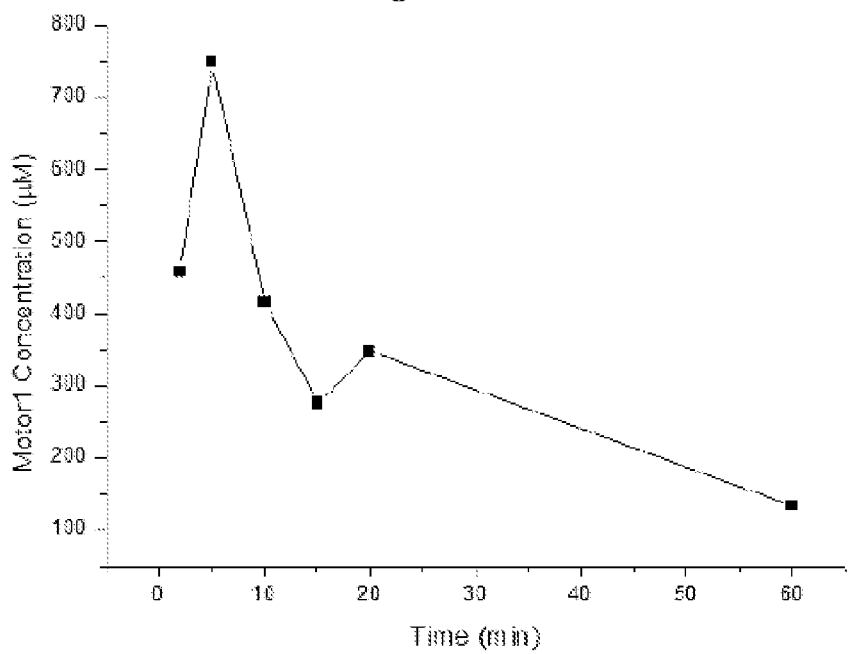
FIG. 33. An example of a plot of concentration (mM) of Motor1 in plasma versus time (min) plot for Rat 11.
Figure 34:
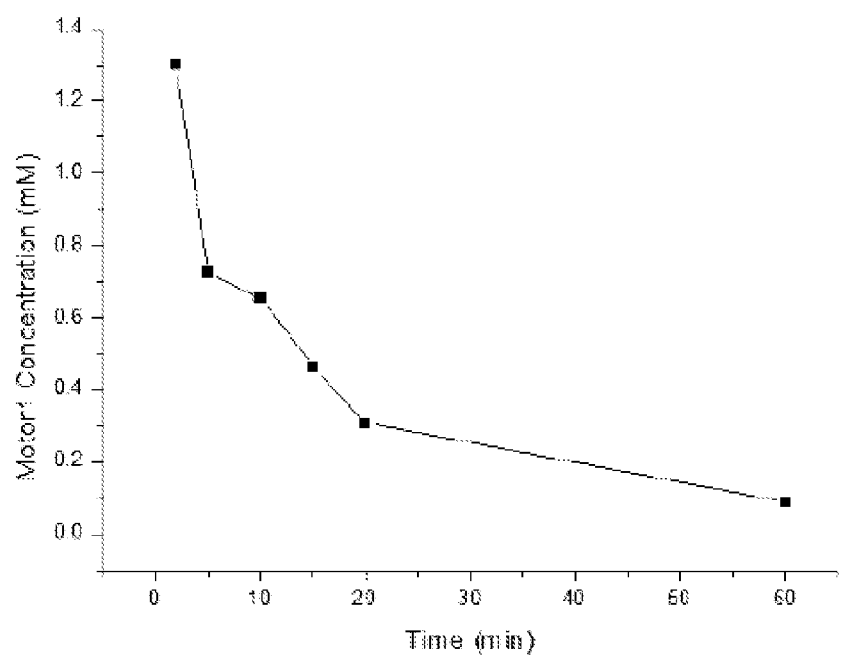
FIG. 34. An example of a plot of concentration (mM) of Motor1 in plasma versus time (min) plot for Rat 21.

FIG. 30 shows Motor1 is well tolerated in mice. Indicated amounts of Motor1 were injected into the tail vein of outbred Swiss Webster mice at day 0, 4 and 8. The weight of each mouse was monitored over time and there were 5 mice per experimental group.

For Plasma samples, four rats in total have been tested: Rat 10, Rat 17, Rat 11, Rat 21. For each plasma sample, 10 µL of plasma was taken and dried under high vacuum. Excess amount of probe solution was added (495 µL of 38 µM p-xylenediamine) to dissolve the residue and then the reference (5 µL of 600 µM benzene-1,3,5-tricarboxylic acid) was added. NMR spectra was taken with water suppression and the concentration of Motor1 was calculated from the ratio between the integrations of the peaks for the reference (8.2 ppm, 3H) and Motor1 (6.5 ppm, 4H). For Rat 17, benzene-1,3,5-tricarboxylic acid was not used, but p-xylenediamine was used as the reference (FIGS. 31-34).

Figure 35:
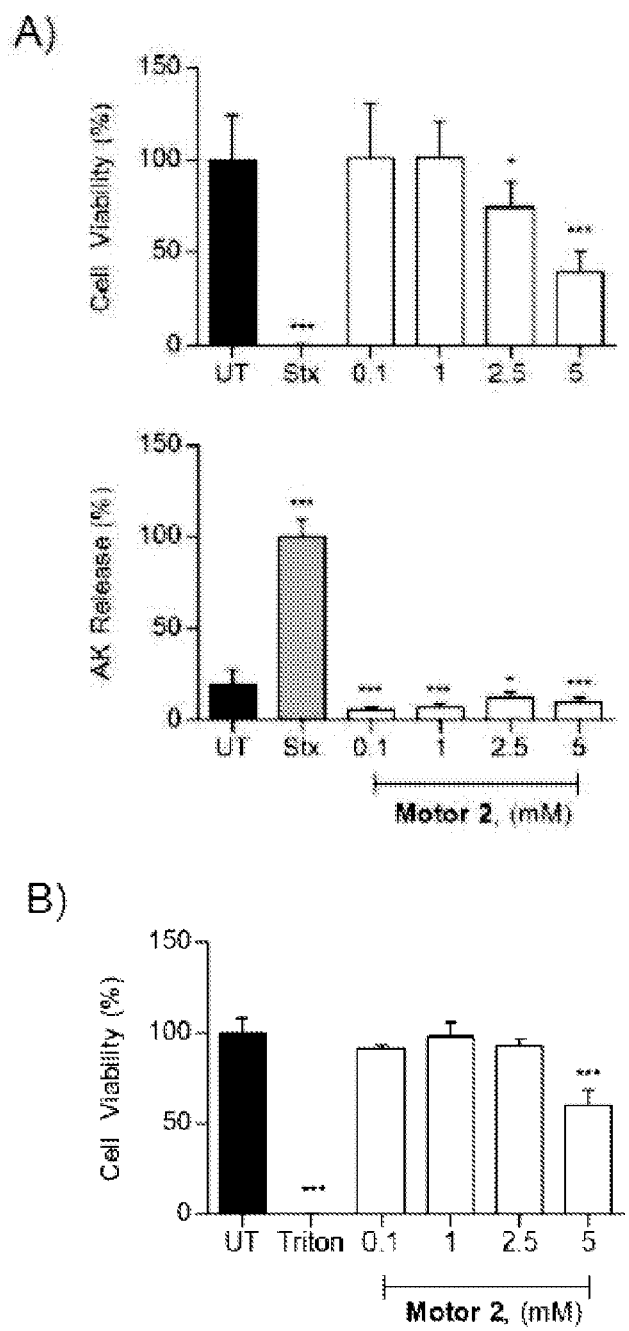
FIG. 35. Varying concentrations of Motor2 incubated with THP-1 (A) and HEK 293 (B) cells over a 48 hr period resulted in high cell survival up to 5 mM. Two complementary assays were used to analyze toxicology an MTS and an AK release assay for the THP-1 cells. The AK release assay was conducted using 20 ul of supernatant from each sample studied using the MTS assay. The Vialight assay was used to assess cell viability in the HEK 293 cells. (UT=Untreated, Stx=Staurosporine, Triton=Trition-X-100). Unpaired t-test analysis was used with *P=0.01-0.05; P=0.001-0.01; *P, 0.001 for the statistical analysis of all figures presented.
Figure 36:
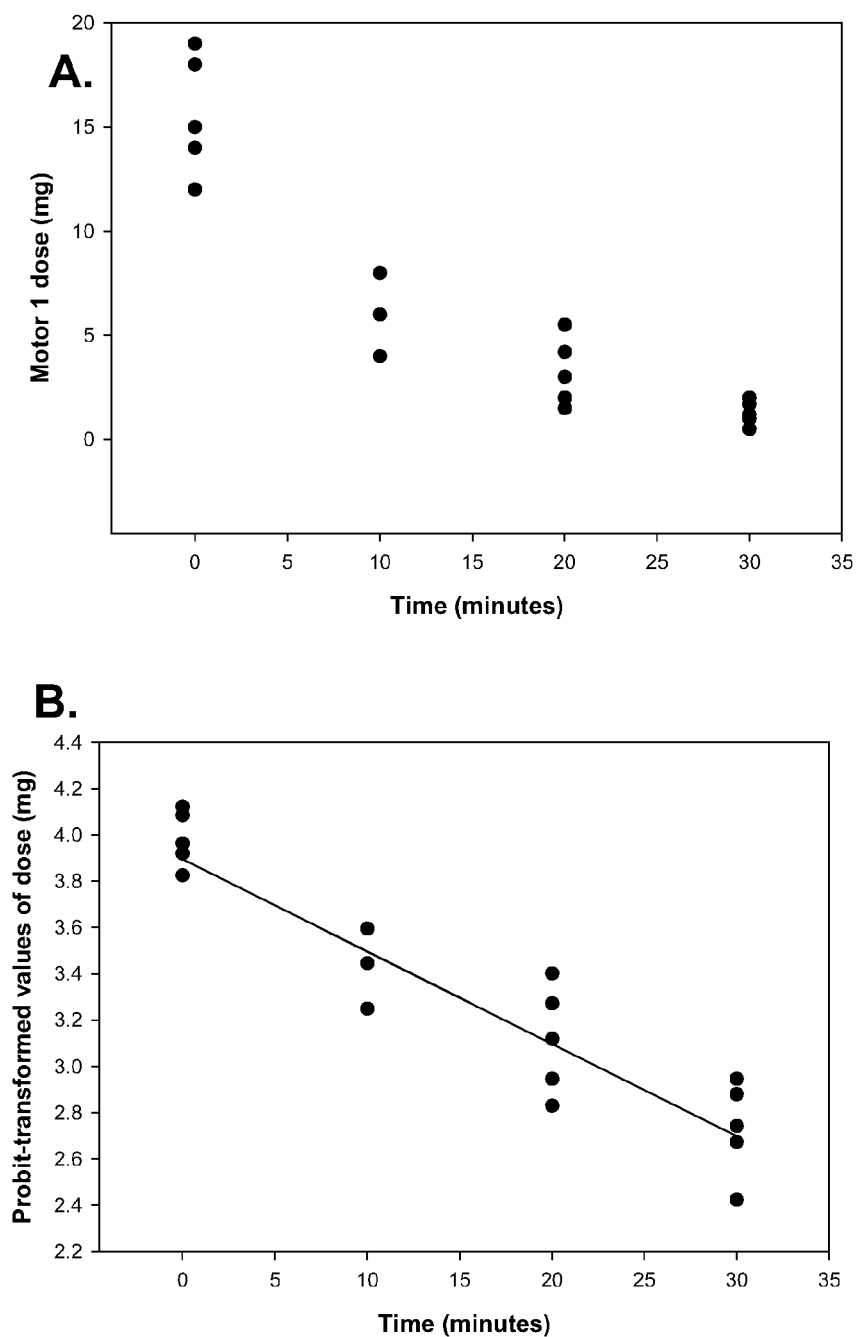
FIG. 36. Time to complete recovery of muscle strength following Motor1 injection. Dose-response relationship of Motor1 to reverse rocuronium. A: time to recovery of muscle strength to baseline as a function of Motor1 dose. B: Probit-transformed dose, line: linear regression. The data show a predictable dose-response relationship.
Figure 37:
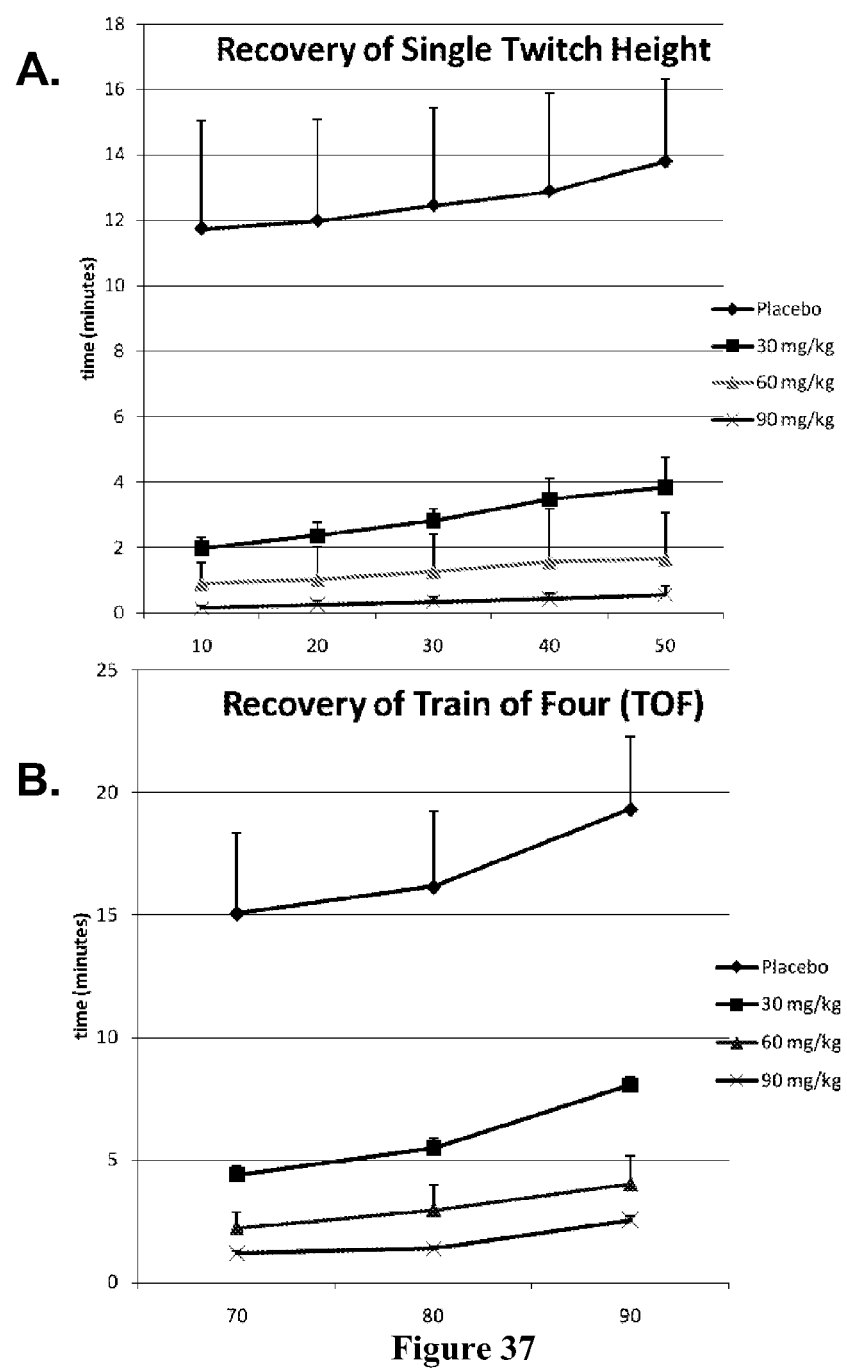
FIG. 37. Time to recovery of twitch height (A) and train-of-four ratio (B) following complete rocuronium-induced neuromuscular block. Recovery profile is shown in response to different Motor1 doses and placebo. Mean time to recovery of the twitch height to 90% following Motor2 (90 mg) versus placebo amounted to 2.5 versus 19 minutes.
Figures 38, 39:
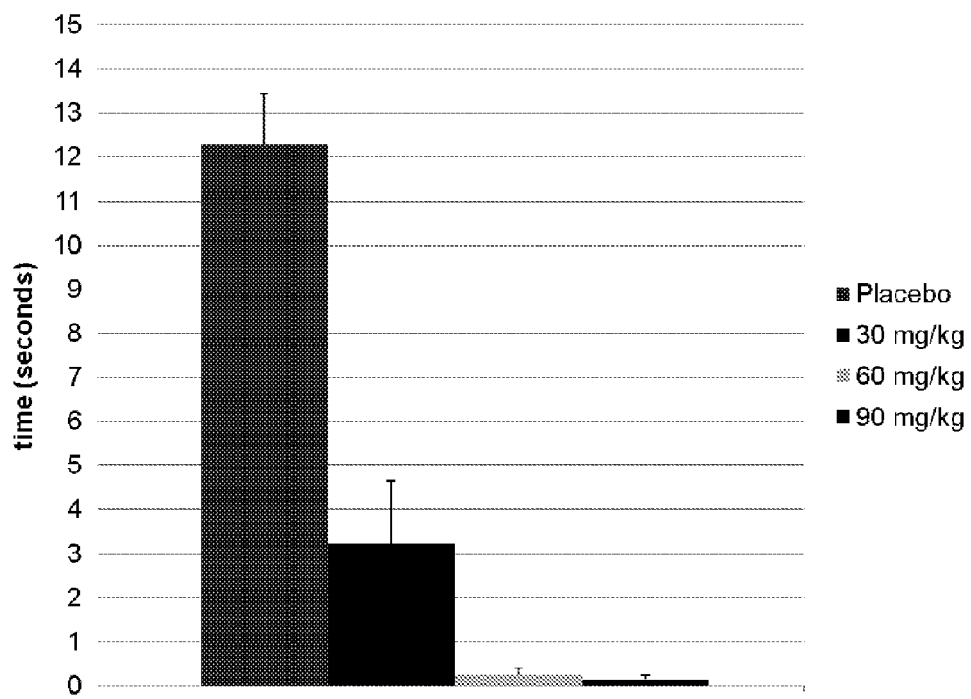
FIG. 38. Time to recovery of spontaneous breathing following complete rocuronium-induced neuromuscular block. Recovery time is given in response to different Motor1 doses and placebo. Mean recovery of spontaneous breathing amounted to 10 seconds after Motor1 versus 723 seconds following Motor1 90 mg.
FIG. 39. Arterial Blood Gas Parameters before and after application of Motor1: Safety of Motor1 given during steady state isoflurane anesthesia (which cannot be reversed by Motor1)—respiratory: pH, $pCO_2$, and $pO_2$ did not change following Motor1 injection FIG. 40. Blood Pressure and Heartrate during and After Application of Motor1: Safety of Motor1 during steady state isoflurane anesthesia—cardiovascular: heart rate and mean arterial blood pressure did not change.
Figure 40:
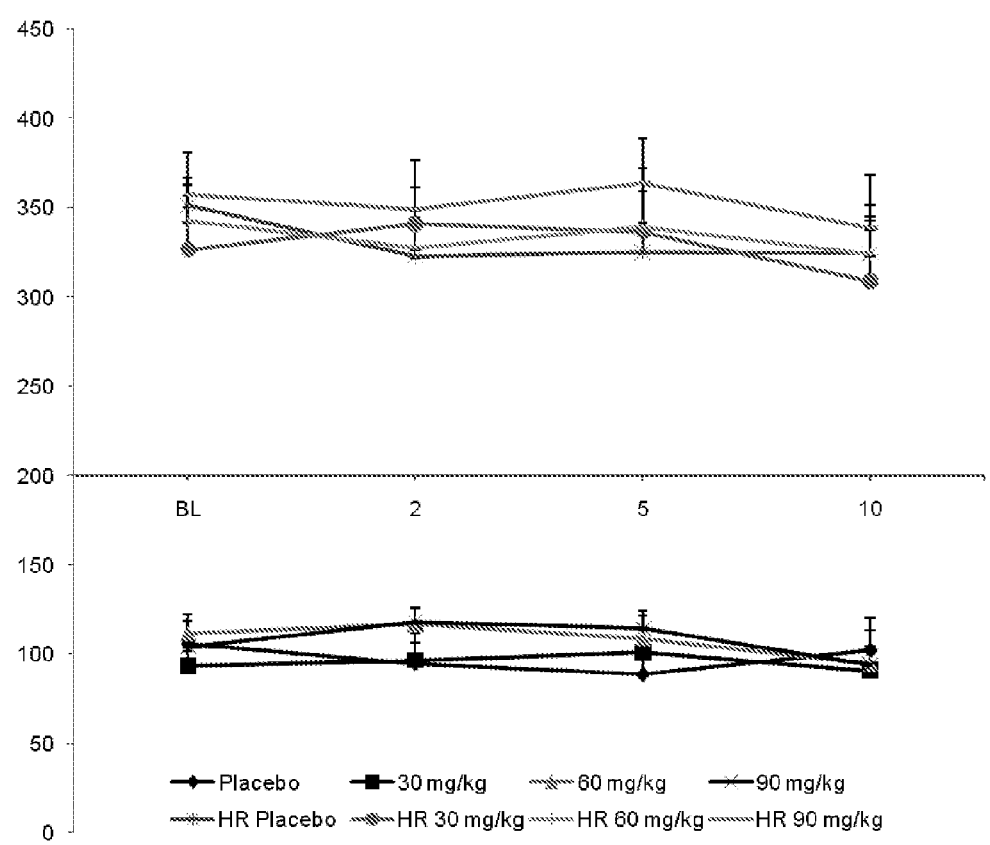
Figure 41:
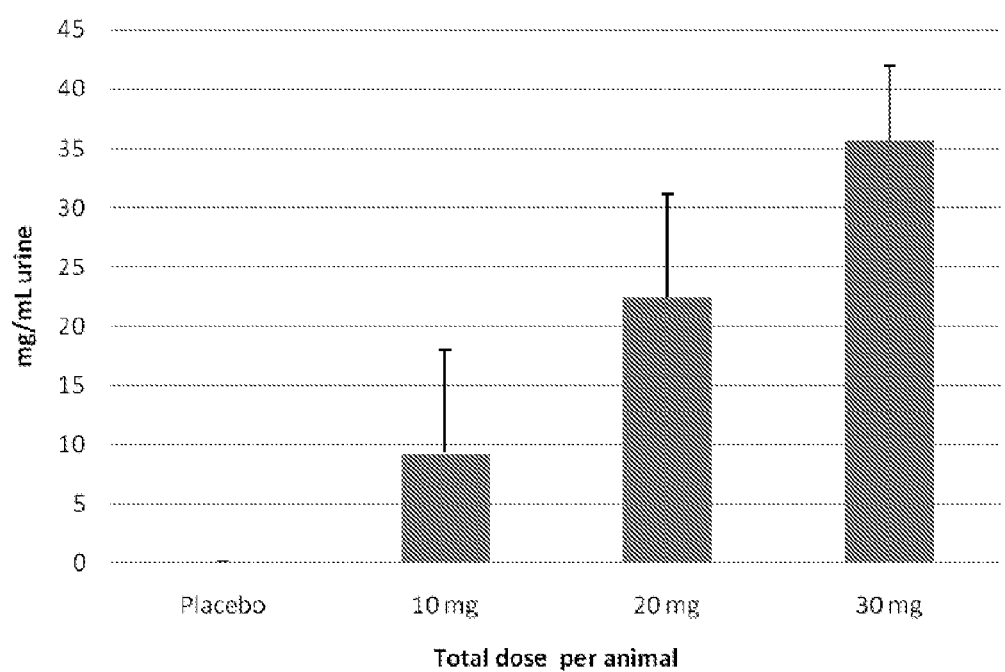
FIG. 41. Elimination of Motor1: Motor1 is eliminated in urine. Two hours after Motor1 injection, Motor1 concentration in the urine equals concentration in the plasma.
Figure 42:
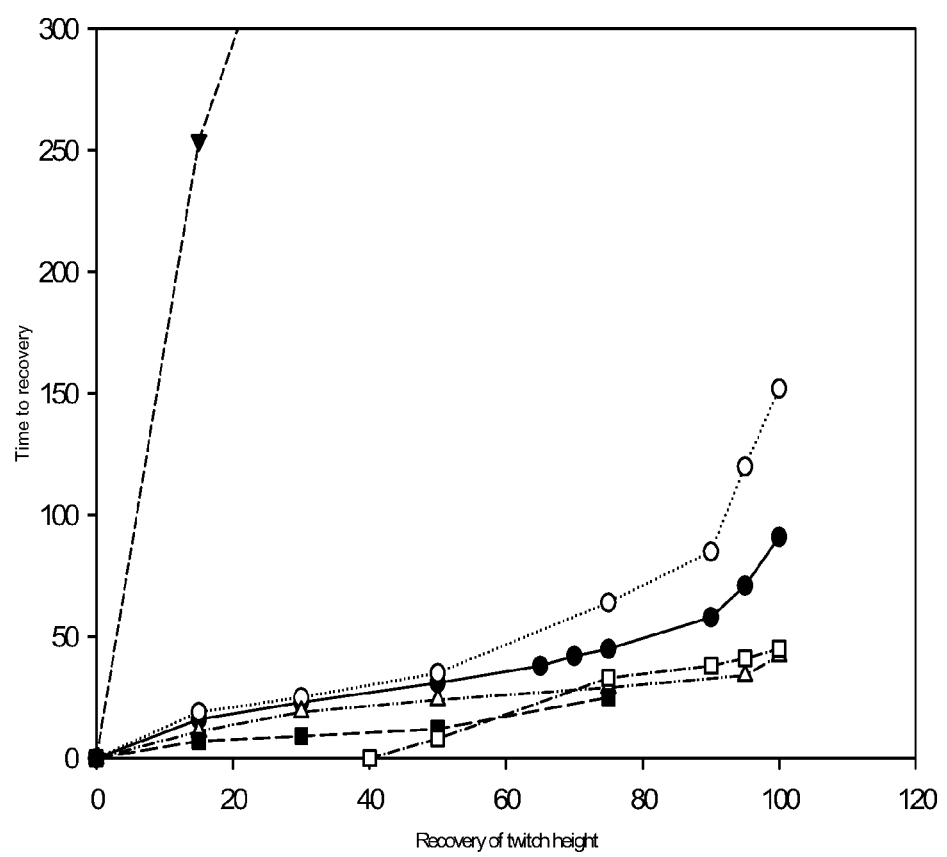
FIG. 42. Time to recovery of twitch height following complete cisatracurium-induced neuromuscular block. Recovery profile is shown in response to different Motor1 and Motor2 doses. Note that low-dose Motor2 reverses the benzylisoquinolinum cisatracurium faster than high-dose 1.
Figure 43:
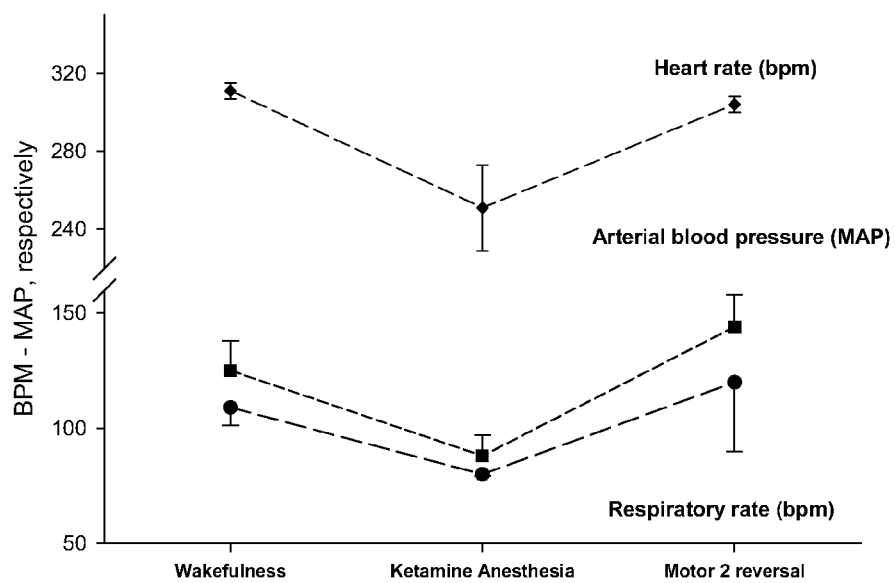
FIG. 43. Effects of ketamine and its reversal on respiratory and cardiovascular function.
Figure 44:
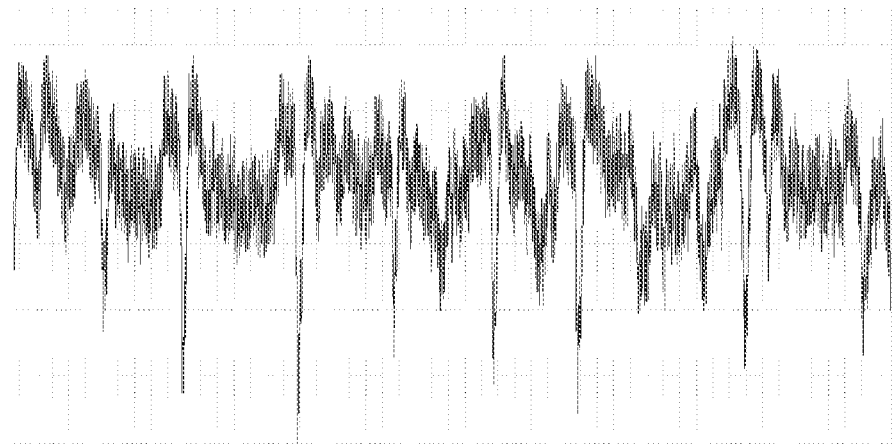
FIG. 44. Electroencephalogram (EEG) during ketamine anesthesia.
Figure 45:
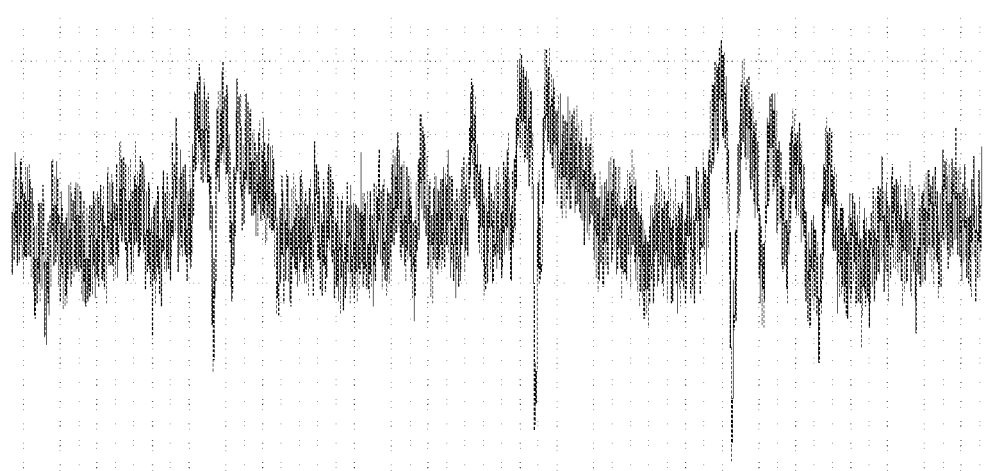
FIG. 45. EEG following Motor2 reversal of ketamine anesthesia.

FIG. 35 shows toxicology using Motor2. Varying concentrations of Motor2 were incubated with THP-1 (A) and HEK 293 (B) cells over a 48 hr period resulted in high cell survival up to 5 mM. Two complementary assays were used to analyze toxicology: an MTS and an AK release assay for the THP-1 cells. The AK release assay was conducted using 20 ul of supernatant from each sample studied using the MTS assay. The Vialight assay was used to assess cell viability in the HEK 293 cells. (UT=Untreated, Stx=Staurosporine, Triton=Trition-X-100). Unpaired t-test analysis was used with *P=0.01-0.05; P=0.001-0.01; *P, 0.001 for the statistical analysis of all figures presented.

While the invention has been particularly shown and described with reference to specific embodiments (some of which are preferred embodiments), it should be understood by those having skill in the art that various changes in form and detail may be made therein without departing from the spirit and scope of the present invention as disclosed herein.

What is claimed is:

1. A method for reversing drug-induced neuromuscular block and/or anesthesia in an individual comprising administering to an individual in need of reversal of neuromuscular block and/or anesthesia a composition comprising a compound having the following structure:

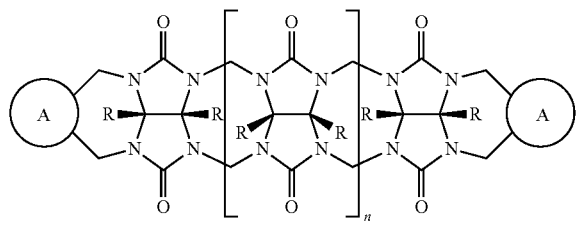

or a salt, a partial salt, a hydrate, or a stereoisomer thereof, wherein each R is independently hydrogen, $C_1$ to $C_{20}$ alkyl group, $C_3$ to $C_{20}$ carbocyclic group, $C_1$ to $C_{20}$ heterocyclic group, carboxylic acid group, ester group, amide group, hydroxy, or ether group;

wherein, optionally, adjacent R groups form a $C_3$ to $C_{20}$ carbocyclic ring or heterocyclic ring;

wherein each

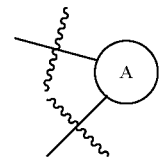

is independently a $C_5$ to $C_{20}$ carbocyclic ring system or $C_2$ to $C_{20}$ heterocyclic ring system, wherein the ring system comprises one or more rings;

wherein at least one ring system has at least one solubilizing group selected from sulfonic acid group, sulfonate salt group, phosphonic acid group, phosphonate salt group, and polyethylene glycol group;

wherein, optionally, the ring system has a targeting group;

wherein n is 1 to 5.

2. The method of claim 1, wherein each

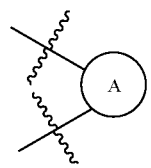

is independently a $C_5$ to $C_{20}$ carbocyclic ring system having one of the following structures:

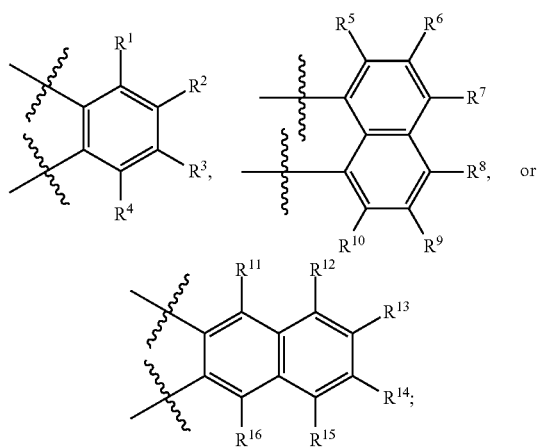

wherein at each occurrence of

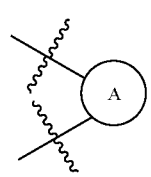

$R^1$ to $R^{16}$ is independently hydrogen, $C_1$ to $C_{20}$ alkyl group, halo group, hydroxyl group, nitro group, carboxylic acid group, ester group, amide group, ether group, $C_3$ to $C_{20}$ carbocyclic group, or $C_1$ to $C_{20}$ heterocyclic group,
provided that at least one of $R^1$ to $R^{16}$ in the compound has the following structure:

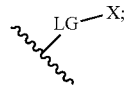

wherein LG is a linking group and X is the solubilizing group; and
wherein optionally one or more adjacent $R^1$ to $R^{16}$ groups are connected forming a carbocyclic ring or heterocyclic ring.

3. The method of claim 2, wherein

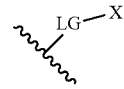

has the following structure:

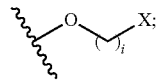

wherein each i is 1 to 20.

4. The method of claim 2, wherein at least one of the $R^1$ to $R^{16}$ groups in the structure has the following structure:

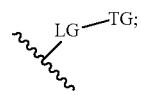

and wherein LG is a linking group and wherein TG is the targeting group.

5. The method of claim 2, wherein the

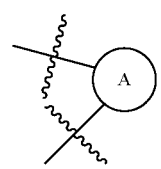

groups are the same.

6. The method of claim 3, wherein the compound has one of the following structures:

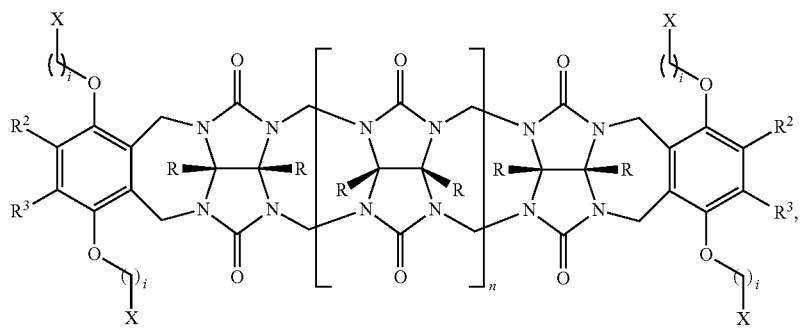

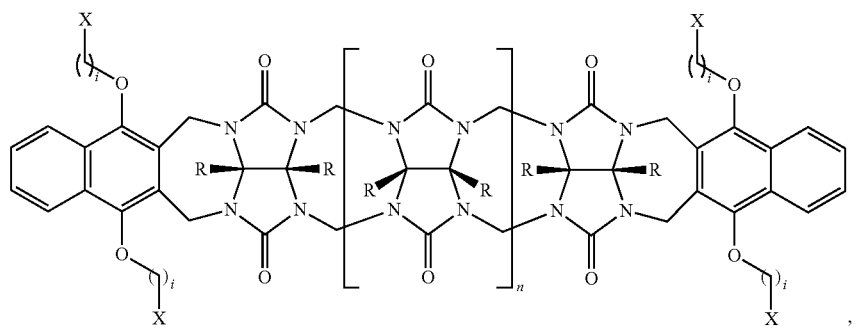

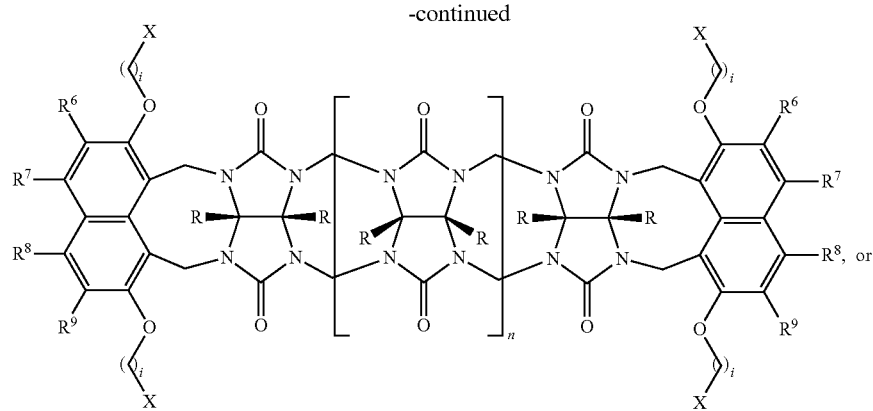
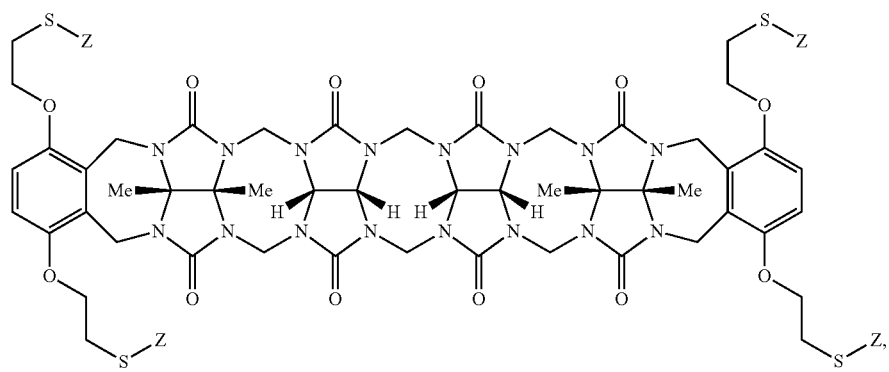
wherein Z is PEG group having a molecular weight of 200 to 10,000.
7. The method of claim 1, wherein the compound has one of the following structures:
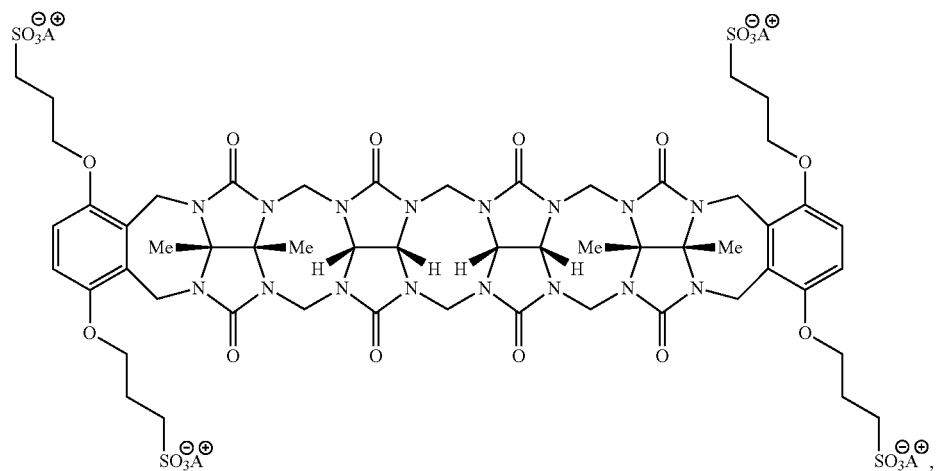

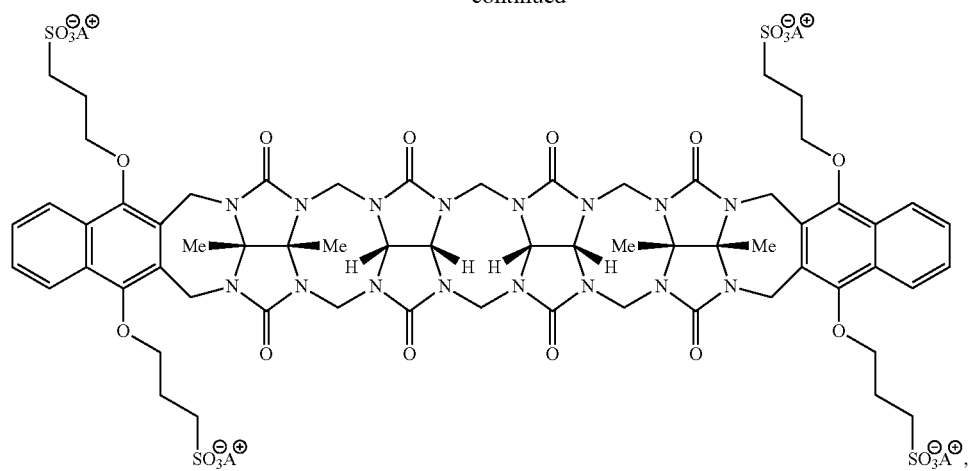
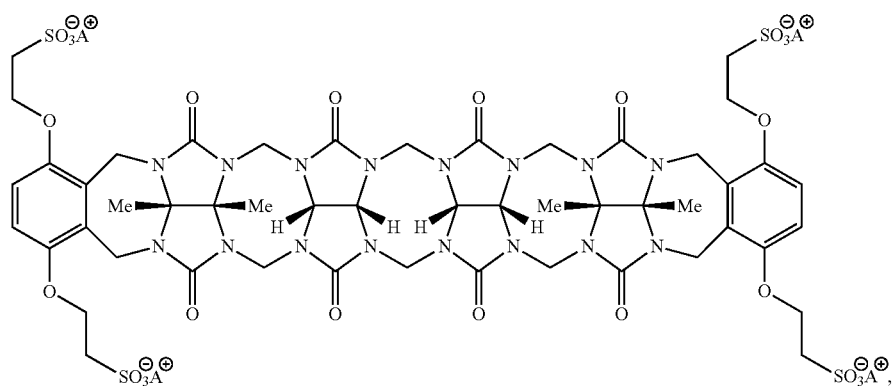
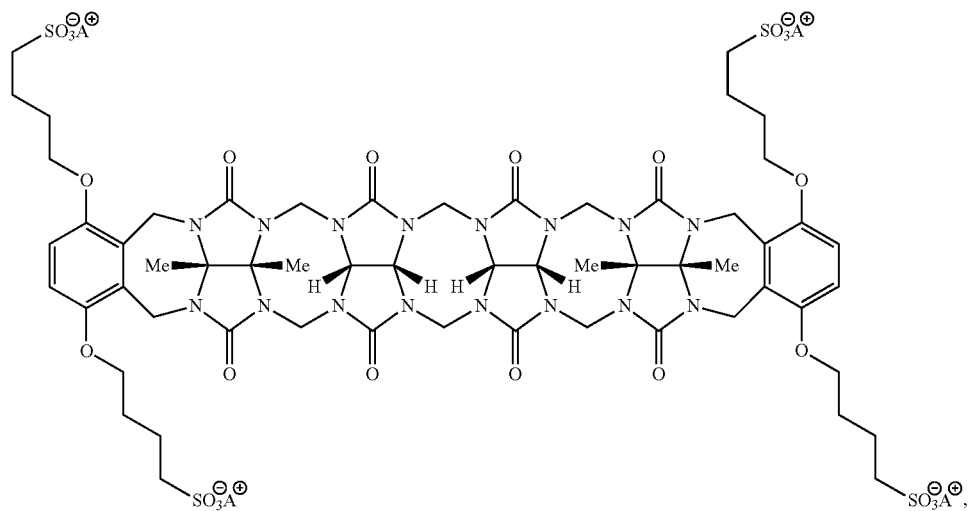

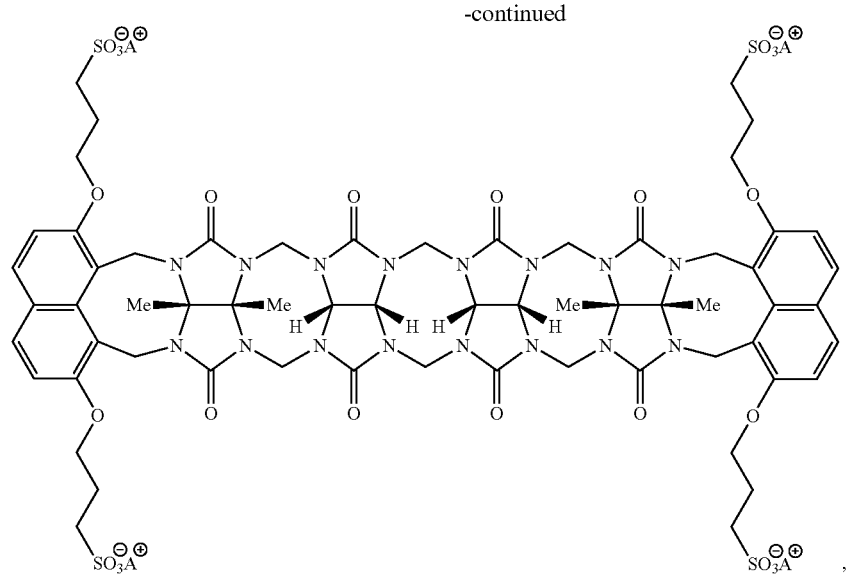

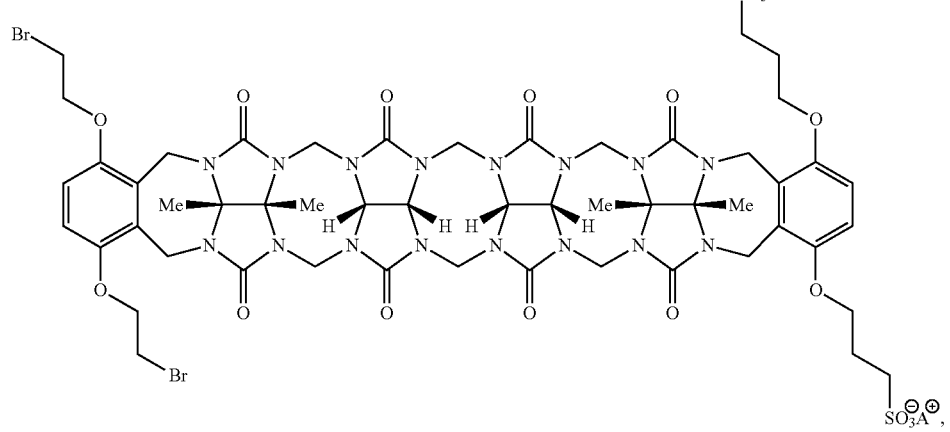

wherein A⁺ is H⁺, Na⁺, K⁺, Ca²⁺, Mg²⁺, Zn²⁺, H₄N⁺, Et₃NH⁺, Me₄N⁺, (HOCH₂CH₂)₃NH⁺, or a cationic form of ethylenediamine, piperazine, and trishydroxymethyl aminomethane (TRIS).

8. The method of claim 1, wherein the individual is in need of reversal of drug-induced neuromuscular block.

9. The method of claim 1, wherein the individual is in need of reversal of anesthesia.

10. The method of claim 1, wherein the individual is in need of reversal of drug-induced neuromuscular block and anesthesia.

11. The method of claim 1, wherein the individual in need is a human.

12. The method of claim 1, wherein the individual in need is a non-human mammal.

* * * * *